United States Patent [19]

Tai et al.

[11] Patent Number: 5,438,135
[45] Date of Patent: Aug. 1, 1995

[54] WATER-SOLUBLE TETRAAZAPORPHINS AND FLUOROCHROME FOR LABELING

[75] Inventors: Seiji Tai, Hitachi, Japan; Mitsuo Katayose, Mainz-Bretzenheim, Germany; Hiroo Watanabe, Hitachi, Japan

[73] Assignee: Hitachi Chemical Company, Tokyo, Japan

[21] Appl. No.: 846,169

[22] Filed: Mar. 5, 1992

[30] Foreign Application Priority Data

| Mar. 5, 1991 | [JP] | Japan | 3-038349 |
| Jun. 18, 1991 | [JP] | Japan | 3-146005 |
| Jul. 1, 1991 | [JP] | Japan | 3-159308 |
| Oct. 17, 1991 | [JP] | Japan | 3-268016 |

[51] Int. Cl.$^6$ ............ C07F 9/656; C07D 209/56; G01N 33/58
[52] U.S. Cl. ............ 540/128; 540/129; 540/132; 540/135; 540/136
[58] Field of Search ........... 540/124, 125, 128, 129, 540/132, 135, 136; 524/88

[56] References Cited

U.S. PATENT DOCUMENTS

| 4,042,413 | 8/1977 | Hauxwell et al. | 524/88 |
| 4,927,735 | 5/1990 | Era et al. | 540/140 |
| 4,943,681 | 7/1990 | Sato et al. | 430/495 |
| 4,943,681 | 7/1990 | Sato et al. | 540/128 |
| 5,075,203 | 12/1991 | Katayose et al. | 540/128 |
| 5,177,200 | 1/1993 | Kluger et al. | 524/88 |

FOREIGN PATENT DOCUMENTS

| 284369 | 9/1988 | European Pat. Off. . |
| 284370 | 9/1988 | European Pat. Off. . |
| 0391415 | 10/1990 | European Pat. Off. | 540/128 |
| 2053864 | 2/1990 | Japan | 540/135 |
| 8804777 | 6/1988 | WIPO . |
| 9002747 | 3/1990 | WIPO . |

OTHER PUBLICATIONS

Cook, et al, J. Chem. Soc. Perkins Trans. 1, 1988 2453–2458.
Leznoff, Phthalocyanines. vol. 2. (Weimheim VCH, 1993) pp. 112 and 127.
Sato et al. Chemical Abstracts, vol. 112, 1990 Abstract, 108641e.
Sounik et al. Chemical Abstracts vol. 116, 1992 Abstract 74754j.
Sato. et al. Chemical Abstracts, vol. 116, 1992 Abstract 72459t.
Hayashma. et al., Chemical Abstracts, vol. 111. 1989 Abstract 244195.
Miyazaki. et al, Chemical Abstracts, vol. 111, 1989 Abs. 244203.
Chemical Abstracts, vol. 113, 1990; H. Togashi, et al; p. 624.
Chemical Abstracts, vol. 113, 1990; S. Myazaki, et al; p. 627.
Chemical Abstracts, vol. 112, 1990; N. Ito, et al; p. 681.
Chemical Abstracts, vol. 116, 1992; Y. Suda; p. 646.

*Primary Examiner*—Mukund J. Shah
*Assistant Examiner*—P. K. Sripada
*Attorney, Agent, or Firm*—Antonelli, Terry, Stout & Kraus

[57] ABSTRACT

Water-soluble tetraazaporphins with novel structure is suitable as a fluorochrome for labeling and provides a reagent usable for fluorescence analysis process.

42 Claims, 56 Drawing Sheets

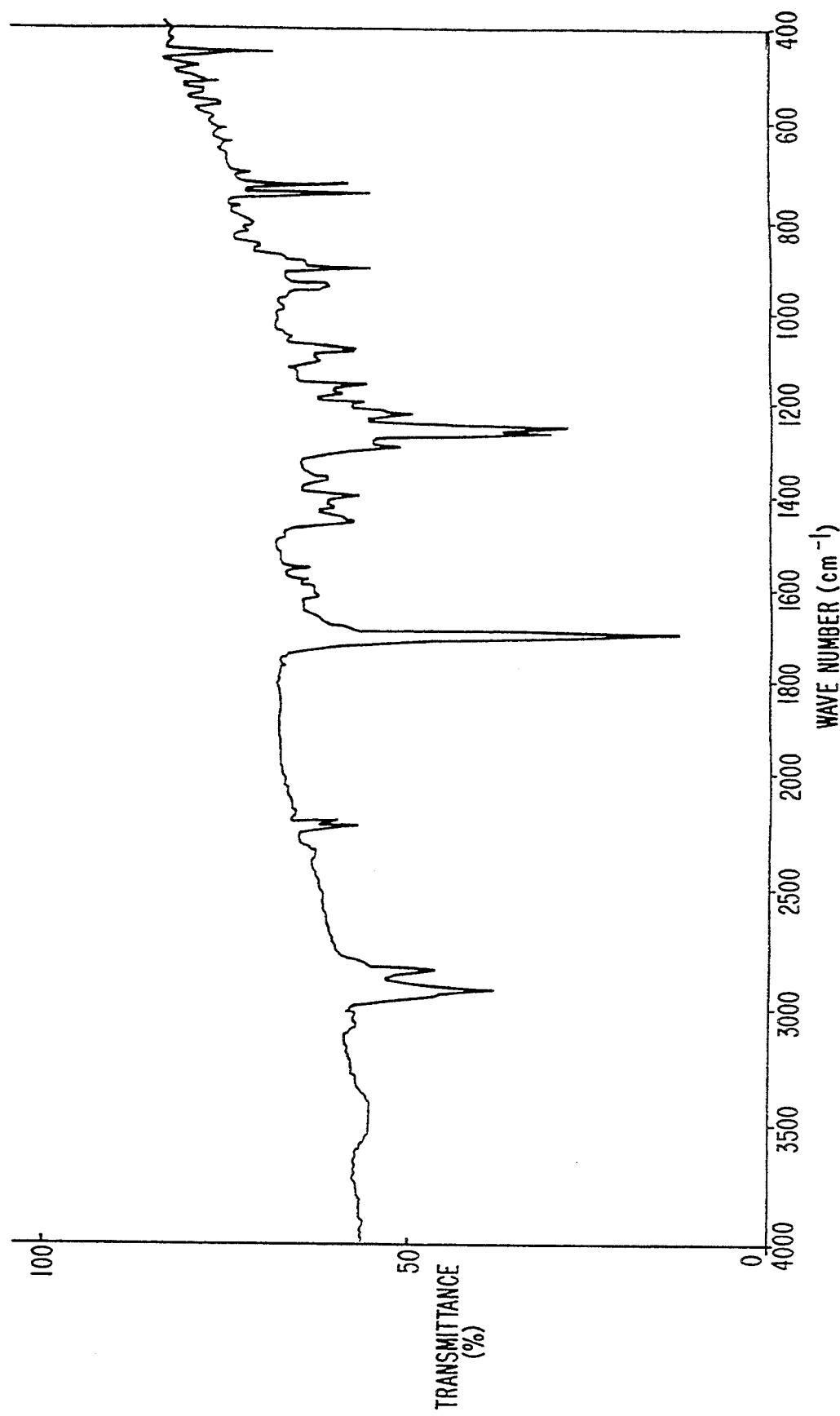
F I G. 35

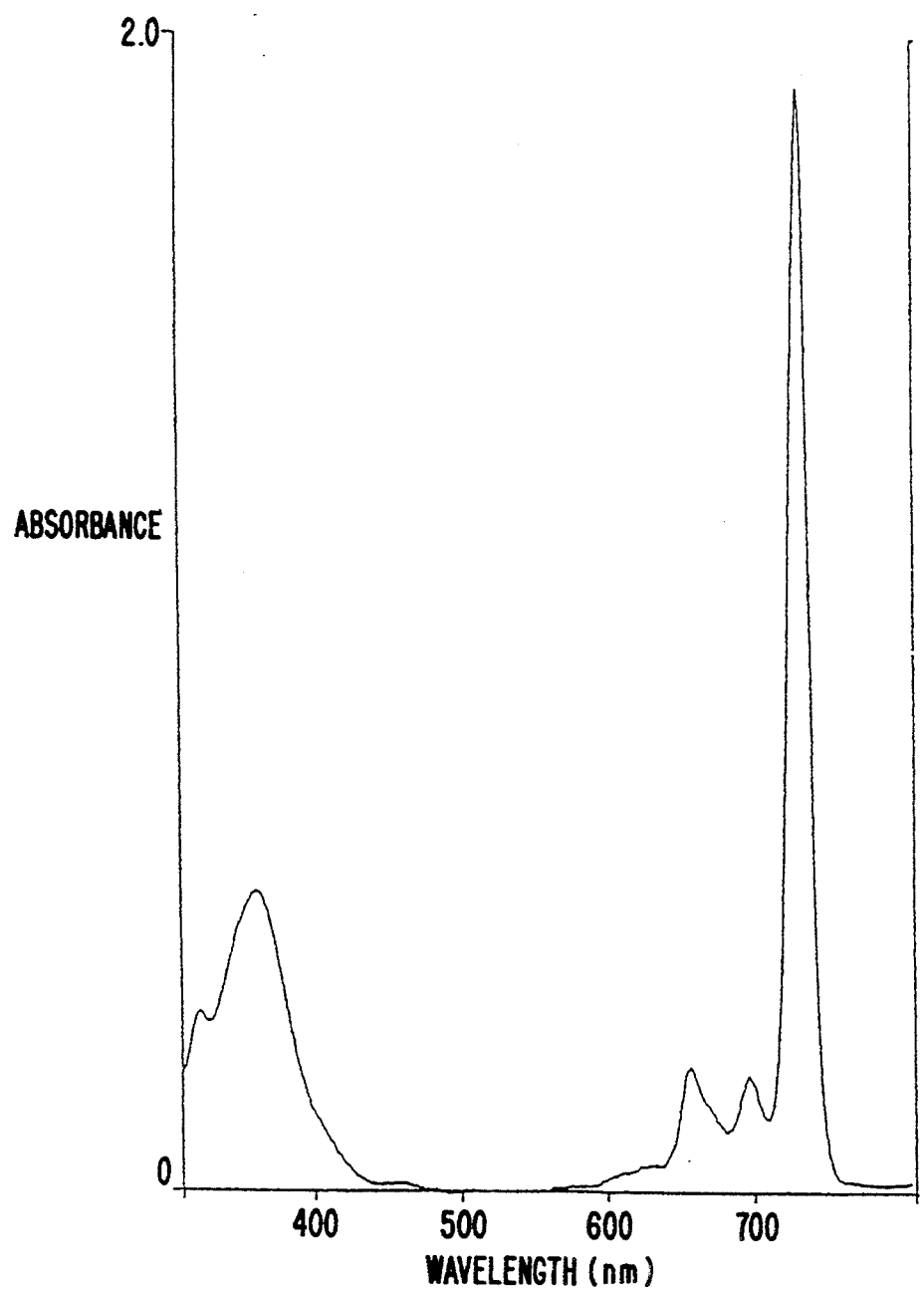

WATER-SOLUBLE TETRAAZAPORPHINS AND FLUOROCHROME FOR LABELING

BACKGROUND OF THE INVENTION

This invention relates to a water-soluble tetraazaporphin, a fluorochrome for labeling, a substance derived from an organism which has been labeled with the fluorochrome for labeling, a reagent comprising any of them, and a fluorescence analysis process using any of them.

Since early times, label methods have been utilized for investigation of various substances such as molecules, cells, antigen, antibody, DNA, RNA, polypeptides, etc. A label method using a radioisotope (RI) has heretofore been widely utilized because it has been studied for a long period of time. Since RI entails a severe exposure hazard, employment of RI requires both a special license and a special laboratory, and has been possible only for specified persons in specified facilities.

On the other hand, a method using a coloring substance, chemiluminescence method, fluorescence method, etc. are noted as label methods free from danger because they need not use RI. The method using a coloring substance cannot have a high detection sensitivity and hence is not so useful that it can replace the RI method. On the other hand, the chemiluminescence method and the fluorescence method are considered safe label methods which can replace the RI method, because their detection sensitivity can be enhanced. However, in the chemiluminescence method, luminescence is caused by combination of two or more chemical reactions, so that a troublesome procedure is required. Therefore, fluorescence label method is the most excellent label method from the viewpoint of safety, simplicity and high sensitivity.

There have known only dyes which emit fluorescence in the ultraviolet region, but Rhodamine dyes and oxazine dyes have recently come to be known to the art as dyes which can be excited by means of an argon laser or a He—Ne laser.

As a light source, a small semiconductor laser (670 to 840 nm) has recently become available at a low price. It is likely to become a leading light source because of the demand for an inexpensive, small and light instrument. However, there is a problem that conventional Rhodamine dyes, oxazine dyes and the like cannot be used when the semiconductor laser is used.

It has recently been proposed that phthalocyanine capable of showing a proper fluorescence quantum yield and a high water-solubility is used as a fluorochrome for labeling (International Publication Nos. WO 88/04777, WO 90/02747). However, the absorption maximum wavelength region and fluorescence emission wavelength region in Q-band of phthalocyanine derivatives are in a range of 670 to 690 nm, so that the phthalocyanine derivatives cannot be excited by means of a semiconductor laser having an output wavelength of 700 nm or more. Moreover, when a semiconductor laser having an output wavelength of 670 to 680 nm is used, its output wavelength region and the fluorescence emission wavelength region overlap each other, so that it is impossible to judge whether light detected is derived from fluorescent radiation emitted or laser beam scattered. Therefore, the phthalocyanine derivatives cannot be utilized. In short, the phthalocyanine derivatives have a fatal defect in that they cannot be used at all in a system using a semiconductor laser which is a leading system.

Furthermore, in a system in which a substance in a living body, for example, a heme in blood is present together with an analyte to be measured, measurement of the analyte is hindered by the substance in the living body because the heme has an absorption wavelength region of 700 nm or less which overlaps with that of phthalocyanine.

SUMMARY OF THE INVENTION

This invention provides a novel compound, a fluorochrome for labeling, a reagent, a reagent for clinical examination, and a fluorescence analysis process which are not affected by substances in a living body, such as hemes present in blood, can be used for measurement by means of an inexpensive and small semiconductor laser (670 to 840 nm), and are useful for assay of various antigens, drugs, DNAs, etc. and analysis of the base sequence of DNA.

The present inventors earnestly investigated in order to solve the above problems, and consequently have accomplished this invention.

This invention relates to the following items (1) to (12).

(1) A water-soluble tetraazaporphin represented by the general formula (I):

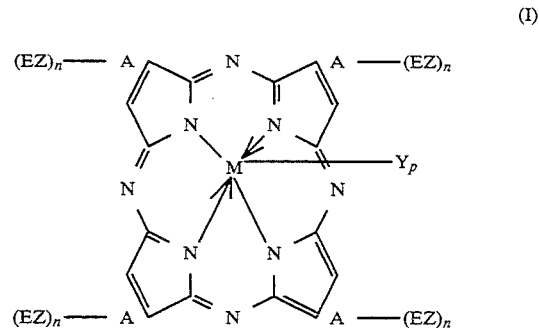

wherein M is $H_2$, Mg, Al, Si, P, Zn, Ga, Ge or Sc; Y is a halogen atom $-OR^1$, $-NR_2^2$ or $-SR^3$ (wherein $R^1$, $R^2$ and $R^3$ are independently a hydrogen atom, an alkyl group which may have one or more hydrophilic substituents, an aryl group which may have one or more hydrophilic substituents, an aralkyl group which may have one or more hydrophilic substituents, an acyl group which may have one or more hydrophilic substituents, a silyl group which may have one or more hydrophilic substituents, or a phosphorus-atom-containing group which may have one or more hydrophilic substituents); p is zero or an integer of 1 or 2 indicating the number of Y's bonded to M; A is a fused polycyclic aromatic ring formed from two or more aromatic ring and having substituents XQ's in a number of m (X is an oxygen atom or a sulfur atom; and Q is a saturated or unsaturated hydrocarbon group or a heterocyclic group; and each m is the same or different and independently an integer of 1 to 4); each n is the same or different and independently zero or an integer of 1 or more, 4n (the sum of four n's) being an integer of 1 or more; each substituent (EZ) in a number of n is the same or different and are independently bonded to the fused polycyclic aromatic ring A and/or Q; and E is a cationic group in the case of Z being an anion, E is an anionic group in the case of Z being a cation, and E is a bonded group containing a polyethylene glycol residue, a polyether residue, a polyamine residue, a polyalcohol residue or a polycarboxylic acid residue in the case of Z being absent.

(2) A fluorochrome for labeling comprising a compound represented by the general formula (II):

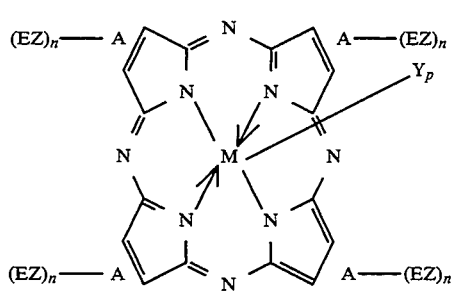

(II)

wherein M is $H_2$, Mg, Al, Si, P, Zn, Ga, Ge or Sc; Y is a halogen atom, $-OR^1$, $-NR_2^2$ or $-SR^3$ (wherein, and $R^1$, $R^2$ $R^3$ are independently a hydrogen atom, an alkyl group which may have one or more hydrophilic substituents, an aryl group which may have one or more hydrophilic substituents, an aralkyl group which may have one or more hydrophilic substituents, an acyl group which may have one or more hydrophilic substituents, a silyl group which may have one or more hydrophilic substituents, or a phosphorus-atom-containing group which may have one or more hydrophilic substituents); p is zero or an integer of 1 or 2 indicating the number of Y's bonded to M; A is a fused polycyclic aromatic ring formed from two or more aromatic rings and having substituents $X^1Q$'s or Q's in a number of m ($X^1$ is an oxygen atom, a sulfur atom, a nitrogen atom, a phosphorus atom, a silicon atom, a selenium atom, NH.CO, $NH.PO_2$, $NH.SO_2$, O.CO, $O.SO_2$, $O.PO_2$, S.CO, $S.SO_2$, $S.PO_2$, CO, $SO_2$ or $PO_2$; Q is a saturated or unsaturated hydrocarbon group or a heterocyclic group; and each m is the same or different and independently an integer of 1 to 4); each n is the same or different and independently zero or an integer of 1 or more, 4n (the sum of four n's) being an integer of 1 or more; each substituent (EZ) in a number of n is the same or different and independently bonded to the fused polycyclic aromatic ring A and/or Q; and E is a cationic group in the case of Z being an anion, E is an anionic group in the case of Z being a cation, and E is a bonded group containing a polyethylene glycol residue, a polyether residue, a polyamine residue, a polyalcohol residue or a polycarboxylic acid residue in the case of Z being absent.

(3) A reagent comprising the fluorochrome for labeling of the above item (2).

(4) A reagent comprising the fluorchrome for labeling of the above item (2) and a nonionic surfactant.

(5) A substance derived from an organism which has been labeled with the fluorochrome for labeling of the above item (2).

(6) A reagent comprising the labeled substance derived from an organism of the above item (5).

(7) A reagent comprising the labeled substance derived from an organism of the above item (5) and a nonionic surfactant.

(8) A substance derived from an organism according to the above item (5) or a reagent according to the above item (6) or (7), wherein the substance derived from an organism is an antigen, an antibody or a nucleotide.

(9) A substance derived from an organism or a reagent according to the above item (8), wherein the antigen is a drug.

(10) A substance derived from an organism or a reagent according to the above item (8), wherein the antibody is a monoclonal antibody.

(11) A substance derived from an organism or a reagent according to the above item (8), wherein the nucleotide is an oligonucleotide or a polynucleotide.

(12) A substance derived from an organism or a reagent according to the above item (8), wherein the nucleotide is ATP, CTP, GTP, TTP, UTP, dATP, dCTP, dGTP, dTTP, dUTP, ddATP, ddCTP, ddGTP, ddTTP, ddUTP, or a derivative thereof.

(13) A fluorescence analysis process characterized by using the fluorochrome for labeling of the above item (2) as a fluorescent label.

(14) A fluorecence analysis process according to the above item (13), which uses a semiconductor laser having an output wavelength of 670 to 840 nm as a light source.

(15) A fluorescence analysis process according to the above item (13) or (14), which uses the labeled substance derived from an organism of the above item (5).

BRIEF DESCRIPTION OF THE DRAWINGS

FIGS. 3, 4, 5, 7, 11, 14, 17, 19, 22, 25, 28, 30, 31, 33, 35, 37, 39, 40, 43 and 45 show IR spectra (KBr) of compounds of this invention.

FIGS. 47, 48, 49, 50, 51, 52, 53, 54, 55 and 56 show electronic spectra (methanol solution) of compounds of this invention.

DESCRIPTION OF THE PREFERRED EMBODIMENTS

Figure 1:
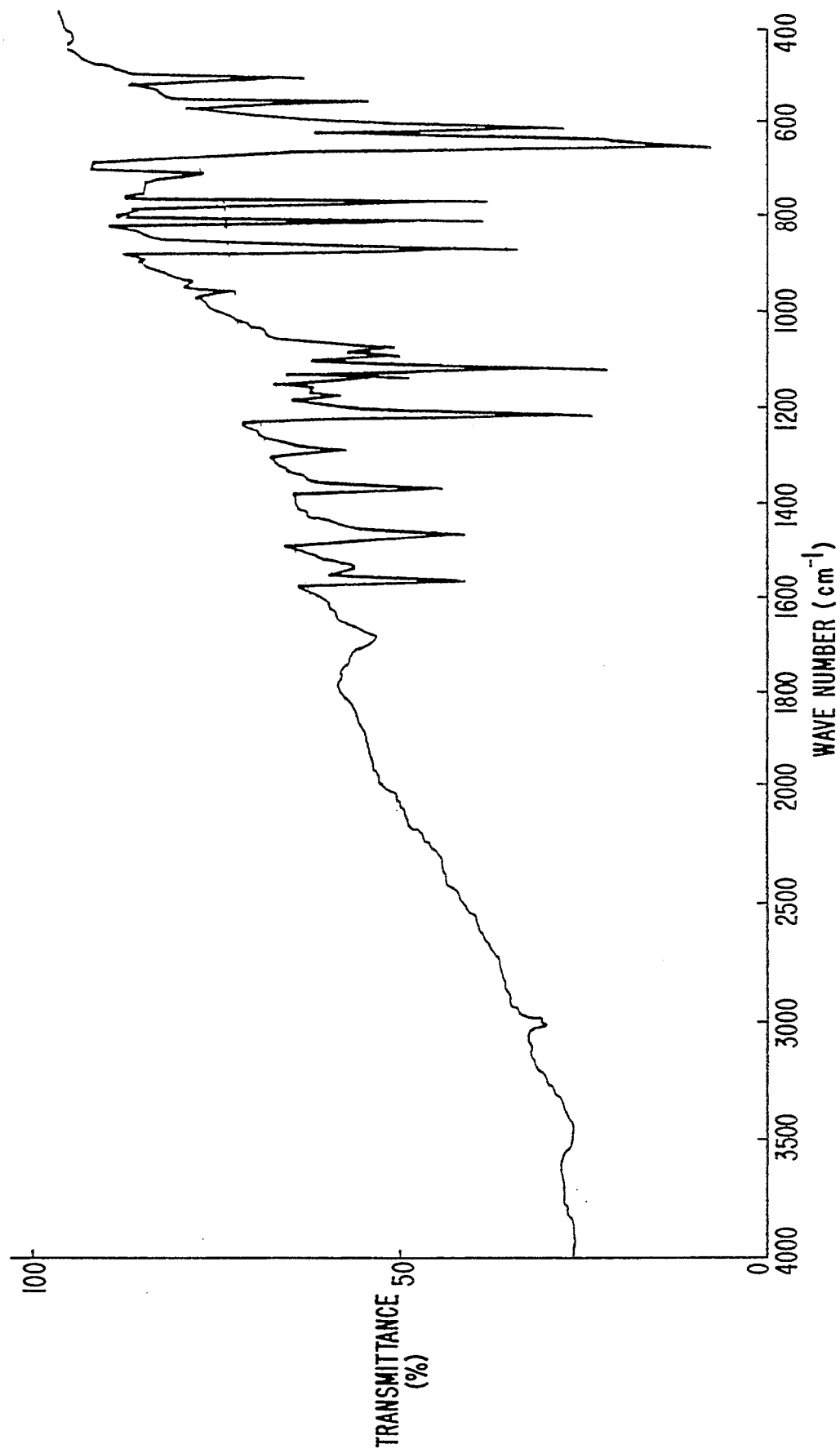
FIGS. 1, 29, 32 and 34 show IR spectra (neat) of compounds of this invention.

The novel tetraazaporphin derivative of the general formula (I) is highly soluble not only in water but also in polar organic solvents such as methanol, ethanol, etc., and hence can easily be purified to be improved in purity, by chromatography, recrystallization, reprecipitation, etc.

In the compound of the general formula (I) of this invention, for $R^1$, $R^2$ and $R^3$, specific examples of the alkyl group which may have one or more hydrophilic substituents are linear, branched or cyclic groups such as methyl, ethyl, propyl, butyl, pentyl, hexyl, heptyl, octyl, nonyl, decyl, dodecyl, tetradecyl, hexadecyl, octadecyl, eicosyl, docosyl, etc., and groups formed by attachment thereto of hydrophilic substituents such as hydroxyl group, carboxylic acid groups, sulfonic acid groups, phosphoric acid group, etc. The group which may have one or more hydrophilic substituents includes linear, branched or cyclic groups such as formyl, acetyl, propionyl, butyryl, valeryl, pivaloyl, hexanoyl, octanoyl, lauroyl, palmitoyl, stearoyl, etc., and groups formed by attachment thereto of hydrophilic substituents such as hydroxyl group, carboxylic acid groups, sulfonic acid groups, phosphoric acid group, etc. The silyl group which may have one or more hydrophilic substituents includes silyl groups having a linear, branched or cyclic group, such as trimethylsilyl, triethylsilyl, tripropylsilyl, tributylsilyl, triamylsilyl, trihexylsilyl, dimethylphenylsilyl, diphenylmethylsilyl, triphenylsilyl, etc., and groups formed by attachment thereto of hydrophilic substituents such as hydroxyl group, carboxylic acid groups, sulfonic acid groups, phosphoric acid group, etc. The aryl group which may have one or more hydrophilic substituents includes phenyl group, biphenyl group, terphenyl group, cumenyl group, furyl group, thienyl group, pyrrolyl group, and groups formed by attachment thereto of hydrophilic substituents such as hydroxyl group, carboxylic acid groups, sulfonic acid groups, phosphoric acid group, etc. The aralkyl group which may have one or more hydrophilic substituents includes benzyl group, phenethyl group, and groups formed by attachment of hydrophilic substituents such as hydroxyl group, carboxylic acid groups, sulfonic acid groups, phosphoric acid group, etc. The phosphorus-atom-containing group which may have one or more hydrophilic substituents includes phosphoric acid residue, phosphoric esters, etc.

For Q, specific examples of the saturated or unsaturated, linear, branched or cyclic hydrocarbon group are methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, undecyl group, dodecyl group, vinyl group, 1-propenyl group, allyl group, isopropenyl group, 1-butenyl group, 2-butenyl group, 2-pentenyl group, ethynyl group, cyclopropyl group, cyclobutyl group, cyclopentyl group, cyclohexyl group, cyclohexenyl group, phenyl group, tolyl group, xylyl group, mesityl group, cumenyl group, benzyl group, phenethyl group, naphthyl group, etc. The heterocyclic group includes furyl group, thienyl group, pyrrolyl group, etc.

The anion represented by Z includes $Cl^-$, $Br^-$, $I^-$, $ClO_4^-$, $SO_4^{2-}$, $PO_4^{3-}$, etc. The cation represented by Z includes $H^+$, $Li^+$, $Na^+$, $K^+$, $Mg^{2+}$, $Ca^{2+}$, ammonium ion, etc. The cationic group represented by E includes, for example,

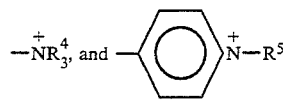

wherein $R^4$ and $R^5$ are independently an alkyl group which may have one or more hydrophilic substituents, an aryl group which may have one or more hydrophilic substituents, or an aralkyl group which may have one or more hydrophilic substituents, the alkyl group, the aryl group and the aralkyl group being the same as those exampilfied above for $R^1$, $R^2$ and $R^3$. The anionic group represented by E includes $-COO^-$, $-OSO_3^-$, $-O-PO_3^-$, $-SO_3^-$, etc. The fused polycyclic aromatic ring formed from two or more aromatic rings which is represented by A, includes naphthalene ring, anthracene ring, phenanthrene ring, quinoline ring, quinoxaline ring, chrysene ring, etc. The bonding position of the fused polycyclic aromatic ring has not any limitation.

The kind and form of the above substituents have a great influence not only on the solubility of the novel tetraazaporphin of the above general formula (I) in water or polar organic solvents but also on the waveform of absorption spectrum and the wavelength of absorption maximum, or the wavelength of fluorescence emission maximum and the fluorescence emission intensity, in a solution.

The symbol "p" represents zero or an integer of 1 or 2 indicating the number of Y's bonded to M. When M is $H_2$, Mg or Zn, p is zero. When M is Al, Sc or Ga, p is 1. When M is Si, P or Ge, p is 2.

In the compound of the general formula (I), the water-soluble group represented by EZ is bonded to the fused polycyclic aromatic ring represented by A and/or Q bonded to the aromatic ring. The position(s) to which EZ is bonded is determined by the synthetic pathway of the compound of the general formula (I). For example, when as shown in Exmaple 3 described hereinafter, a water-soluble group is introduced later into a compound having Q with no special substituent, the product has water-soluble sulfonic acid groups as substituents in both the fused polycyclic aromatic ring represented by A and a benzene ring represented by Q. On the other hand, when as shown in Example 4 described hereinafter, XQ having one or more substituents (ester groups) convertible into EZ by hydrolysis is introduced into the fused polycyclic aromatic ring represented by A and then hydrolyzed, the product has a water-soluble group(s) EZ as substituent(s) only in Q.

Specific exmaples of the novel tetraazaporphin of this invention are shown as illustrative compounds in Tables 1 to 6.

TABLE 1

| Illustrative compd. No. | M | A | Y | p | XQ | m | EZ | 4n |
|---|---|---|---|---|---|---|---|---|
| 1 | Si | 2,3-Naphthalene ring | $OSi(C_4H_9)_3$ | 2 | S—⟨phenyl⟩ | 1 | COONa | 8 |
| 2 | Si | 2,3-Naphthalene ring | $OSi(C_4H_9)_3$ | 2 | S—⟨phenyl⟩ | 2 | COONa | 16 |

TABLE 1-continued

| Illustrative compd. No. | M | A | Y | p | XQ | m | EZ | 4n |
|---|---|---|---|---|---|---|---|---|
| 3 | Si | 2,3-Naphthalene ring | OSi(C$_2$H$_5$)$_3$ | 2 | 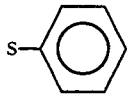 | 1 | COONa | 8 |
| 4 | Si | 2,3-Naphthalene ring | OSi(C$_2$H$_5$)$_3$ | 2 | 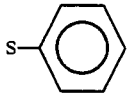 | 2 | SO$_3$Na | 8 |
| 5 | Si | 2,3-Naphthalene ring | OSi(C$_4$H$_9$)$_3$ | 2 | 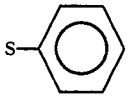 | 1 | SO$_3$Na | 6 |
| 6 | Si | 2,3-Naphthalene ring | OSi(C$_4$H$_9$)$_3$ | 2 | 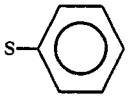 | 1 | SO$_3$Na | 8 |
| 7 | Si | 2,3-Naphthalene ring | OSi(C$_4$H$_9$)$_3$ | 2 | 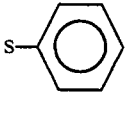 | 1 | OPO$_3$Na | 8 |
| 8 | Si | 2,3-Naphthalene ring | 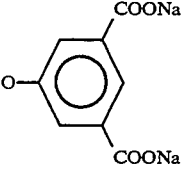 | 2 | 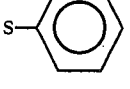 | 1 | CO$_2$Na | 8 |
| 9 | Si | 2,3-Naphthalene ring | 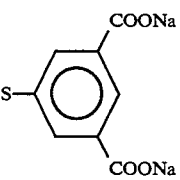 | 2 | 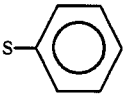 | 1 | CO$_2$Na | 8 |
| 10 | Si | 2,3-Naphthalene ring | 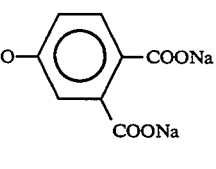 | 2 |  | 2 | CO$_2$Na | 16 |
| 11 | Si | 2,3-Naphthalene ring | 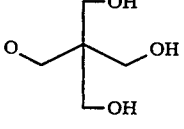 | 2 |  | 1 | CO$_2$Na | 8 |
| 12 | Si | 2,3-Naphthalene ring | 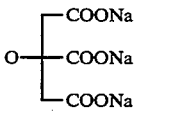 | 2 |  | 1 | CO$_2$Na | 8 |
| 13 | Si | 2,3-Naphthalene ring | OH | 2 | 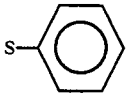 | 2 | CO$_2$Na | 16 |

TABLE 1-continued

| Illustrative compd. No. | M | A | Y | p | XQ | m | EZ | 4n |
|---|---|---|---|---|---|---|---|---|
| 14 | Si | 2,3-Naphthalene ring | 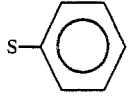 COONa / O / COONa | 2 | 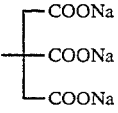 S— | 1 | SO3—COONa / COONa / COONa | 6 |
| 15 | Si | 2,3-Naphthalene ring | OPO3Na | 2 | 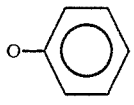 O— | 2 | COONa | 16 |
| 16 | Si | 2,3-Naphthalene ring | OSi(C3H7)3 | 2 | SC2H4 | 1 | COONa | 4 |
| 17 | Al | 2,3-Naphthalene ring | OH | 1 | 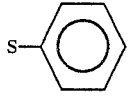 S— | 2 | COONa | 16 |
| 18 | Zn | 2,3-Naphthalene ring | — | 0 | 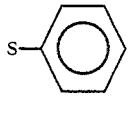 S— | 2 | COONa | 16 |
| 19 | Ge | 2,3-Naphthalene ring | OH | 2 | 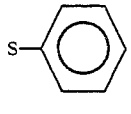 S— | 2 | COONa | 16 |
| 20 | H2 | 2,3-Naphthalene ring | — | 0 | 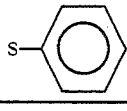 S— | 2 | COONa | 16 |

TABLE 2

| Illustrative compd. No. | M | A | Y | p | XQ | m | EZ | 4n |
|---|---|---|---|---|---|---|---|---|
| 21 | Si | 2,3-Quinoline ring | OSi(C4H9)3 | 2 | 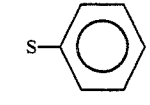 S— | 1 | COONa | 8 |
| 22 | Si | 2,3-Quinoline ring | OSi(C4H9)3 | 2 | 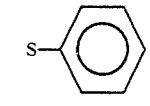 S— | 2 | COONa | 16 |
| 23 | Si | 2,3-Quinoline ring | OSi(C2H5)3 | 2 | 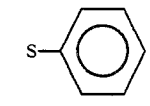 S— | 1 | COONa | 8 |
| 24 | Si | 2,3-Quinoline ring | OSi(C2H5)3 | 2 | 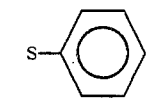 S— | 2 | COONa | 16 |
| 25 | Si | 2,3-Quinoline ring | OSi(C4H9)3 | 2 | 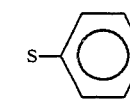 S— | 1 | SO3Na | 6 |
| 26 | Si | 2,3-Quinoline ring | OSi(C4H9)3 | 2 | 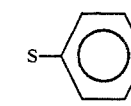 S— | 1 | SO3Na | 8 |

TABLE 2-continued

| Illustrative compd. No. | M | A | Y | p | XQ | m | EZ | 4n |
|---|---|---|---|---|---|---|---|---|
| 27 | Si | 2,3-Quinoline ring | OSi(C₄H₉)₃ | 2 | S—⌬ | 1 | OPO₃Na | 8 |
| 28 | Si | 2,3-Quinoline ring | O—⌬(COONa)(COONa) | 2 | S—⌬ | 1 | CO₂Na | 8 |
| 29 | Si | 2,3-Quinoline ring | S—⌬(COONa)(COONa) | 2 | S—⌬ | 1 | CO₂Na | 8 |
| 30 | Si | 2,3-Quinoline ring | O—⌬(COONa)(COONa) | 2 | S—⌬ | 2 | CO₂Na | 16 |
| 31 | Si | 2,3-Quinoline ring | O—C(OH)(OH)(OH) | 2 | S—⌬ | 2 | CO₂Na | 16 |
| 32 | Si | 2,3-Quinoline ring | O—C(COONa)(COONa)(COONa) | 2 | S—⌬ | 1 | CO₂Na | 8 |
| 33 | Si | 2,3-Quinoline ring | OH | 2 | S—⌬ | 1 | SO₃—C(COONa)(COONa)(COONa) | 6 |
| 34 | Si | 2,3-Quinoline ring | O—⌬(COONa)(COONa) | 2 | S—⌬ | 2 | SO₃—C(COONa)(COONa)(COONa) | 12 |
| 35 | Si | 2,3-Quinoline ring | OPO₃Na | 2 | O—⌬ | 2 | CO₂Na | 16 |
| 36 | Si | 2,3-Quinoline ring | NH.CO—⌬(COONa)(COONa) | 2 | O— | 1 | CO₂Na | 12 |
| 37 | Al | 2,3-Quinoline ring | OH | 1 | S—⌬ | 2 | CO₂Na | 16 |

TABLE 2-continued

| Illustrative compd. No. | M | A | Y | p | XQ | m | EZ | 4n |
|---|---|---|---|---|---|---|---|---|
| 38 | Zn | 2,3-Quinoline ring | — | 0 | 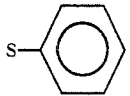 | 2 | CO$_2$Na | 16 |
| 39 | Ge | 2,3-Quinoline ring | OH | 2 | 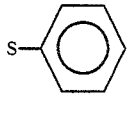 | 2 | CO$_2$Na | 16 |
| 40 | H$_2$ | 2,3-Quinoline ring | — | 0 | 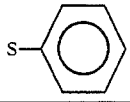 | 2 | CO$_2$Na | 16 |

TABLE 3

| Illustrative compd. No. | M | A | Y | p | XQ | m | EX | 4n |
|---|---|---|---|---|---|---|---|---|
| 41 | Si | 2,3-Quinoxaline ring | OSi(C$_4$H$_9$)$_3$ | 2 | 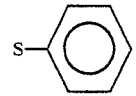 | 1 | CO$_2$Na | 8 |
| 42 | Si | 2,3-Quinoxaline ring | OSi(C$_4$H$_9$)$_3$ | 2 | 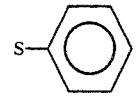 | 2 | CO$_2$Na | 16 |
| 43 | Si | 2,3-Quinoxaline ring | OSi(C$_2$H$_5$)$_3$ | 2 | 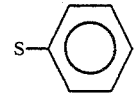 | 1 | CO$_2$Na | 8 |
| 44 | Si | 2,3-Quinoxaline ring | OSi(C$_2$H$_5$)$_3$ | 2 | 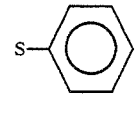 | 2 | SO$_3$Na | 8 |
| 45 | Si | 2,3-Quinoxaline ring | OSi(C$_4$H$_9$)$_3$ | 2 | 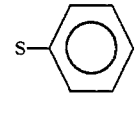 | 1 | SO$_3$Na | 6 |
| 46 | Si | 2,3-Quinoxaline ring | OSi(C$_4$H$_9$)$_3$ | 2 | 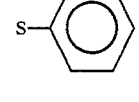 | 1 | SO$_3$Na | 8 |
| 47 | Si | 2,3-Quinoxaline ring | OSi(C$_2$H$_5$)$_3$ | 2 | 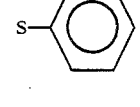 | 1 | OPO$_3$Na | 8 |
| 48 | Si | 2,3-Quinoxaline ring | 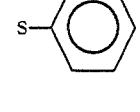 | 2 |  | 1 | CO$_2$Na | 8 |

TABLE 3-continued

| Illustrative compd. No. | M | A | Y | p | XQ | m | EX | 4n |
|---|---|---|---|---|---|---|---|---|
| 49 | Si | 2,3-Quinoxaline ring | S-C₆H₃(COONa)₂ | 2 | S-C₆H₅ | 1 | CO₂Na | 8 |
| 50 | Si | 2,3-Quinoxaline ring | O-C₆H₃(COONa)₂ | 2 | S-C₆H₅ | 2 | CO₂Na | 16 |
| 51 | Si | 2,3-Quinoxaline ring | O-C(CH₂OH)₃ | 2 | S-C₆H₅ | 2 | CO₂Na | 16 |
| 52 | Si | 2,3-Quinoxaline ring | O-C(COONa)₃ | 2 | S-C₆H₅ | 1 | CO₂Na | 8 |
| 53 | Si | 2,3-Quinoxaline ring | OH | 2 | S-C₆H₅ | 2 | CO₂Na | 16 |
| 54 | Si | 2,3-Quinoxaline ring | O-C₆H₃(COONa)₂ | 2 | S-C₆H₅ | 2 | CO₂Na | 16 |
| 55 | Si | 2,3-Quinoxaline ring | OPO₃Na | 2 | O-C₆H₅ | 2 | CO₂Na | 16 |
| 56 | Si | 2,3-Quinoxaline ring | NH.CO-C₆H₃(COONa)₂ | 2 | O- | 1 | CO₂Na | 12 |
| 57 | Al | 2,3-Quinoxaline ring | OH | 1 | S-C₆H₅ | 2 | CO₂Na | 16 |
| 58 | Zn | 2,3-Quinoxaline ring | — | 0 | S-C₆H₅ | 2 | CO₂Na | 16 |
| 59 | Ge | 2,3-Quinoxaline ring | OH | 2 | S-C₆H₅ | 2 | CO₂Na | 16 |

TABLE 3-continued

| Illustrative compd. No. | M | A | Y | p | XQ | m | EX | 4n |
|---|---|---|---|---|---|---|---|---|
| 60 | H$_2$ | 2,3-Quinoxaline ring | — | 0 | S—⌬ | 2 | CO$_2$Na | 16 |

TABLE 4

| Illustrative compd. No. | M | A | Y | p | XQ | m | EZ | 4n |
|---|---|---|---|---|---|---|---|---|
| 61 | Si | 9,10-Phenanthrene ring | OSi(C$_4$H$_9$)$_3$ | 2 | S—⌬ | 1 | CO$_2$Na | 8 |
| 62 | Si | 9,10-Phenanthrene ring | OSi(C$_4$H$_9$)$_3$ | 2 | S—⌬ | 2 | CO$_2$Na | 16 |
| 63 | Si | 9,10-Phenanthrene ring | OSi(C$_2$H$_5$)$_3$ | 2 | S—⌬ | 1 | CO$_2$Na | 8 |
| 64 | Si | 9,10-Phenanthrene ring | OSi(C$_2$H$_5$)$_3$ | 2 | S—⌬ | 2 | CO$_2$Na | 16 |
| 65 | Si | 9,10-Phenanthrene ring | OSi(C$_4$H$_9$)$_3$ | 2 | S—⌬ | 1 | SO$_3$Na | 6 |
| 66 | Si | 9,10-Phenanthrene ring | OSi(C$_4$H$_9$)$_3$ | 2 | S—⌬ | 1 | SO$_3$Na | 8 |
| 67 | Si | 9,10-Phenanthrene ring | OSi(C$_4$H$_9$)$_3$ | 2 | S—⌬ | 1 | OPO$_3$Na | 8 |
| 68 | Si | 9,10-Phenanthrene ring | O—⌬(COONa)(COONa) | 2 | S—⌬ | 1 | CO$_2$Na | 8 |
| 69 | Si | 9,10-Phenanthrene ring | S—⌬(COONa)(COONa) | 2 | S—⌬ | 1 | CO$_2$Na | 8 |
| 70 | Si | 9,10-Phenanthrene ring | O—⌬(COONa)(COONa) | 2 | S—⌬ | 2 | CO$_2$Na | 16 |

TABLE 4-continued

| Illustrative compd. No. | M | A | Y | p | XQ | m | EZ | 4n |
|---|---|---|---|---|---|---|---|---|
| 71 | Si | 9,10-Phenanthrene ring | O-C(CH₂OH)₃ (trishydroxymethyl, O-linked) | 2 | S-C₆H₅ | 2 | CO₂Na | 8 |
| 72 | Si | 9,10-Phenanthrene ring | O-C(COONa)₃ | 2 | S-C₆H₅ | 1 | CO₂Na | 8 |
| 73 | Si | 9,10-Phenanthrene ring | OH | 2 | S-C₆H₅ | 1 | SO₃-C(COONa)₃ | 8 |
| 74 | Si | 9,10-Phenanthrene ring | O-C₆H₃(COONa)₂ | 2 | S-C₆H₅ | 2 | SO₃-C(COONa)₃ | 16 |
| 75 | Si | 9,10-Phenanthrene ring | OPO₃Na | 2 | O-C₆H₅ | 2 | CO₂Na | 16 |
| 76 | Si | 9,10-Phenanthrene ring | NH.CO-C₆H₃(COONa)₂ | 2 | O- | 1 | CO₂Na | 12 |
| 77 | Al | 9,10-Phenanthrene ring | OH | 1 | S-C₆H₅ | 2 | CO₂Na | 16 |
| 78 | Zn | 9,10-Phenanthrene ring | — | 0 | S-C₆H₅ | 2 | CO₂Na | 16 |
| 79 | Ge | 9,10-Phenanthrene ring | OH | 2 | S-C₆H₅ | 2 | CO₂Na | 16 |
| 80 | H₂ | 9,10-Phenanthrene ring | — | 0 | S-C₆H₅ | 2 | CO₂Na | 16 |

TABLE 5

| Illustrative compd. No. | M | A | Y | p | XQ | m | EZ | 4n |
|---|---|---|---|---|---|---|---|---|
| 81 | Si | 2,3-Anthracene ring | OSi(C₄H₉)₃ | 2 | S-C₆H₅ | 1 | CO₂Na | 8 |

TABLE 5-continued

| Illustrative compd. No. | M | A | Y | p | XQ | m | EZ | 4n |
|---|---|---|---|---|---|---|---|---|
| 82 | Si | 2,3-Anthracene ring | OSi(C$_4$H$_9$)$_3$ | 2 | S—phenyl | 2 | CO$_2$Na | 16 |
| 83 | Si | 2,3-Anthracene ring | OSi(C$_2$H$_5$)$_3$ | 2 | S—phenyl | 1 | CO$_2$Na | 8 |
| 84 | Si | 2,3-Anthracene ring | OSi(C$_2$H$_5$)$_3$ | 2 | S—phenyl | 2 | CO$_2$Na | 16 |
| 85 | Si | 2,3-Anthracene ring | OSi(C$_4$H$_9$)$_3$ | 2 | S—phenyl | 1 | SO$_3$Na | 6 |
| 86 | Si | 2,3-Anthracene ring | OSi(C$_4$H$_9$)$_3$ | 2 | S—phenyl | 1 | SO$_3$Na | 8 |
| 87 | Si | 2,3-Anthracene ring | OSi(C$_4$H$_9$)$_3$ | 2 | S—phenyl | 1 | OPO$_3$Na | 8 |
| 88 | Si | 2,3-Anthracene ring | O—phenyl(COONa)(COONa) | 2 | S—phenyl | 1 | CO$_2$Na | 8 |
| 89 | Si | 2,3-Anthracene ring | S—phenyl(COONa)(COONa) | 2 | S—phenyl | 1 | CO$_2$Na | 8 |
| 90 | Si | 2,3-Anthracene ring | O—phenyl(COONa)(COONa) | 2 | S—phenyl | 2 | CO$_2$Na | 16 |
| 91 | Si | 2,3-Anthracene ring | O—C(CH$_2$OH)$_3$ | 2 | S—phenyl | 2 | CO$_2$Na | 16 |
| 92 | Si | 2,3-Anthracene ring | O—C(COONa)$_3$ | 2 | S—phenyl | 1 | CO$_2$Na | 8 |
| 93 | Si | 2,3-Anthracene ring | OH | 2 | S—phenyl | 1 | SO$_3$—C(COONa)$_3$ | 8 |

TABLE 5-continued

| Illustrative compd. No. | M | A | Y | p | XQ | m | EZ | 4n |
|---|---|---|---|---|---|---|---|---|
| 94 | Si | 2,3-Anthracene ring | 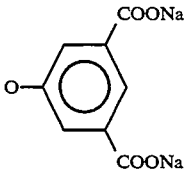 | 2 | 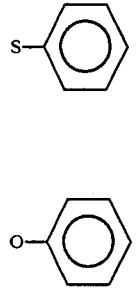 | 2 | $CO_2Na$ | 16 |
| 95 | Si | 2,3-Anthracene ring | $OPO_3Na$ | 2 | 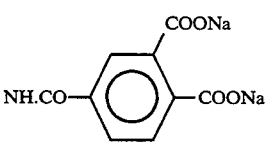 | 2 | $CO_2Na$ | 16 |
| 96 | Si | 2,3-Anthracene ring | 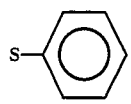 | 2 | 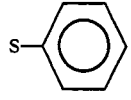 | 1 | $CO_2Na$ | 12 |
| 97 | Al | 2,3-Anthracene ring | OH | 1 | 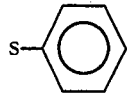 | 2 | $CO_2Na$ | 16 |
| 98 | Zn | 2,3-Anthracene ring | — | 0 | 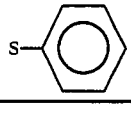 | 2 | $CO_2Na$ | 16 |
| 99 | Ge | 2,3-Anthracene ring | OH | 2 | 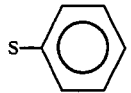 | 2 | $CO_2Na$ | 16 |
| 100 | $H_2$ | 2,3-Anthracene ring | — | 0 | 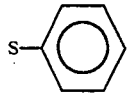 | 2 | $CO_2Na$ | 16 |

TABLE 6

| Illustrative compd. No. | M | A | Y | p | XQ | m | EZ | 4n |
|---|---|---|---|---|---|---|---|---|
| 101 | Si | 1,2-Naphthalene ring | $OSi(C_4H_9)_3$ | 2 | 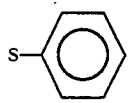 | 1 | $CO_2Na$ | 8 |
| 102 | Si | 1,2-Naphthalene ring | $OSi(C_4H_9)_3$ | 2 | 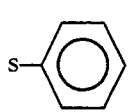 | 2 | $CO_2Na$ | 16 |
| 103 | Si | 1,2-Naphthalene ring | $OSi(C_2H_5)_3$ | 2 | 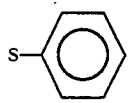 | 1 | $CO_2Na$ | 8 |
| 104 | Si | 1,2-Naphthalene ring | $OSi(C_2H_5)_3$ | 2 | 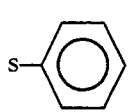 | 2 | $CO_2Na$ | 16 |

TABLE 6-continued

| Illustrative compd. No. | M | A | Y | p | XQ | m | EZ | 4n |
|---|---|---|---|---|---|---|---|---|
| 105 | Si | 1,2-Naphthalene ring | OSi(C$_4$H$_9$)$_3$ | 2 | 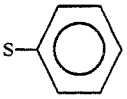 | 1 | SO$_3$Na | 6 |
| 106 | Si | 1,2-Naphthalene ring | OSi(C$_4$H$_9$)$_3$ | 2 | 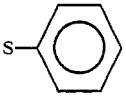 | 1 | SO$_3$Na | 8 |
| 107 | Si | 1,2-Naphthalene ring | OSi(C$_4$H$_9$)$_3$ | 2 | 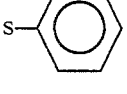 | 1 | OPO$_3$Na | 8 |
| 108 | Si | 1,2-Naphthalene ring | 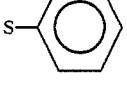 | 2 | 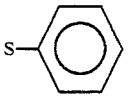 | 1 | CO$_2$Na | 8 |
| 109 | Si | 1,2-Naphthalene ring | 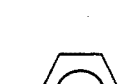 | 2 | 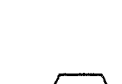 | 1 | CO$_2$Na | 8 |
| 110 | Si | 1,2-Naphthalene ring | 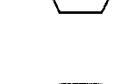 | 2 |  | 2 | CO$_2$Na | 16 |
| 111 | Si | 1,2-Naphthalene ring | 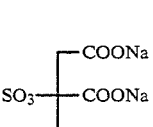 | 2 | 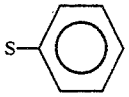 | 2 | CO$_2$Na | 16 |
| 112 | Si | 1,2-Naphthalene ring | O—C(COONa)$_3$ | 2 | 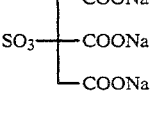 | 1 | CO$_2$Na | 8 |
| 113 | Si | 1,2-Naphthalene ring | OH | 2 | 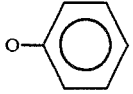 | 1 | SO$_3$—C(COONa)$_3$ | 8 |
| 114 | Si | 1,2-Naphthalene ring | (see structure) | 2 | (see structure) | 2 | SO$_3$—C(COONa)$_3$ | 16 |
| 115 | Si | 1,2-Naphthalene ring | OPO$_3$Na | 2 | (see structure) | 2 | CO$_2$Na | 16 |

TABLE 6-continued

| Illustrative compd. No. | M | A | Y | p | XQ | m | EZ | 4n |
|---|---|---|---|---|---|---|---|---|
| 116 | Si | 1,2-Naphthalene ring | NH.CO—⟨ring⟩—COONa, COONa | 2 | O—[ | 1 | CO$_2$Na | 12 |
| 117 | Al | 1,2-Naphthalene ring | OH | 1 | S—⟨ring⟩ | 2 | CO$_2$Na | 16 |
| 118 | Zn | 1,2-Naphthalene ring | — | 0 | S—⟨ring⟩ | 2 | CO$_2$Na | 16 |
| 119 | Ge | 1,2-Naphthalene ring | OSi(C$_4$H$_9$)$_3$ | 2 | S—⟨ring⟩ | 2 | CO$_2$Na | 16 |
| 120 | H$_2$ | 1,2-Naphthalene ring | — | 0 | S—⟨ring⟩ | 2 | CO$_2$Na | 16 |

The water-soluble tetraazaporphin of the formula (I) can be synthesized by various methods. For example, the synthesis can be carried out by the following routes:

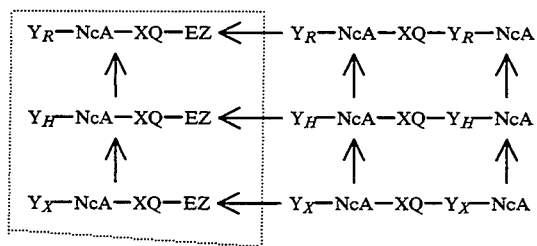

In the above formulae, NcA means the portion except for —Yp, —(EZ)$_n$ and XQ in the formula (I); Y$_R$—NcA—XQ—EZ is a compound of the formula (I) wherein Y is —OR$^1$, —NR$_2^2$ or —SR$^3$ (except for R=H), and XQ and EZ are present; Y$_H$—NcA—XQ—EZ is a compound of the formula (I) wherein Y is —OH, —NH$_2$ or —SH, and XQ and EZ are present; Y$_X$—NcA—XQ—EZ is a compound of the formula (I) wherein Y is a halogen atom, and XQ and EZ are present; Y$_R$—NcA—XQ is a compound of the formula (I) wherein Y is —OR$^1$, —NR$_2^2$, —SR$^3$ (except for R=H), and XQ is present, said compound being able to have a substituent which can be introduced into EZ by hydrolysis on a fused polycyclic aromatic ring of NcA or XQ; Y$_H$—NcA—XQ is a compound of the formula (I) wherein Y is —OH, —NH$_2$ or —SH and XQ is present, said compound being able to have a substituent which can be introduced into EZ by hydrolysis on a fused polycyclic aromatic ring of NcA or XQ; Y$_X$—NcA—XQ is a compound of the formula (I) wherein Y is a halogen atom and XQ is present, said compound being able to have a substituent which can be introduced into EZ by hydrolysis on a fused polycyclic aromatic ring of NcA or XQ; Y$_R$—NcA is a compound of the formula (I) wherein Y is —OR$^1$, —NR$_2^2$ or —SR$^3$ (except for R=H), said compound being able to have a leaving group which can be substituted with XQ; Y$_H$—Nc is a compound of the formula (I) wherein Y is —OH, —NH$_2$ or —SH, said compound being able to have a leaving group which can be substituted with XQ; and Y$_X$—NcA is a compound of the formula (I) wherein Y is a halogen atom, said compound being able to have a leaving group which can be substituted with XQ.

The reactions of individual compounds in the above-mentioned routes are well known, but dependent on structures to be introduced. Further, preferable routes are dependent on the desired final products. The reaction from the lowest compounds to upper compounds in the above-mentioned reactioon routes, that is, the substitution from Y$_X$ to Y$_H$, can be carried out by hydrolysis (in the case of Y$_H$=—OH), ammonolysis (in the case of Y$_H$=—NH$_2$), etc. Further, the substitution from Y$_H$ to Y$_R$ can be carried out by reacting with a corresponding alcohol, acylchloride, silanol, chlorosilane, chlorophosphine, chlorophosphite, phosphoryl chloride, or the like.

Further, in the above-mentioned reaction routes, the change of compounds from a right-hand side to a left-hand side, that is, the introduction of XQ and EZ, can be carried out by reacting with a compound having the desired XQ and/or EZ or having a moiety which can be changed to XQ or EZ by one step or a plurality of steps.

In the above-mentioned formulae, those encircled by a dotted line belong to the compounds of the formula (I).

The compounds represented by Y$_X$—NcA—XQ—EZ, Y$_X$—NcA—XQ and Y$_X$—NcA mentioned above can be synthesized from a corresponding dicyano aromatic compounds or isoindoline derivatives according to the methods described in references [Zh. Obshch. Khim., 39, 2554–2558 (1969), J. Am. Chem.

Soc., 106, 7404–7410 (1984), Zh. Obshch. Khim., 39, 2536–2541 (1969), Chem. Ber., 121, 1479–1486 (1988), Synthetic Metals, 9, 329–340 (1984), etc.].

As the fluorochrome for labeling of this invention, there can be used not only all of novel tetraazaporphin derivatives of the general formula (I) but also some of water-soluble tetraazaporphins proposed for other application purposed [U.S. Pat. No. 4,657,554, Japanese Patent Unexamined Publication Nos. SHO 57 (1982)-210000, SHO 60 (1985)-199890, HEI 1(1989)-130978, HEI 1(1989)-198391, etc.]. Compounds usable as the fluorochrome for labeling of this invention which include the usable water-soluble tetraazaporphins are represented by the above general formula (II).

In the compound of the general formula (II) of this invention, $R^1$, $R^2$ and $R^3$ have the same meanings as defined in the general formula (I). Specific examples of the hydrocarbon group represented by Q are the same as those given in the case of the general formula (I). In addition, p and EZ also have the same meanings as defined in the general formula (I). Also, the compound of the general formula (II) can be synthesized by various routes, for example, the same synthesis routes of the general formula (I) mentioned above.

A most important characteristic required of a compound used as the fluorochrome for labeling is that the compound shows a high fluorescence quantum yield (>0.1). For showing such a high fluorescence quantum yield, a tetraazaporphin derivative should satisfy the following conditions: the central metal should not be a heavy metal or a transition metal, and the tetraazaporphin derivative should be in a monomolecular state in a solution.

For satisfying these conditions, $H_2$, Mg, Al, Si, P, Zn, Ga, Ge or Sc is used as the central metal M. In particular, it is most preferable to make it possible to maintain the monomolecular state in a solution by suppressing the formation of face-to-face H-aggregates between molecules which is characteristic of tetraazaporphins, by any of the following two methods: there is used a compound containing a tetravalent metal (Si or Ge) as the central metal and having two substituents Y on M above and below a tetraazaporphin ring; or a substituent capable of causing serious steric hindrance is introduced into a tetraazaporphin ring. For realizing the monomolecular state in an aqueous solution, it is preferable to place a surfactant together with the fluorochrome for labeling. The concentration of the surfactant is preferably 0.01 to 5%, more preferably 0.04 to 2%.

The surfactant includes ionic surfactants and nonionic surfactants. Of these, nonionic surfactants such as Triton X-100, Tween series surfactants, Brij series surfactants, etc. are particularly preferable.

A tetraazaporphin which assumes a monomolecular state in the aqueous solution thus obtained shows a high fluorescence quantum yield (>0.1) sufficient to permit application of the tetraazaporphin to fluorochrome for labeling.

It is particularly preferable to use the novel tetraazaporphin of the general formula (I) because it is highly soluble particularly in water and polar organic solvents, is easy to separate and purify in its synthesis, and shows a high fluorescence quantum yield (>0.29).

As tetraazaporphins applied to the fluorochrome for labeling of this invention, there can be used not only the novel tetraazaporphins of the general formula (I) listed in Tables 1 to 6, but also for example, the tetraazaporphins listed in Tables 7 to 9 which are represented by the general formula (II).

TABLE 7

| Illustrative compd. No. | M | A | Y | p | XQ | Q | m | EZ | 4n |
|---|---|---|---|---|---|---|---|---|---|
| 121 | Si | 2,3-Naphthalene ring | OSi(C$_2$H$_5$)$_3$ | 2 | — | | 0 | CO$_2$Na | 4 |
| 122 | Si | 2,3-Naphthalene ring | OSi(CH$_3$)$_3$ | 2 | — | | 0 | SO$_3$Na | 3 |
| 123 | Si | 2,3-Naphthalene ring | OSi(CH$_2$H$_5$)$_3$ | 2 | — | | 0 | SO$_3$Na | 3 |
| 124 | Si | 2,3-Naphthalene ring | OC$_4$H$_9$ | 2 | — | | 0 | SO$_3$Na | 3 |
| 125 | Si | 2,3-Naphthalene ring | OH | 2 | — | | 0 | SO$_3$Na | 3 |
| 126 | Zn | 2,3-Naphthalene ring | — | 0 | — | | 0 | CO$_2$Na | 4 |
| 127 | Zn | 2,3-Naphthalene ring | — | 0 | — | | 0 | SO$_3$Na | 3 |
| 128 | Al | 2,3-Naphthalene ring | Cl | 1 | — | | 0 | SO$_3$Na | 3 |
| 129 | Al | 2,3-Naphthalene ring | Cl | 1 | — | | 1 | CO$_2$Na | 4 |
| 130 | Ge | 2,3-Naphthalene ring | NH.CO–⟨phenyl with COONa, COONa⟩ | 2 | — | | 1 | CO$_2$Na | 8 |
| 131 | Si | 2,3-Quinoline ring | OSi(C$_2$H$_5$)$_3$ | 2 | — | | 0 | CO$_2$Na | 8 |
| 132 | Si | 2,3-Quinoline ring | OSi(C$_4$H$_9$)$_3$ | 2 | — | | 0 | SO$_3$Na | 3 |
| 133 | Si | 2,3-Quinoline ring | OSO$_3$Na | 2 | — | | 0 | SO$_3$Na | 3 |
| 134 | Si | 2,3-Quinoline ring | OSO$_3$Na | 2 | — | | 0 | SO$_3$–⟨phenyl with COONa, COONa, COONa⟩ | 3 |
| 135 | Si | 2,3-Quinoline ring | OH | 2 | ⟨phenyl⟩ | | 1 | SO$_3$Na | 6 |

TABLE 7-continued

| Illustrative compd. No. | M | A | Y | p | XQ | Q | m | EZ | 4n |
|---|---|---|---|---|---|---|---|---|---|
| 136 | $H_2$ | 2,3-Quinoline ring | — | 0 | | CO—⟨Ph⟩ | 1 | $CO_2Na$ | 8 |
| 137 | Zn | 2,3-Quinoline ring | — | 0 | — | | 0 | $SO_3Na$ | 3 |
| 138 | Al | 2,3-Quinoline ring | Cl | 1 | — | | 0 | $SO_3Na$ | 3 |
| 139 | Ga | 2,3-Quinoline ring | Cl | 1 | | NH.CO—⟨Ph⟩ | 2 | $CO_2Na$ | 16 |
| 140 | Ge | 2,3-Quinoline ring | NH.CO—⟨Ph(COONa)(COONa)⟩ | 2 | | NH.CO—⟨Ph⟩ | 1 | $CO_2Na$ | 8 |

TABLE 8

| Illustrative compd. No. | M | A | Y | p | XQ | m | EZ | 4n |
|---|---|---|---|---|---|---|---|---|
| 141 | Si | 2,3-Quinoxaline ring | $OSi(C_4H_9)_3$ | 2 | — | 0 | $CO_2Na$ | 4 |
| 142 | Si | 2,3-Quinoxaline ring | $OSi(C_2H_5)_3$ | 2 | — | 0 | $SO_3Na$ | 3 |
| 143 | Si | 2,3-Quinoxaline ring | $OSO_3Na$ | 2 | — | 0 | $SO_3Na$ | 3 |
| 144 | Si | 2,3-Quinoxaline ring | $OSO_3Na$ | 2 | — | 0 | $SO_3$—⟨C(COONa)_3⟩ | 3 |
| 145 | Si | 2,3-Quinoxaline ring | OH | 2 | | 1 | $SO_3Na$ | 6 |
| 146 | Zn | 2,3-Quinoxaline ring | — | 0 | — | 0 | $CO_2Na$ | 4 |
| 147 | Zn | 2,3-Quinoxaline ring | — | 0 | — | 0 | $SO_3Na$ | 3 |
| 148 | Al | 2,3-Quinoxaline ring | Cl | 1 | — | 0 | $SO_3Na$ | 3 |
| 149 | Al | 2,3-Quinoxaline ring | Cl | 1 | — | 0 | $CO_2Na$ | 4 |
| 150 | Ge | 2,3-Quinoxaline ring | NH.CO—⟨Ph(COONa)_2⟩ | 2 | | 1 | $CO_2Na$ | 8 |
| 151 | Si | 9,10-Phenanthrene ring | $OSi(C_2H_5)_3$ | 2 | — | 0 | $CO_2Na$ | 8 |
| 152 | Si | 9,10-Phenanthrene ring | $OSi(C_6H_5)_3$ | 2 | — | 0 | $SO_3Na$ | 3 |
| 153 | Si | 9,10-Phenanthrene ring | $OSO_3Na$ | 2 | — | 0 | $SO_3Na$ | 3 |
| 154 | Si | 9,10-Phenanthrene ring | $OC_{10}H_{21}$ | 2 | $CO.C_4H_8$ | 2 | $CO_2Na$ | 8 |
| 155 | Si | 9,10-Phenanthrene ring | OH | 2 | | 1 | $SO_3Na$ | 6 |
| 156 | $H_2$ | 9,10-Phenanthrene ring | — | 0 | — | 0 | $SO_3Na$ | 8 |
| 157 | Zn | 9,10-Phenanthrene ring | — | 0 | $CO.C_2H_4$ | 2 | $CO_2Na$ | 8 |
| 158 | Al | 9,10-Phenanthrene ring | O—⟨Ph(CO_2Na)_2⟩ | 1 | $OSO_2$—⟨Ph⟩ | 1 | $CO_2Na$ | 8 |

TABLE 8-continued

| Illustrative compd. No. | M | A | Y | p | XQ | m | EZ | 4n |
|---|---|---|---|---|---|---|---|---|
| 159 | Ga | 9,10-Phenanthrene ring | 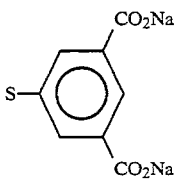 S—C₆H₃(CO₂Na)₂ | 1 | 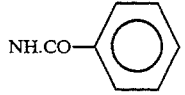 NH.CO—C₆H₅ | 2 | CO₂Na | 16 |
| 160 | Ge | 9,10-Phenanthrene ring | 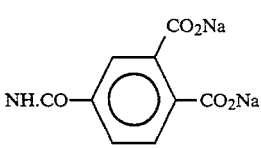 NH.CO—C₆H₃(CO₂Na)₂ | 2 | 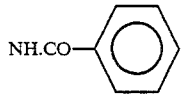 NH.CO—C₆H₅ | 1 | CO₂Na | 8 |

TABLE 9

| Illustrative compd. No. | M | A | Y | p | XQ | m | EZ | 4n |
|---|---|---|---|---|---|---|---|---|
| 161 | Si | 2,3-Anthracene ring | OSi(C₆H₁₃)₃ | 2 | — | 0 | CO₂Na | 4 |
| 162 | P | 2,3-Anthracene ring | OSi(C₄H₉)₃ | 2 | — | 0 | SO₃Na | 3 |
| 163 | Si | 2,3-Anthracene ring | OSO₃Na | 2 | — | 0 | SO₃Na | 3 |
| 164 | Si | 2,3-Anthracene ring | OSO₃Na | 2 | — | 0 | 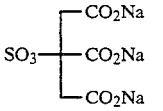 SO₃—C(CO₂Na)₃ | 3 |
| 165 | Si | 2,3-Anthracene ring | OH | 2 | 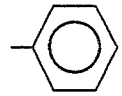 C₆H₅ | 2 | SO₃Na | 6 |
| 166 | H₂ | 2,3-Anthracene ring | — | 0 | 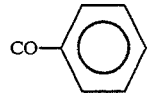 CO—C₆H₅ | 1 | CO₂Na | 8 |
| 167 | Zn | 2,3-Anthracene ring | — | 0 | 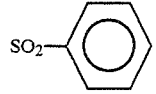 SO₂—C₆H₅ | 2 | CO₂Na | 16 |
| 168 | Al | 2,3-Anthracene ring | 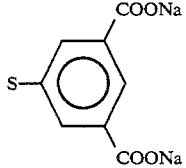 S—C₆H₃(COONa)₂ | 1 | 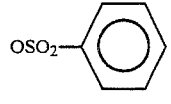 OSO₂—C₆H₅ | 1 | CO₂Na | 8 |
| 169 | Ga | 2,3-Anthracene ring | 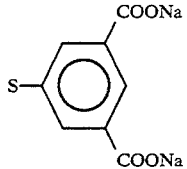 S—C₆H₃(COONa)₂ | 1 | 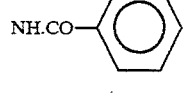 NH.CO—C₆H₅ | 2 | CO₂Na | 16 |
| 170 | Ge | 2,3-Anthracene ring | 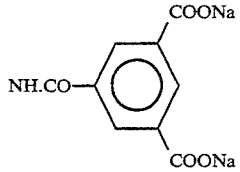 NH.CO—C₆H₃(COONa)₂ | 2 | 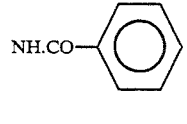 NH.CO—C₆H₅ | 1 | CO₂Na | 8 |
| 171 | Si | 1,2-Naphthalene ring | OSi(C₄H₉)₃ | 2 | — | 0 | CO₂Na | 4 |
| 172 | Si | 1,2-Naphthalene ring | OSi(CH₃)₃ | 2 | — | 0 | CO₂Na | 4 |

TABLE 9-continued

| Illustrative compd. No. | M | A | Y | p | XQ | m | EZ | 4n |
|---|---|---|---|---|---|---|---|---|
| 173 | Si | 1,2-Naphthalene ring | OSO$_3$Na | 2 | — | 0 | SO$_3$Na | 3 |
| 174 | Si | 1,2-Naphthalene ring | OC$_6$H$_{13}$ | 2 | CO.C$_4$H$_8$ | 1 | CO$_2$Na | 4 |
| 175 | Si | 1,2-Naphthalene ring | OH | 2 | —⟨phenyl⟩ | 1 | SO$_3$Na | 6 |
| 176 | H$_2$ | 1,2-Naphthalene ring | — | 0 | — | 0 | SO$_3$Na | 4 |
| 177 | Zn | 1,2-Naphthalene ring | — | 0 | SO$_2$—⟨phenyl⟩ | 2 | CO$_2$Na | 8 |
| 178 | Al | 1,2-Naphthalene ring | OH | 1 | CO.C$_2$H$_4$ | 1 | CO$_2$Na | 4 |
| 179 | Ga | 1,2-Naphthalene ring | OH | 1 | NH.CO—⟨phenyl⟩ | 2 | CO$_2$Na | 16 |
| 180 | Ge | 1,2-Naphthalene ring | NH.CO—⟨phenyl with COONa, COONa⟩ | 2 | NH.CO—⟨phenyl⟩ | 1 | CO$_2$Na | 8 |

The above-mentioned fluorochrome for labeling can be made into a reagent for various analyses. As described above, the reagent preferably contains a nonionic surfactant, depending on the kind of the fluorochrome.

In practice, said fluorochrome for labeling is made into a reagent by attaching the same to any of various substances, depending on the purpose of analysis. When the fluorochrome is used for immunoassay, the substances are various antigens (including haptens and drugs) and antibodies. When the fluorochrome is used for analyzing the nucleotide sequence of DNA or when it is used for analysis in the form of a DNA probe, the substance is the DNA, i.e., nucleotide.

The fluorochrome is often used particularly as a fluorescent label for substances derived from organisms, for example, in the above analyses.

The substance derived from an organism which can be labeled with the aforesaid fluorochrome for labeling and is used in this invention, includes proteins (peptides), nucleotides, sugars, lipids, hormones, vitamins, alkaloids, antibiotics, complexes thereof, etc. which are obtained from organisms such as animals, plants, microorganisms (including viruses), etc. These substances may be any of those extracted from natural sources, artificial and completely synthetic ones, and artificial and semisynthetic ones.

Specific examples of the proteins (peptides) are serum albumin, immunoglobulins (e.g. IgG, IgA, IgM, IgD and IgE), monoclonal antibodies against various proteins or membrane antigens of laucocyte, and enzymes (e.g. peroxidases, glucose oxidase and alkaline oxidases). Specific examples of the nucleotides are DNA, RNA, synthetic oligonucleotides, synthetic polynucleotides, ATP, CTP, GTP, TTP, UTP, dATP, dCTP, dGTP, dTTP, dUTP, ddATP, ddCTP, ddGTP, ddTTP, ddUTP, and derivatives thereof. Specific examples of the sugars are polysaccharides (e.g. glycogen, starch and mannan), oligosaccharides, and monosaccharides (e.g. glucose and mannose). The lipids includes phosphatidylcholine, phosphatidylethanolamine, fats, fatty acids, etc. The hormones include peptide hormones (e.g. insulin, growth hormone, oxytocin, varopressin, secretin, epidermal growth factor, gastrin, glucagon and calcitonin), steroid hormones (e.g. androgen, estrogen and hydrocortisone), catecholamines (e.g. adrenaline and noradrenaline), etc. The vitamins include various vitamins such as vitamin A, vitamins B$_1$, B$_2$, B$_6$ and B$_{12}$, biotin, folic acid, vitamin C, vitamin D, vitamin E, etc. The alkaloids include opium alkaloids (e.g. morphine), tropane alkaloids (e.g. atropine and scopolamine), indole alkaloids (e.g. vinblastine and vincristine), isoquinoline alkaloids (e.g. coptis root), etc. The antibiotics include penicillin, cephalosporin, kanamycin, erythromycin, chloramphenicol, etc.

The substance derived from an organism and the fluorochrome for labeling can be combined by linking a functional group (e.g. a phosphoric acid group, carboxylic acid group, amino group, hydroxyl group or thiol group) in the substance derived from an organism and a functional group (e.g. a carboxyl group or a sulfonic acid group) in the fluorochrome for labeling, directly to each other through an ionic bond or a covalent bond. Alternatively, the substance derived from an organism and the fluorochrome for labeling can be combined through a combination assistant group called a linker, for facilitating bond-forming reaction. The substance derived from an organism which has been labeled with the fluorochrome for labeling can be purified by conventional purifying means such as chromatography, recrystallization, etc.

The aforesaid linker should be a group having at least two functional groups because one or more bonds should be formed for each of the substance derived from an organism and the fluorochrome for labeling. For this purpose, there can be used diols, diamines, amino alcohols, dicarboxylic acids, dithiols, aminocarboxylic acids, hydroxycarboxylic acids, etc.

The fluorochrome for labeling and the reagent comprising the same of this invention can be used in various fluorescence analysis method.

In particular, of fluorochromes for labeling of the general formula (II), novel compounds of the general formula (I) absorb semiconductor laser beams (670 to 840 nm) efficiently to emit fluorescence, and hence are very useful for assay of various antigens, drugs, DNAs, etc. and analysis of the nucleotide sequence of DNA in which measurement is carried out using an inexpensive and compact semiconductor laser.

This invention is explained below with reference to Examples, which are not by way of limitation but by way of illustration.

Synthetic Example 1

Synthesis of 3,4-bis(dibromomethyl)bromobenzene]

To a solution of 37 g (0.2 mol) of 4-bromo-o-xylene (75%) (mfd. by Aldrich Chemical Co.) and 142.4 g (0.8 mol) of N-bromosuccinimide in 500 ml of carbon tetrachloride was added 1 g of benzoyl peroxide, and the resulting mixture was irradiated by a 100-W high pressure mercury arc lamp for 8 to 12 hours under reflux. After the mixture was allowed to cool, the white crystals precipitated were removed by filtration and the carbon tetrachloride solution, i.e., the mother liquor was concentrated under reduced pressure. The solid thus obtained was recrystallized from hexane/methylene chloride to obtain 64 g of 3,4-bis(dibromomethyl)-bromobenzene as colorless crystals. Physical properties of 3,4-bis(dibromomethyl)bromobenzene were as follows;

(1) Melting point: 108.5°–110.5°
(2) Elementary analysis values:

|  | C | H | Br |
|---|---|---|---|
| Calculated (%) | 19.19 | 1.01 | 79.80 |
| Found (%) | 19.12 | 0.88 | 79.84 |

(3) NMR spectrum values: CDCl$_3$ δ values 7.81 (1H, br-s) 7.57 (1H, d, J=8.54 Hz) 7.50 (1H, dd, J=8.54, 1.83 Hz) 7.06 (1H, s) 7.02 (1H, s)

(4) IR spectrum (KBr) is shown in FIG. 1.

Synthetic Example 2

[Synthesis of 6-bromo-2,3-dicyanonaphthalene]

To a solution of 100.2 g (0.2 mol) of 3,4-bis(dibromomethyl)bromobenzene and 27 g (0.346 mol) of fumaronitrile in 800 ml of anhydrous N,N-dimethylformamide was added 200 g (0.67 mol) of sodium iodide with sufficient stirring, and the resulting mixture was stirred under nitrogen at about 75° C. for about 7 hours. After completion of the reaction, the reaction mixture was poured onto about 4 kg of ice. Sodium hydrogensulfite was slowly added until the reddish-brown aqueous solution thus obtained turned light-yellow. Sodium hydrogensulfite was added in a slight excess and stirred for a while. The resulting mixture was allowed to stand overnight at room temperature. The light-yellow solid precipitated was filtered and sufficiently washed with water and then methanol. The light-yellow solid was recrystallized from acetone/ethanol to obtain 33 g of colorless needles. The crystals were confirmed to be 6-bromo-2,3-dicyanonaphthalene from the following analysis results:

(1) Melting point: 254.5°–255.5° C.
(2) Elementary analysis values:

|  | C | H | N | Br |
|---|---|---|---|---|
| Calculated (%) | 56.06 | 1.96 | 10.90 | 31.08 |
| Found (%) | 55.99 | 1.67 | 10.87 | 30.74 |

Figure 2:
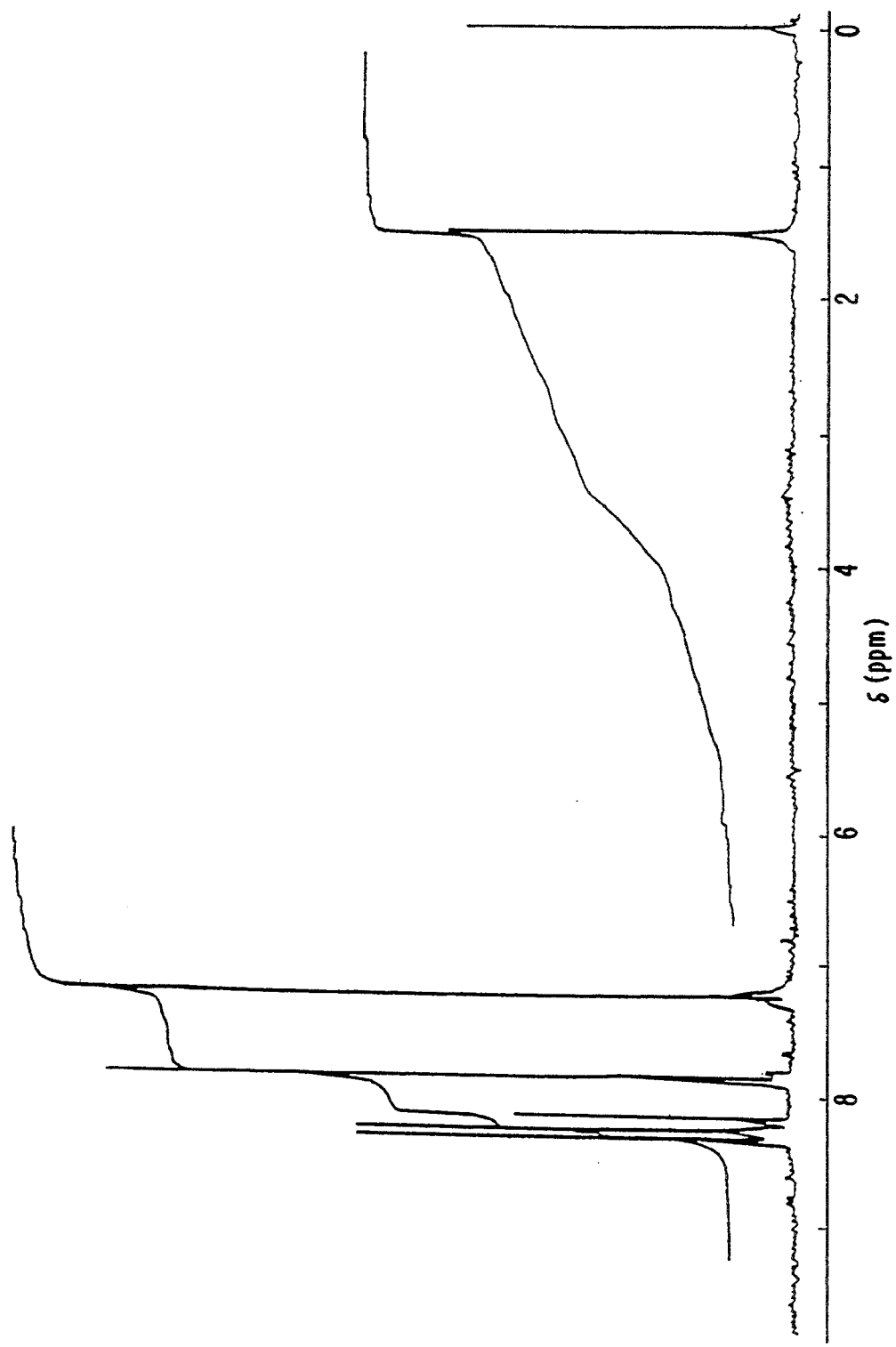
FIGS. 2, 9, 12, 15, 20, 23 and 26 show NMR spectra of compounds of this invention.

(3) NMR spectrum values: CDCl$_3$ (the NMR spectrum is shown in FIG. 2). δ values 8.34 (1H, s) 8.27 (1H, s) 8.17 (1H, br-s) 7.88 (2H, m)

Figure 3:
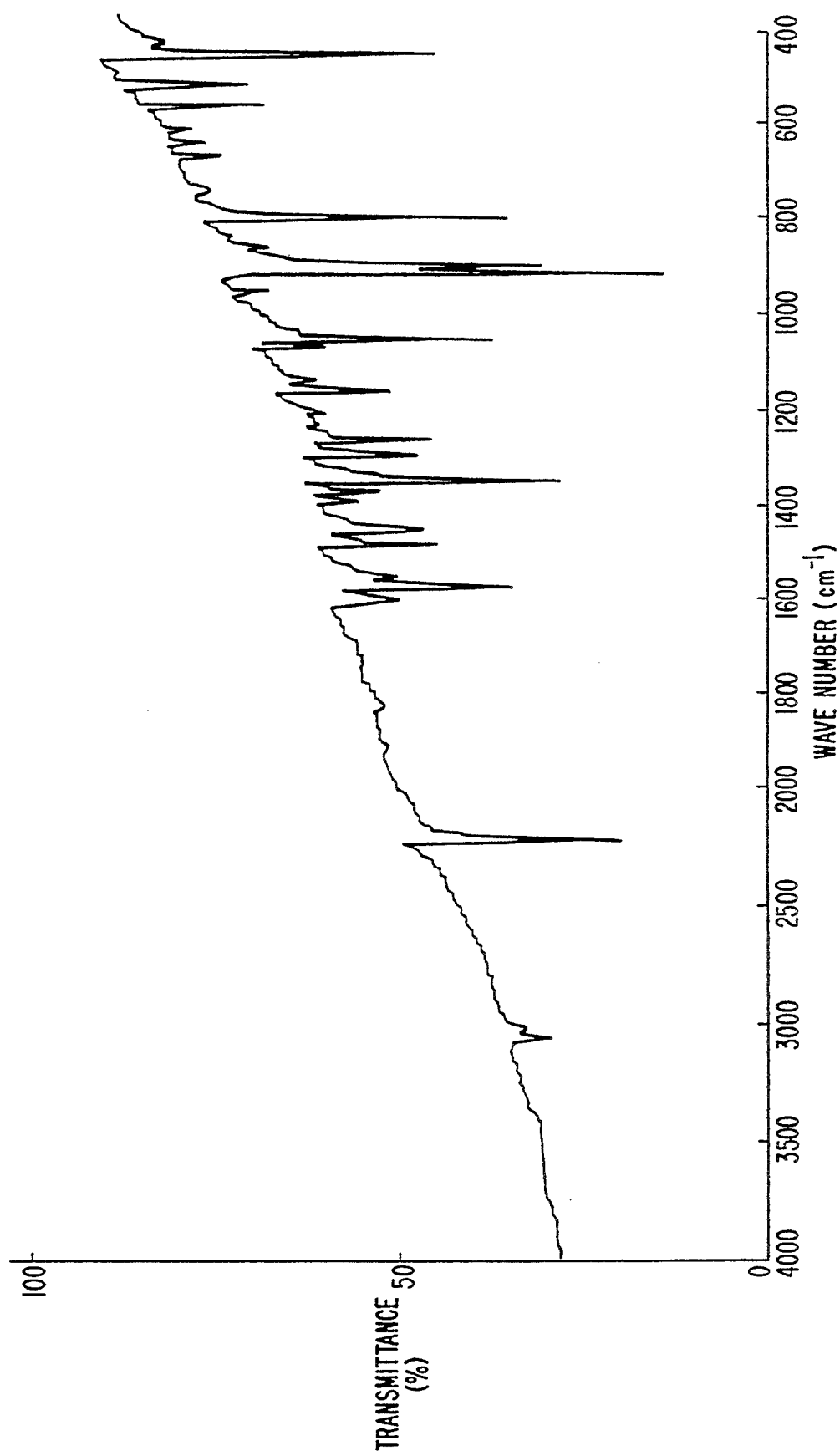

(4) IR spectrum (KBr) is shown in FIG. 3.

Synthetic Example 3

[Synthesis of 6-bromo-1,3-diiminobenz[f]isoindoline]

Figure 4:
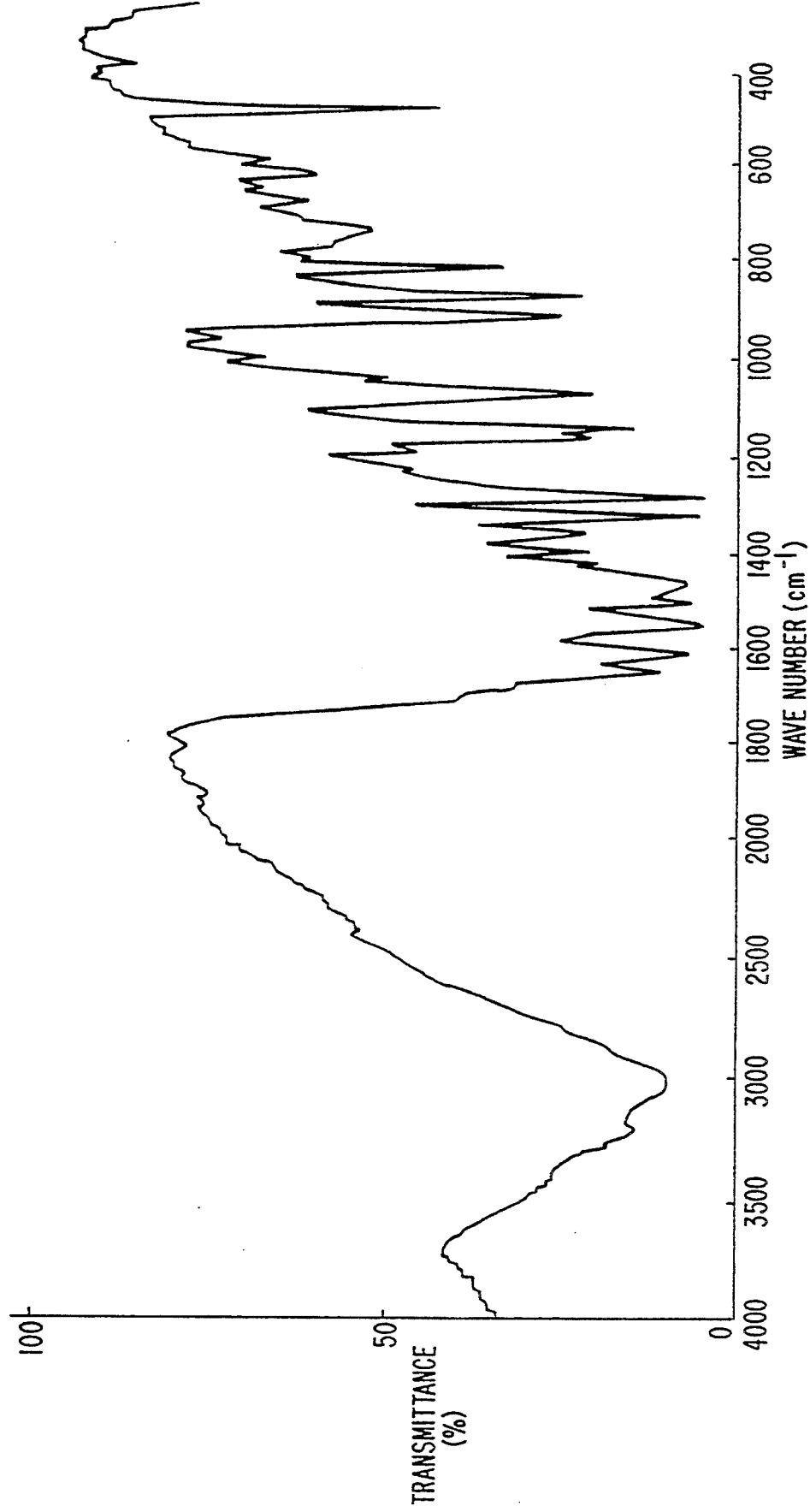

Under nitrogen, 44.1 g (0.17 mol) of 6-bromo-2,3-dicyanonaphthalene was added to a solution of sodium methoxide in methanol prepared by adding 1.92 g (84 mmols) of metallic sodium to 270 ml of absolute methanol in 5 times, and anhydrous ammonia gas was slowly bubbled into the resulting mixture with sufficient stirring at room temperature for about 1 hour. The mixture was refluxed for about 3 hours while bubbling therethrough anhydrous ammonia gas. After cooling, the yellow solid precipitated was filtered and the residue was sufficiently washed with methanol and dried under reduced pressure to obtain 45 g of 6-bromo-1,3-diiminobenz[f]isoindoline as a yellow solid. IR spectrum of this 6-bromo-1,3-diiminobenz[f]isoindoline is shown in FIG. 4. The 6-bromo-1,3-diiminobenz[f]isoindoline was used in the subsequent reaction without further purification.

Synthetic Example 4

[Synthesis of dichlorosilicon-tetrabromonaphthalocyanine]

Figure 5:
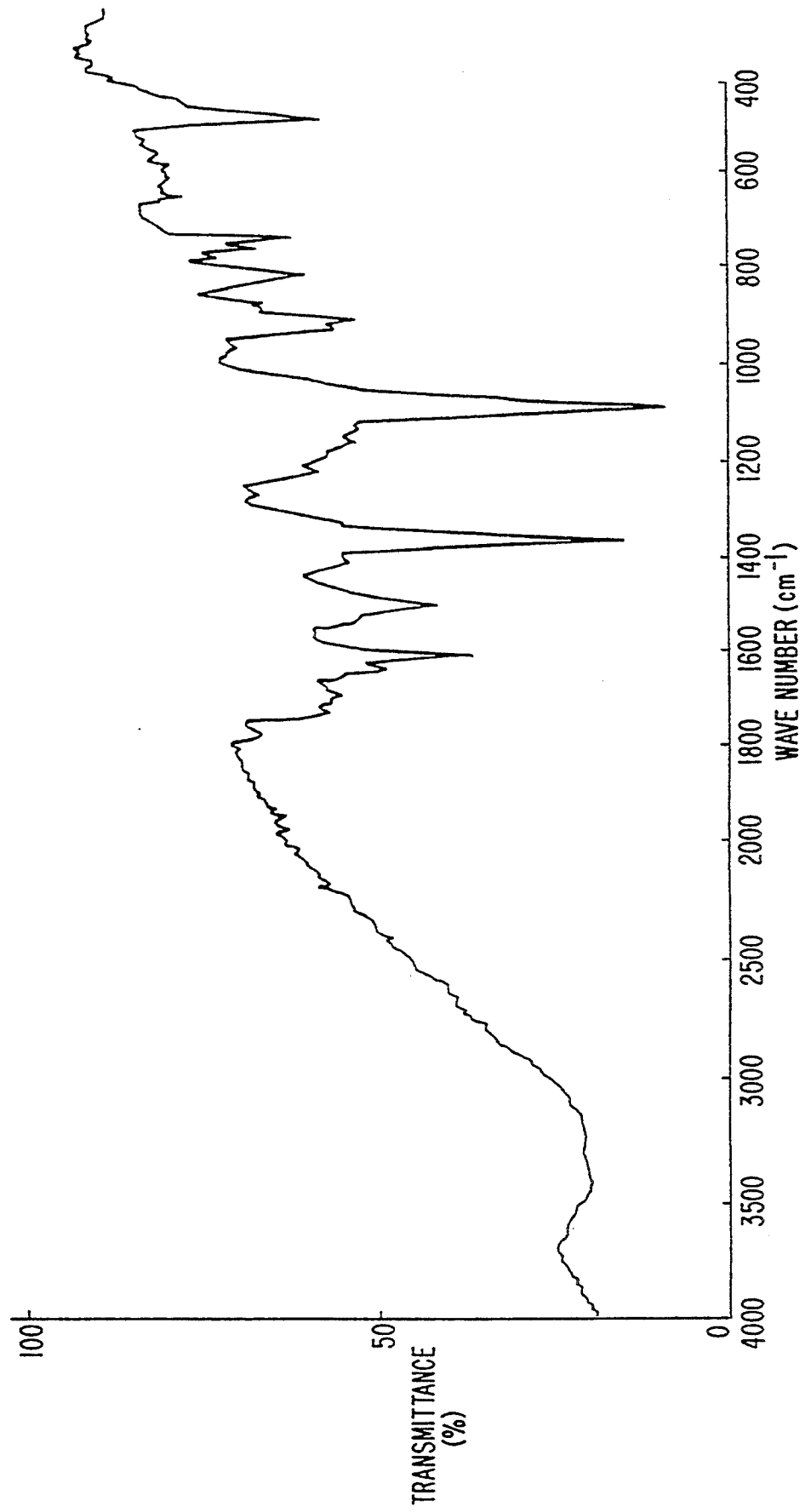
Figure 6:
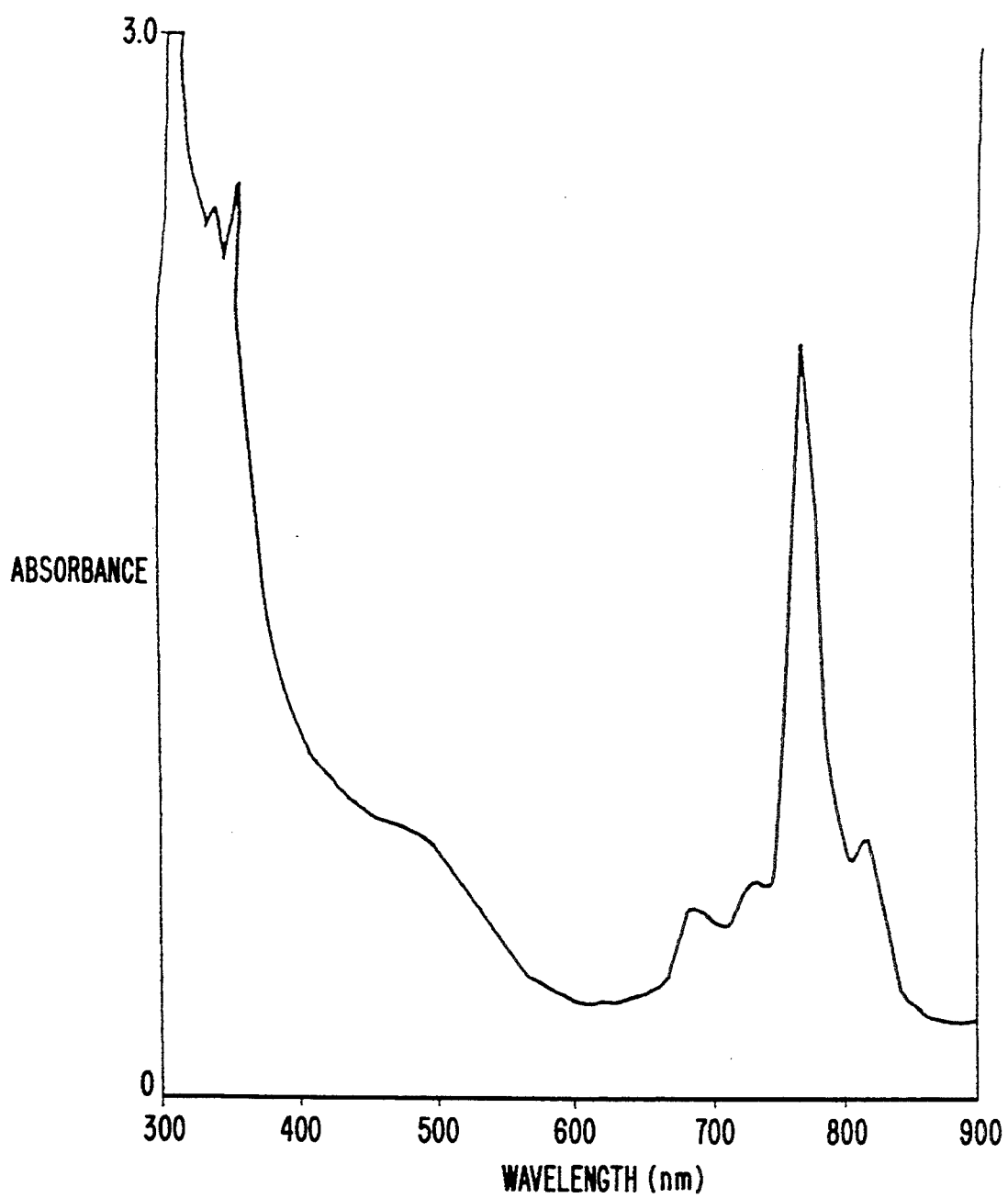
FIGS. 6 and 8 show electronic spectra (tetrahydrofuran solution) of compounds of this invention.

Under nitrogen, 54 ml of anhydrous tri-n-butylamine was added to a suspension of 22.5 g (81.8 mmols) of 6-bromo-1,3-diiminobenz[f]isoindoline in 110 ml of anhydrous tetralin, followed by adding thereto 14.4 ml (0.126 mol) of silicon tetrachloride, and the resulting mixture was refluxed for about 3 hours. After cooling, 700 ml of methanol was added and the resulting mixture was allowed to stand overnight. The reddish-brown reaction mixture was filtered and the residue was sufficiently washed with methanol and then dried under reduced pressure to obtain about 20 g of dichlorosilicon-tetrabromonaphthalocyanine as a dark-green solid. This dichlorosilicon-tetrabromonaphthalocyanine was used in the subsequent reaction without further purification. IR spectrum of dichlorosilicon-tetrabromonaphthalocyanine is shown in FIG. 5. Its electronic spectrum is shown in FIG. 6.

Synthetic Example 5

[Synthesis of dihydroxysilicon-tetrabromonaphthalocyanine]

Figure 7:
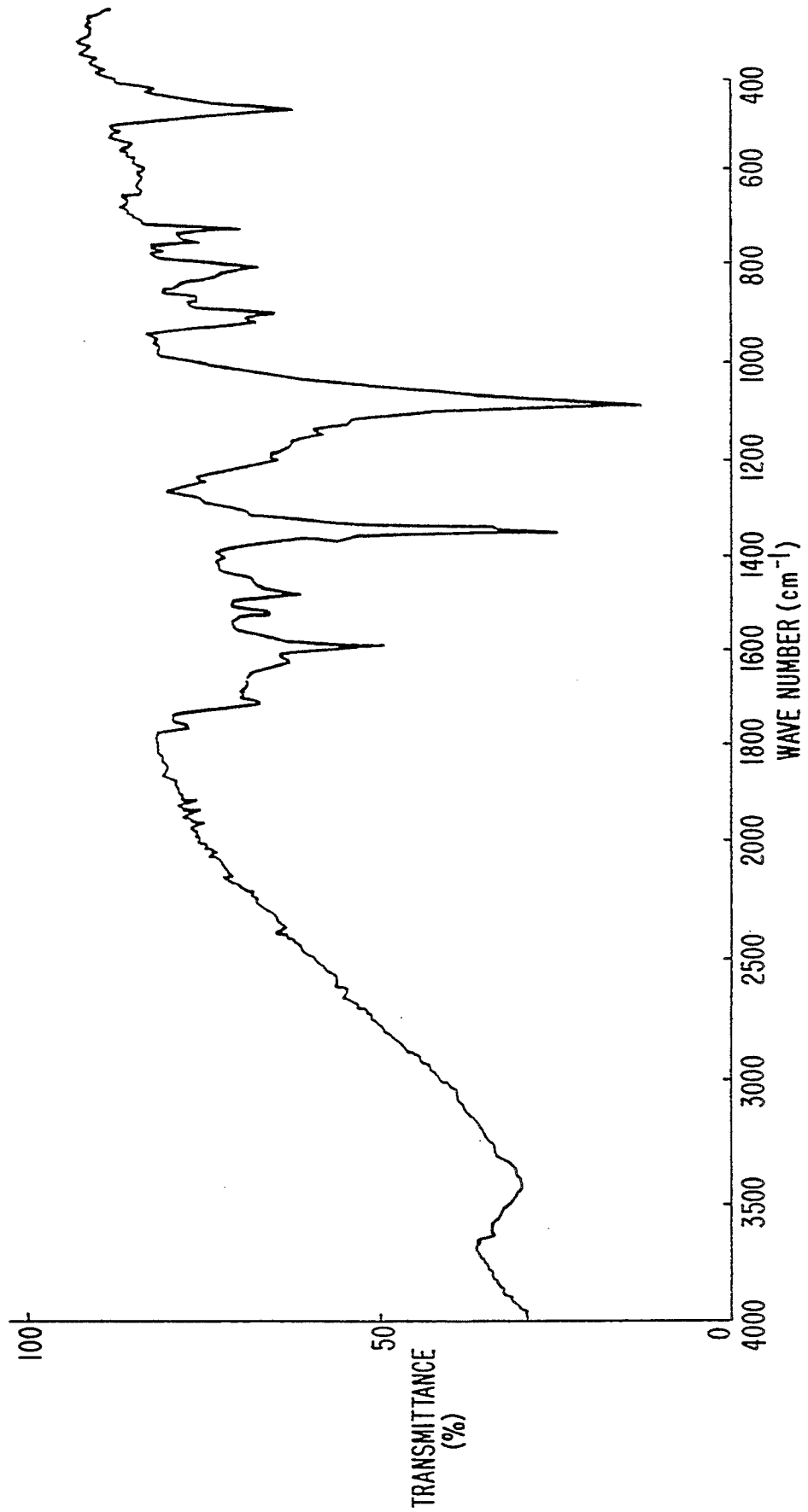
Figure 8:
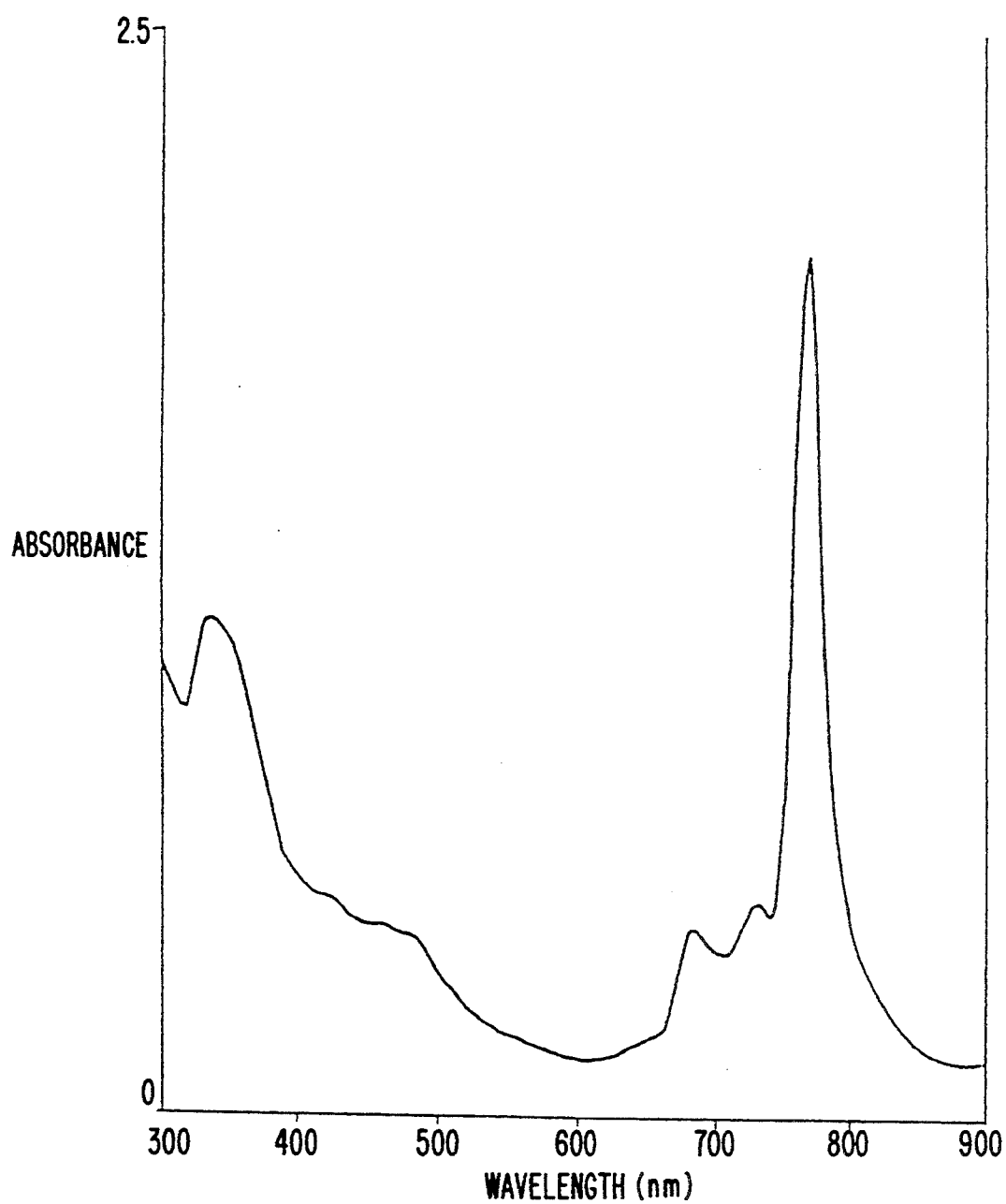

To 250 ml of concentrated sulfuric acid was added 9.7 g (8.6 mmols) of dichlorosilicon-tetrabromonaphthalocyanine, and stirred for about 2 hours. The reaction mixture was poured onto about 800 g of ice and the resulting mixture was allowed to stand overnight. The precipitate formed was filtered, and after sufficient washing with water and then methanol, the precipitate was refluxed in 180 ml of concentrated aqueous ammonia for about 1 hour. After cooling followed by filtration, the residue was sufficiently washed successively with water, methanol and acetone, and dried under reduced pressure to obtain 8.7 g of dihydroxysilicon-tetrabromonaphthalocyanine as a dark-green solid. This dihydroxysilicon-tetrabromonaphthalocyanine was used in the subsequent reaction without further purification. IR spectrum of dihydroxysilicon-tetrabromonaphthalocyanine is shown in FIG. 7. Its electronic spectrum is shown in FIG. 8.

Synthetic Example 6

[Synthesis of bis(tri-n-propylsiloxy)silicon-tetrabromonaphthalocyanine]

Under nitrogen, 8 ml (33.6 mmols) of anhydrous tri-n-butylamine was added to a suspension of 2.82 g (2.6 mmols) of dihydroxysilicon-tetrabromonaphthalocyanine in 280 ml of anhydrous $\beta$-picoline, followed by adding thereto 7.2 ml (32.8 mmols) of tri-n-propylchlorosilane, and the resulting mixture was refluxed for about 2 hours. After cooling, the mixture was poured into 600 ml of ethanol/water (1/1) and sufficiently stirred, and the resulting mixture was allowed to stand overnight. The precipitate formed was filtered and then washed with water. With hot chloroform, only a soluble material in the precipitate was extracted. The chloroform solution thus obtained was dried over anhydrous sodium sulfate, followed by purification with a silica gel column chromatography. Recrystallization from chloroform gave 0.82 g of dark-green crystals. The dark-green crystals were confirmed to be bis(tri-n-propylsiloxy)silicon-tetrabromonaphthalocyanine from the following analysis results.

(1) Melting point: >300° C.

(2) Elementary analysis values*

|  | C | H | N | Br |
|---|---|---|---|---|
| Calculated (%) | 56.50 | 4.45 | 7.99 | 22.78 |
| Found (%) | 56.28 | 4.39 | 8.04 | 22.45 |

Figure 9:
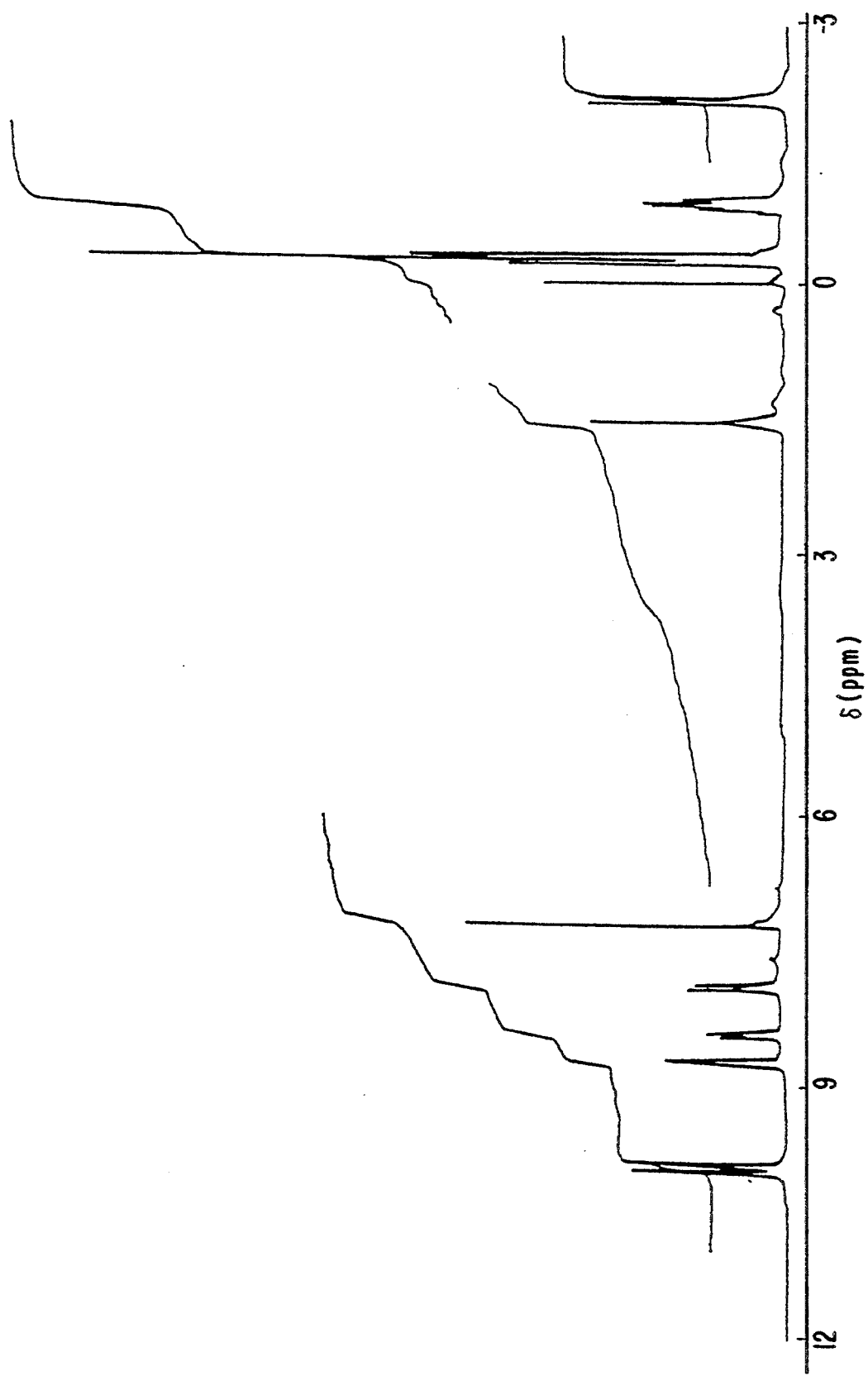

(3) NMR spectrum values (the NMR spectrum is shown in FIG. 9): CDCl$_3$ $\delta$ values 10.08 (4H, br-s) 10.01 (4H, br-s) 8.82 (4H, br-s) 8.54 (4H, dd, J=8.85, 3.05 Hz) 8.00 (4H, d, J=8.85 Hz) −0.29 (18H, t, J=7.17 Hz) −0.90 (12H, sextet-like m) −2.08 (12H, t-like m)

Figure 10:
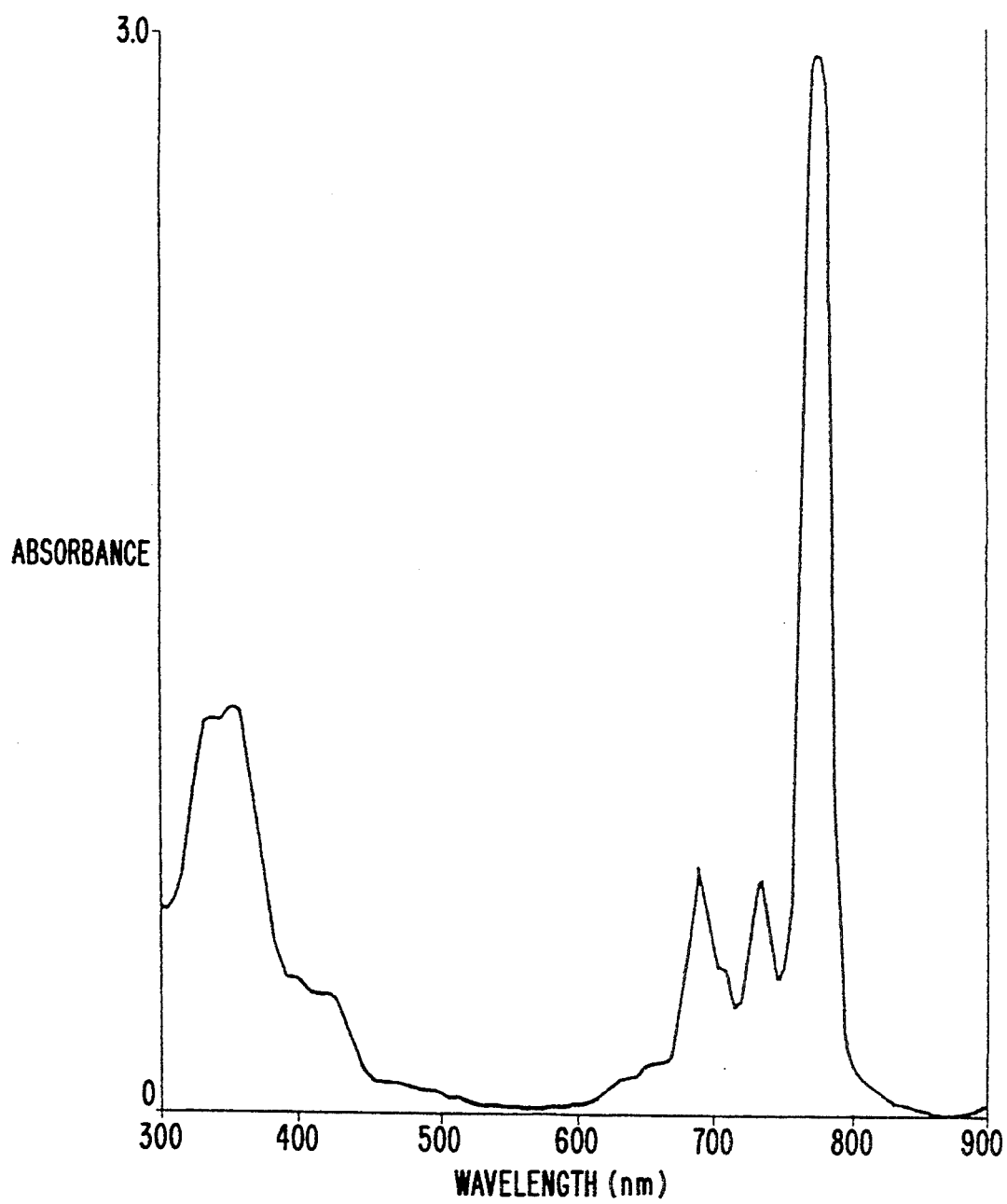
FIGS. 10, 13, 16, 18, 24, 27, 36, 38, 41 and 42 show electronic spectra ($CHCl_3$ solution) of compounds of this invention.

(4) Electronic spectrum (CHCl$_3$ solution) is shown in FIG. 10.

Figure 11:
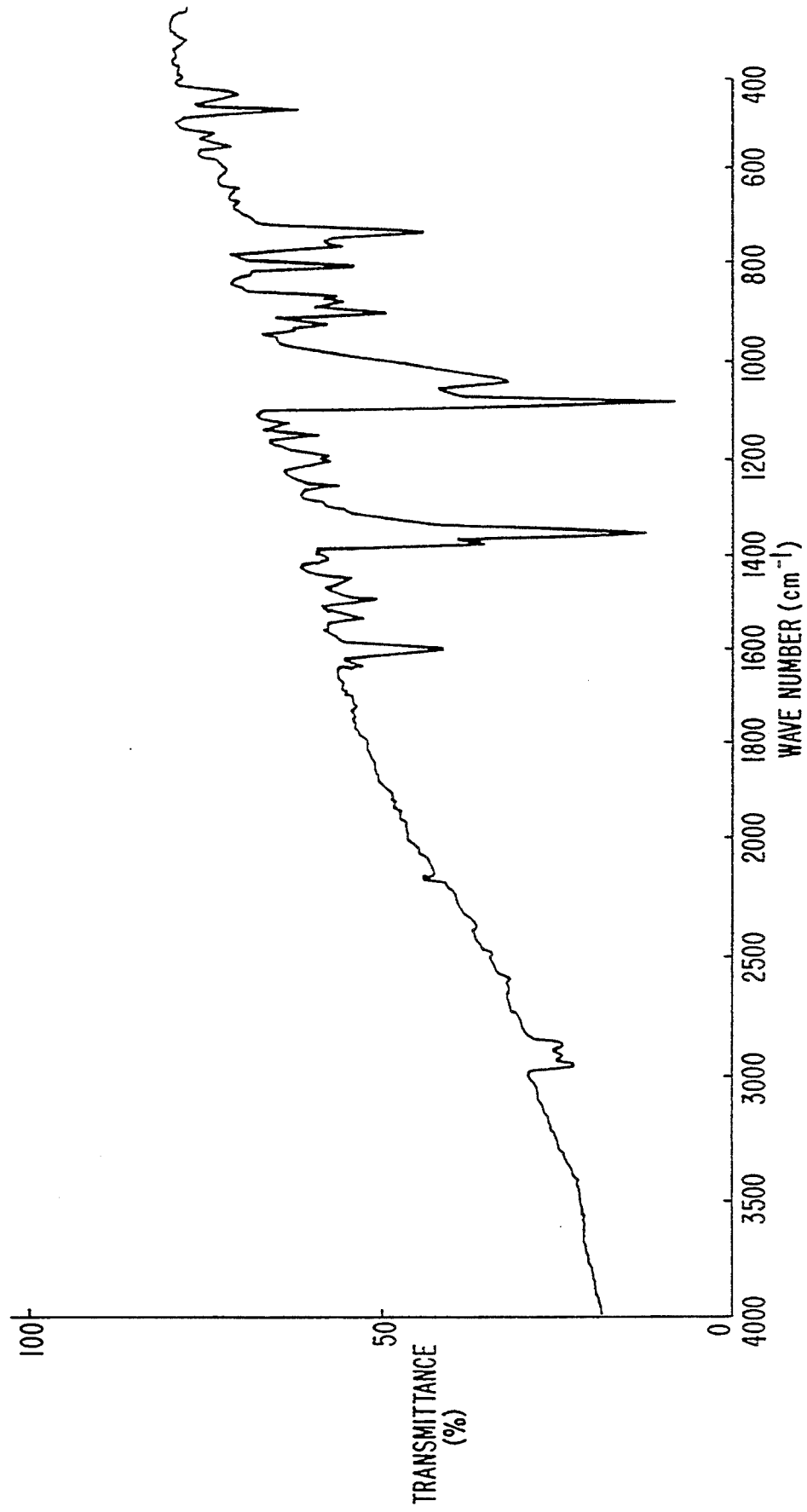

(5) IR spectrum (KBr) is shown in FIG. 11.

Synthetic Example 7

[Synthesis of bis(tri-n-butylsiloxy)silicon-tetrabromonaphthalocyanine]

To a suspension of 2.82 g (2.6 mmols) of dihydroxysilicon-tetrabromonaphthalocyanine in 280 ml of anhydrous $\beta$-picoline were added 8 ml (33.6 mmols) of anhydrous tri-n-butylamine and then 8.8 ml (32.8 mmols) of tri-n-butylchlorosilane, and the resulting mixture was refluxed for about 2 hours. After cooling, the reaction mixture was treated in the same manner as in Synthetic Example 6, and recrystallization from chloroform gave 0.75 g of dark-green crystals. The dark-green crystals were confirmed to be bis(tri-n-butylsiloxy)silicon-tetrabromonaphthalocyanine from the following analysis results:

(1) melting point: >300° C.

(2) Elementary analysis values:

|  | C | H | N | Br |
|---|---|---|---|---|
| Calculated (%) | 58.14 | 5.02 | 7.53 | 21.49 |
| Found (%) | 58.36 | 5.11 | 7.51 | 21.03 |

Figure 12:
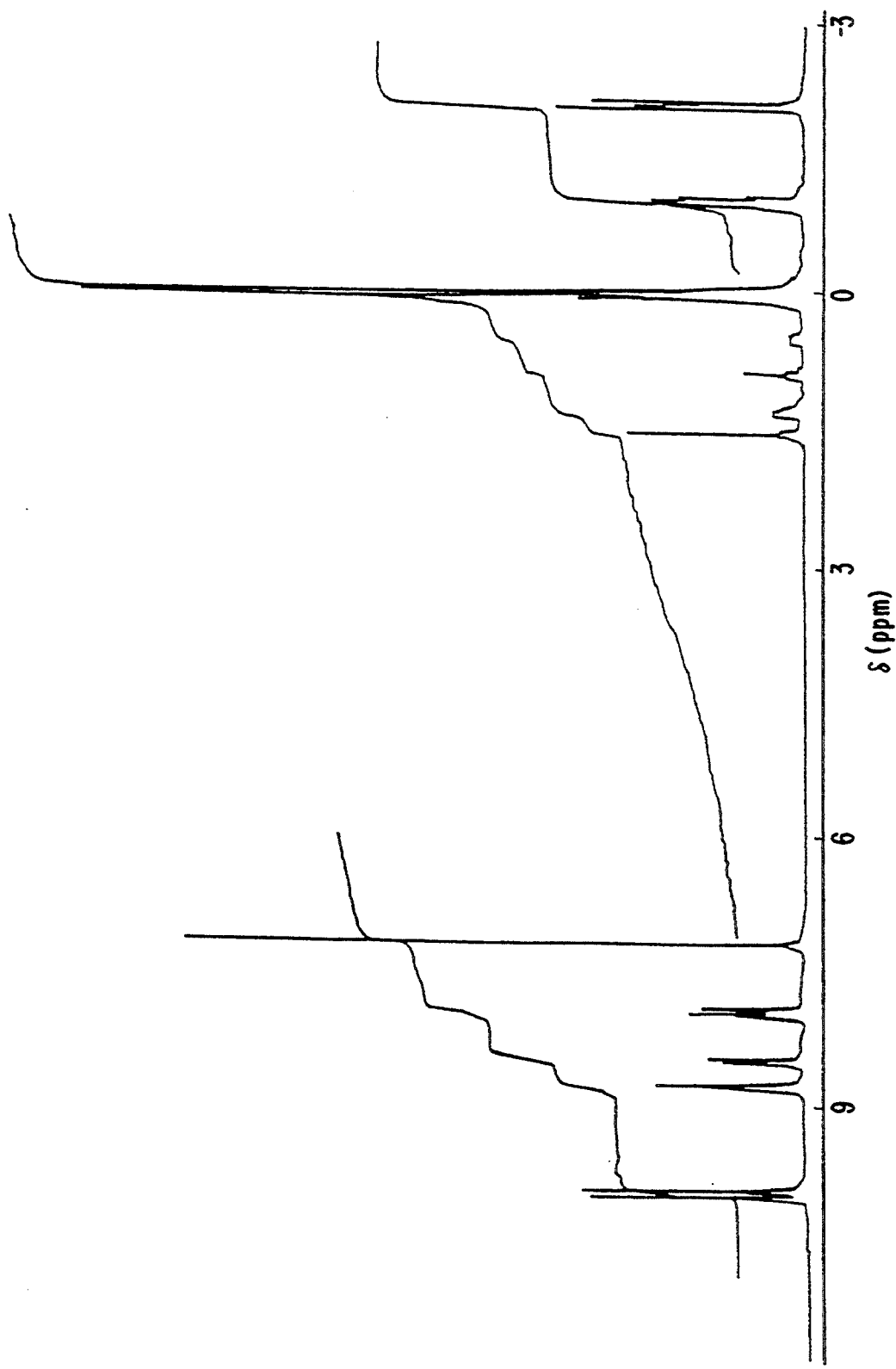

(3) NMR spectrum values (the NMR spectrum is shown in FIG. 12): CDCl$_3$ $\delta$ values 10.09 (4H, br-s) 10.02 )4H, br-s) 8.85 (4H, br-s) 8.55 (4H, J=8.85, 3.05 Hz) 8.01 (4H, d, J=8.85 Hz) 0.02 (30H, m) −0.99 (12H, sextet-like m) −2.07 (12H, t-like m)

Figure 13:
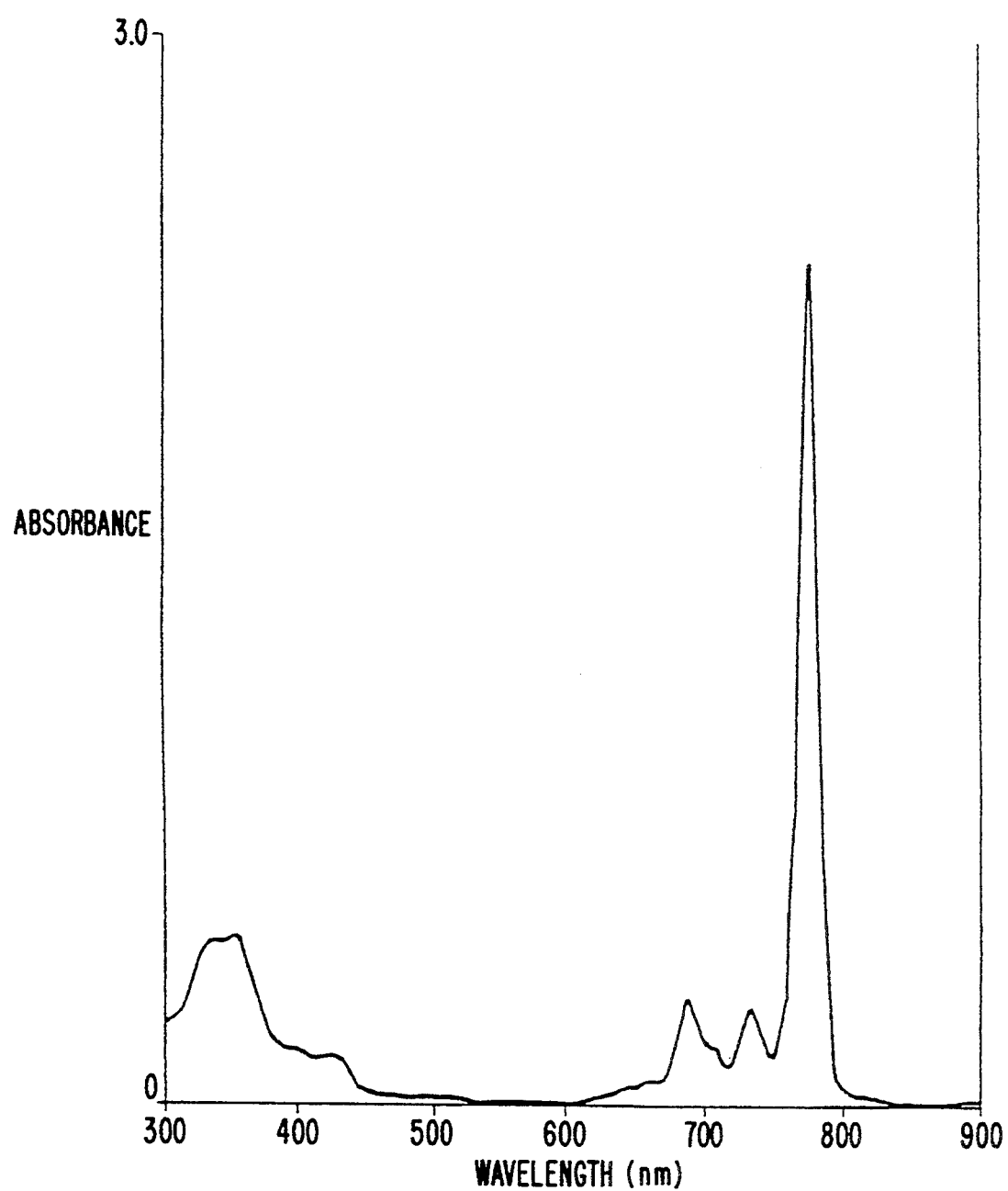

(4) Electronic spectrum (CHCl$_3$ solution) is shown in FIG. 13.

Figure 14:
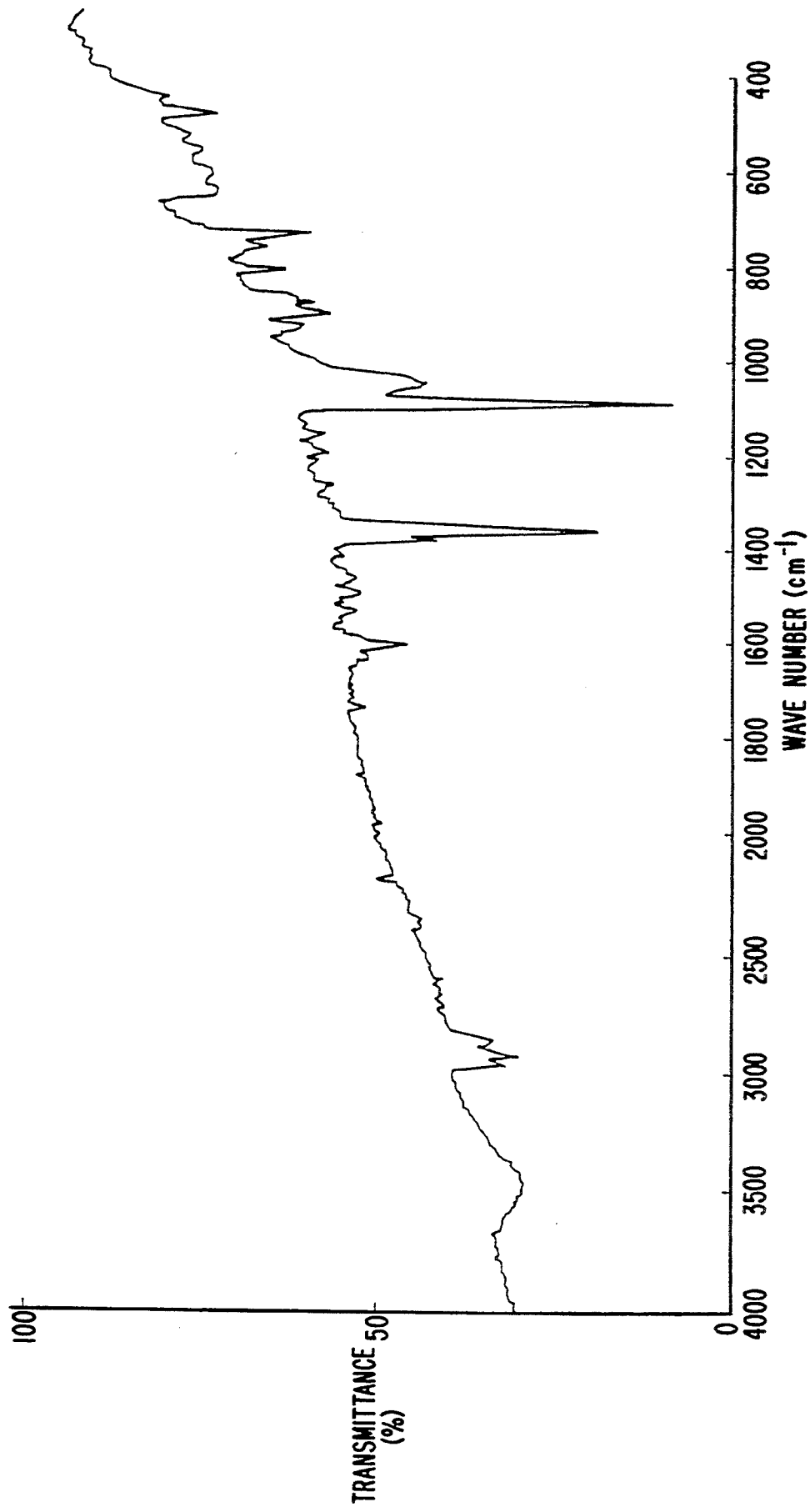

(5) IR spectrum (KBr) is shown in FIG. 14.

Synthetic Example 8

[Synthesis of bis(tri-n-hexylsiloxy)silicon-tetrabromonaphthalocyanine]

To a suspension of 2.82 g (2.6 mmols) of dihydroxysilicon-tetrabromonaphthalocyanine in 280 ml of anhydrous $\beta$-picoline were added 8 ml (33.6 mmols) of anhydrous tri-n-butylamine and then 12 ml (32.8 mmols) of tri-n-hexylchlorosilane, and the resulting mixture was refluxed for about 2 hours. After cooling, the reaction mixture was treated in the same manner as in Synthetic Example 6, and recrystallization from hexane/chloroform gave 0.78 g of dark-green crystals. The dark-green crystals were confirmed to be bis(tri-n-hexylsiloxy)silicon-tetrabromonaphthalocyanine from the following analysis results:

(1) melting point: 298°-300° C.

(2) Elementary analysis values:

|  | C | H | N | Br |
|---|---|---|---|---|
| Calculated (%): | 60.94 | 5.97 | 6.77 | 19.30 |
| Found (%): | 60.77 | 5.71 | 6.65 | 19.02 |

Figure 15:
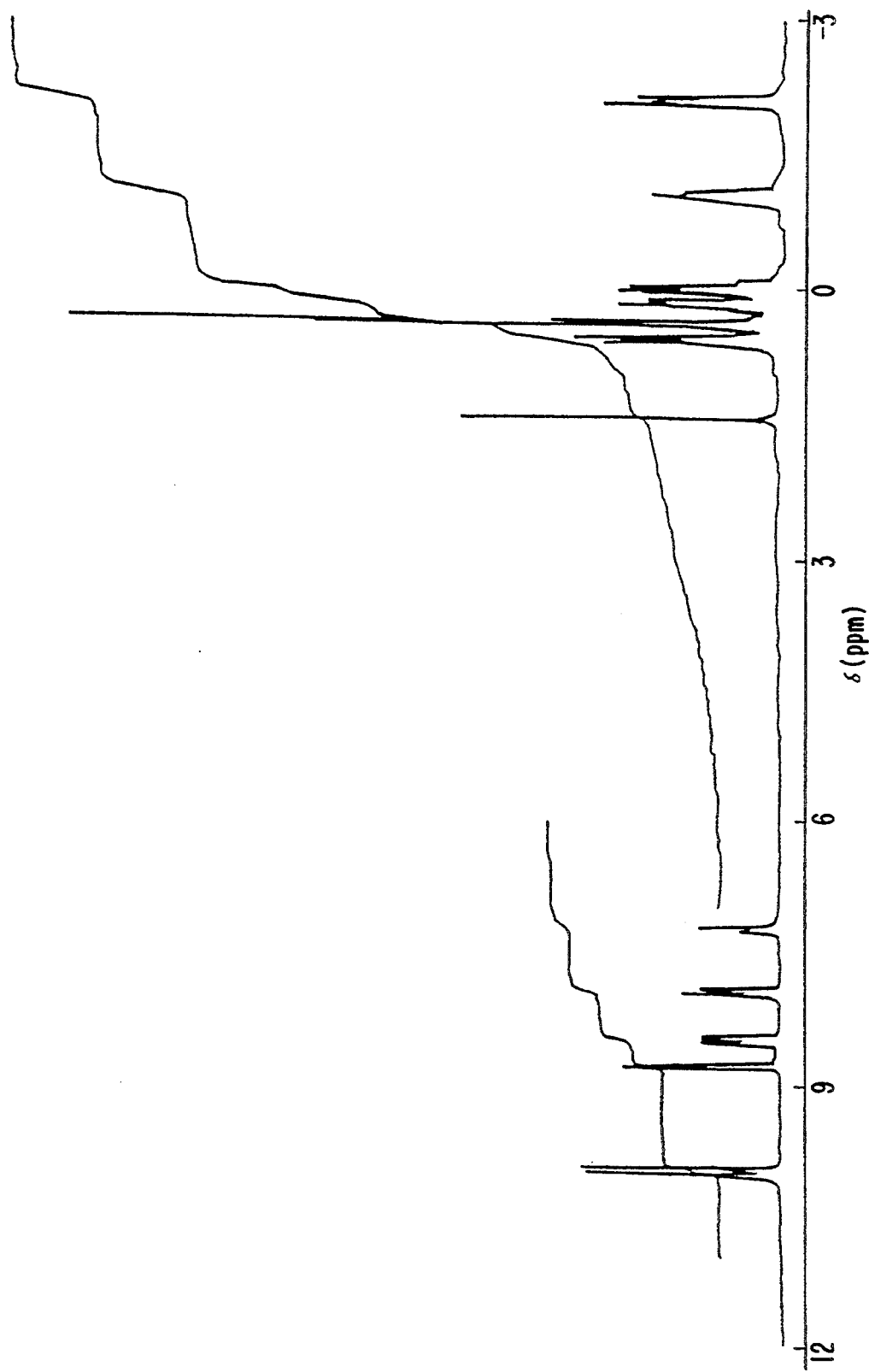

(3) NMR spectrum values (the NMR spectrum is shown in FIG. 15): CDCl$_3$ $\delta$ values 10.06 (4H, br-s) 10.00 (4H, br-s) 8.83 (4H, br-s) 8.53 (4H, dd, J=8.85, 2.44 Hz) 7.99 (4H, dd, J=8.85, 2.44 Hz) 0.63 (12H, sextet, J=7.32 Hz) 0.45 (18H, t, J=7.32 Hz) 0.22 (18H, quintet, J=7.32 Hz) 0.05 (12H, quintet, J=7.32 Hz) −1.02 (12H, quintet-like m) −2.10 (12H, t-like m)

Figure 16:
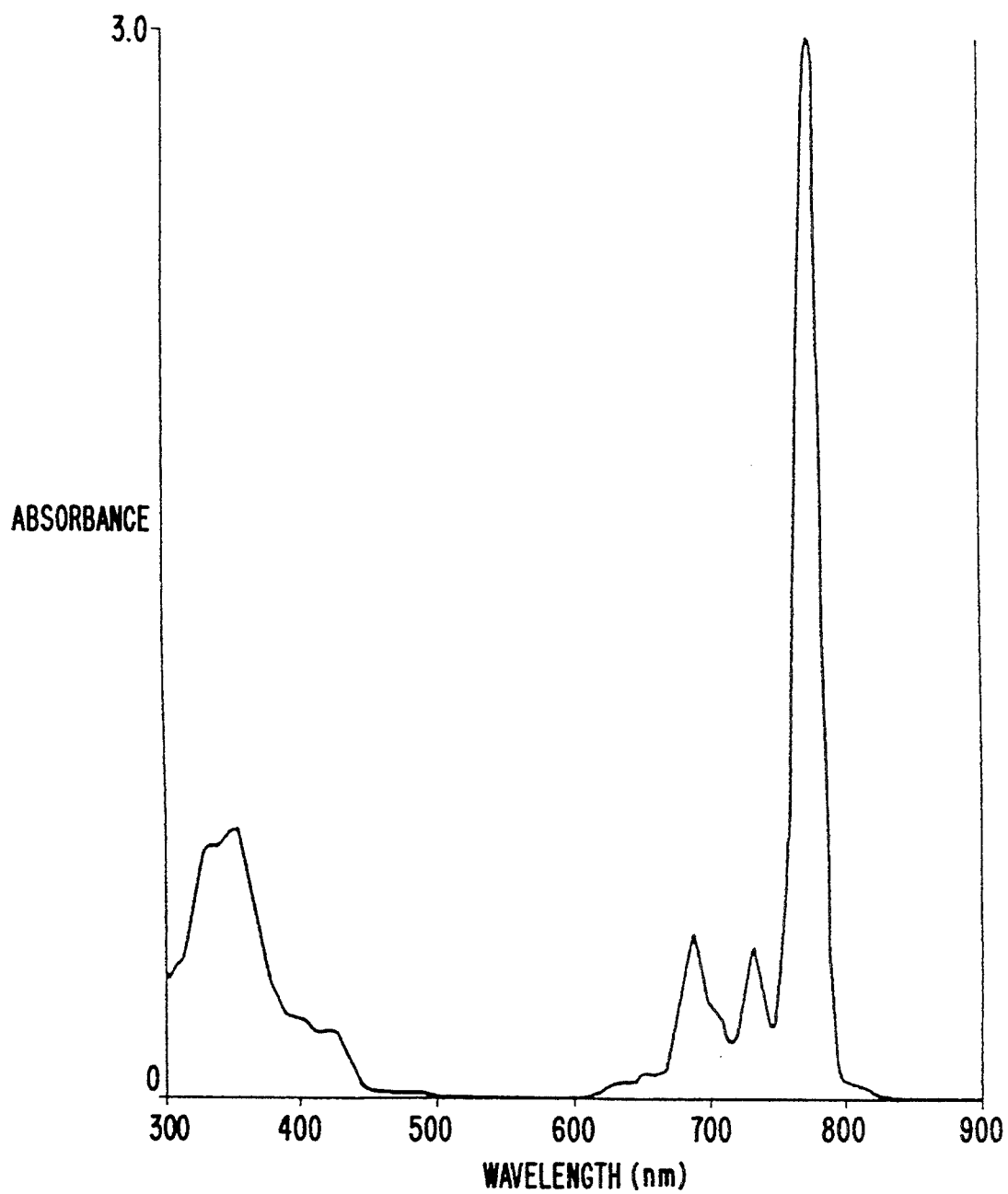
Figure 17:
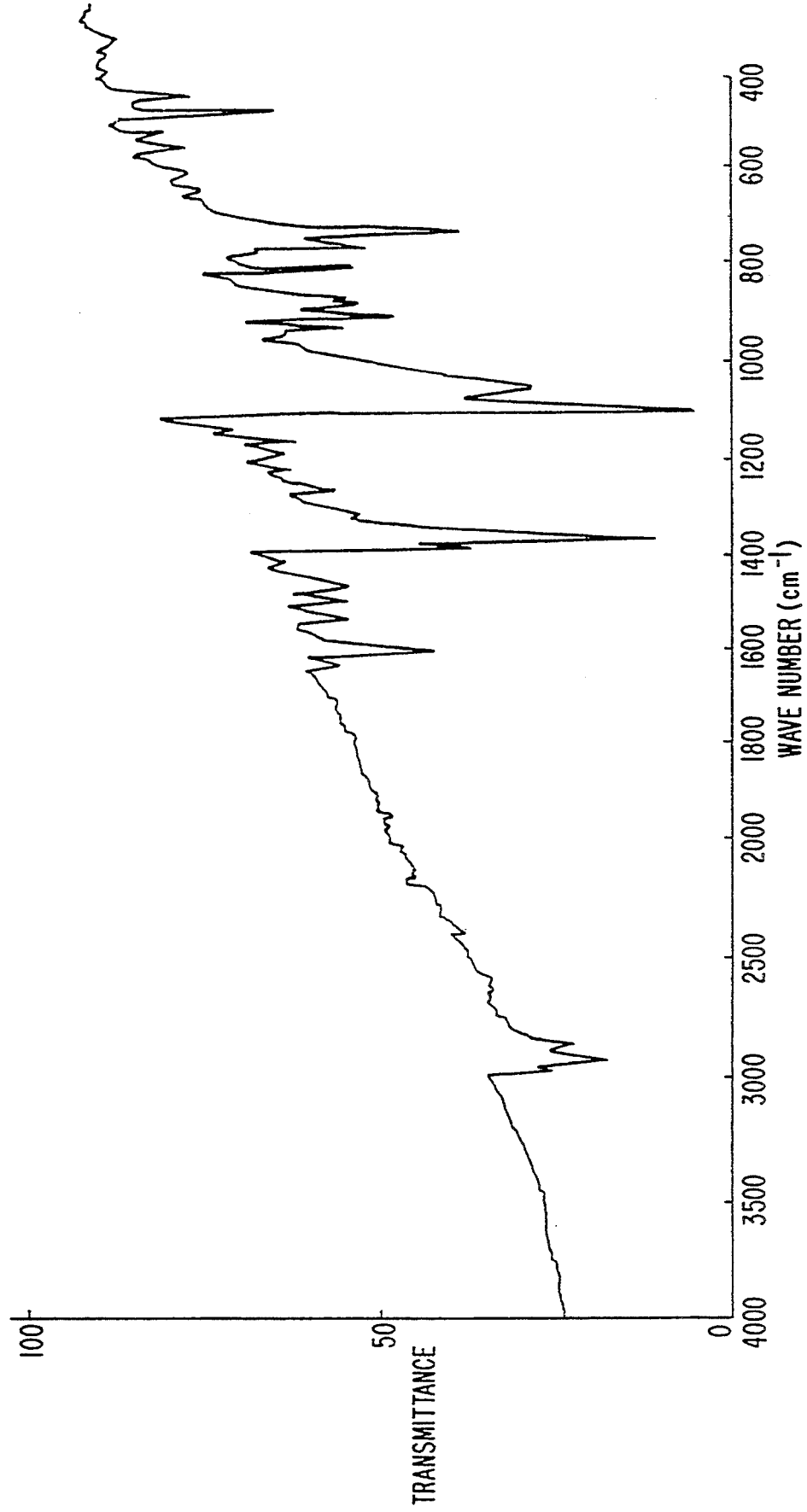

(4) Electronic spectrum (CHCl$_3$ solution) is shown in FIG. 16. (5) IR spectrum (KBr) is shown in FIG. 17.

Synthetic Example 9

[Synthesis of bis(triethylsiloxy)silicon-tetrabromonaphthalocyanine]

To a suspension of 2.82 g (2.6 mmols) of dihydroxysilicon-tetrabromonaphthalocyanine in 100 ml of quinoline was added 10 ml (65 mmols) of triethylsilanol, and the resulting mixture was refluxed for about 3 hours. After cooling, the reaction mixture was poured into 500 ml of ethanol/water (1/1) and sufficiently stirred, and the resulting mixture was allowed to stand overnight. The precipitate formed was filtered and sufficiently washed with methanol and then chloroform. The crystals thus obtained were washed with chloroform by the Soxhlet extraction method to obtain 2.1 g of dark-green crystals. The dark-green crystals were confirmed to be bis(triethylsiloxy)silicon-tetrabromonaphthalocyanine from the following analysis results:

(1) Melting point: >300° C.

(2) Elementary analysis values:

|  | C | H | N | Br |
|---|---|---|---|---|
| Calculated (%) | 54.64 | 3.82 | 8.50 | 24.23 |
| Found (%) | 54.18 | 3.62 | 8.81 | 23.94 |

(3) NMR spectrum values: CDCl$_3$ δ values 10.07 (4H, br-s) 10.00 (4H, br-s) 8.83 (4H, br-s) 8.54 (4H, dd, J=8.85, 3.05 Hz) 8.01 (4H, d, J=8.85 Hz) −1.04 (18H, t, J=7.32 Hz) −2.05 (12H, q, J=7.32 Hz)

Figure 18:
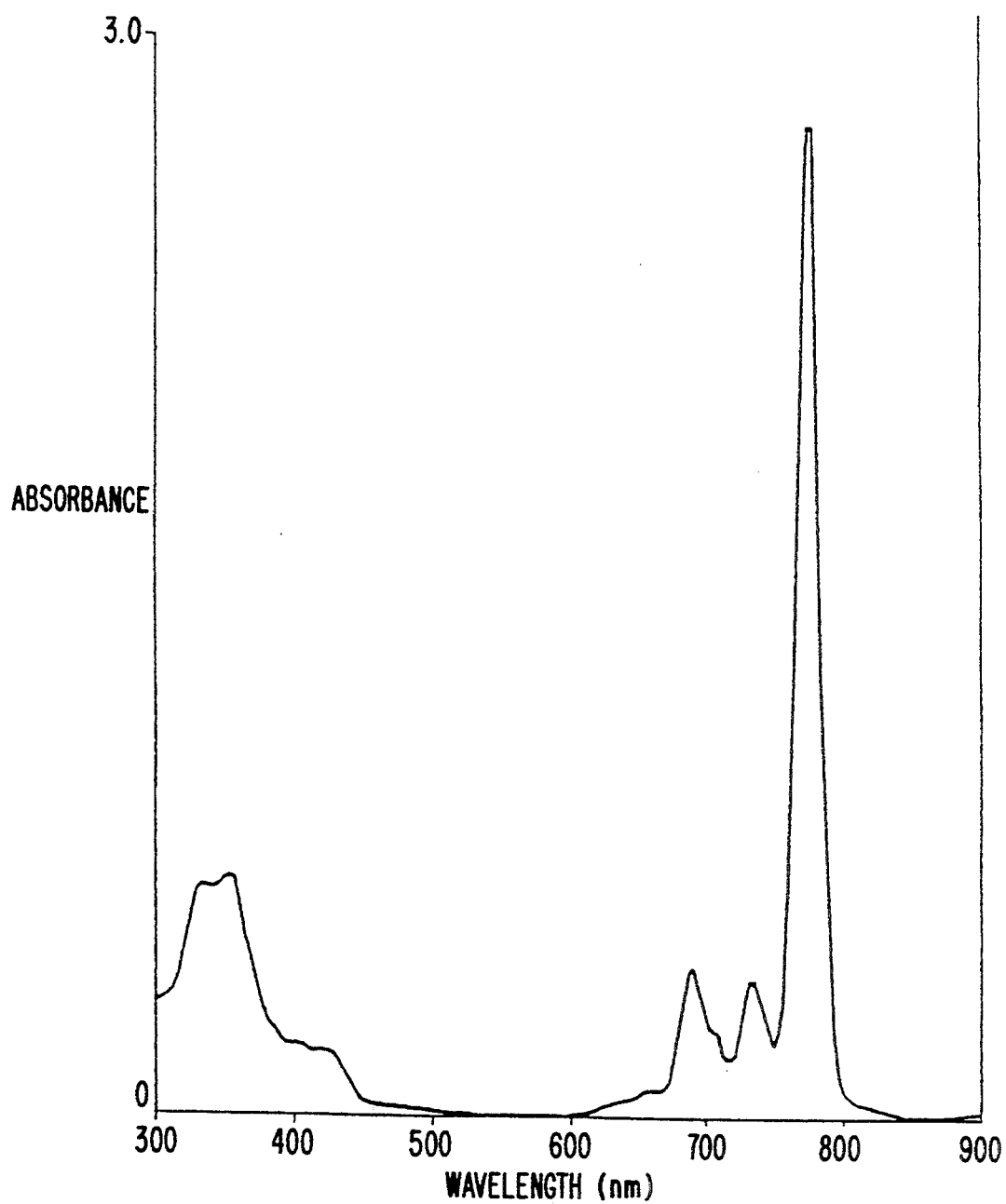

(4) Electronic spectrum (CHCl$_3$ solution) is shown in FIG. 18.

Figure 19:
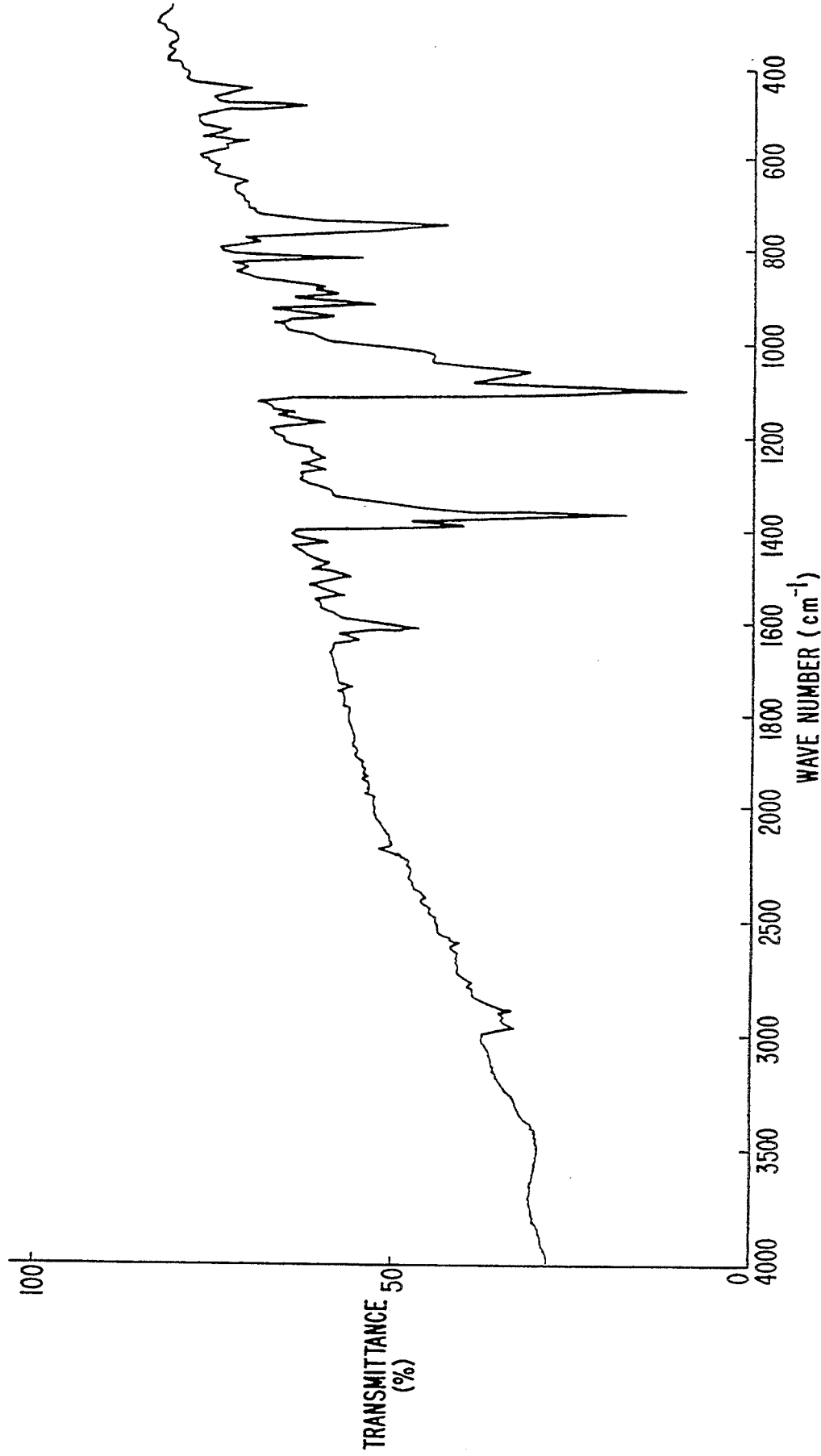

(5) IR spectrum (KBr) is shown in FIG. 19.

Synthetic Example 10

[Synthesis of bis(tributylsiloxy)silicon-tetraphenylthionaphthalocyanine]

A suspension of 5 g (3.36 mmols) of bis(tributylsiloxy)silicon-tetrabromonaphthalocyanine and 2.5 g (14.47 mmols) of copper phenylthiolate in 50 ml of quinoline was stirred at 160° C. for 1 hour and then at 180° C. for 5 hours. After cooling, the reaction mixture was poured into 400 ml of methanol/water (1/1). After stirring for a while, the resulting mixture was allowed to stand overnight at room temperature. The solid precipitated was filtered and then washed with methanol. Only a material soluble in toluene was extracted from the thus obtained solid with hot toluene, separated and purified with a silica gel column chromatography (eluent: hexane/toluene (1/1)), and then recrystallized from methylene chloride/ethanol to obtain bis(tributylsiloxy)silicon-tetraphenylthionaphthalocyanine as green crystals (3.03 g, 56%). The crystals were confirmed to be bis(tributylsiloxy)silicon-tetraphenylthionaphthalocyanine from the following analysis results:

(1) Elementary analysis values:

|  | C | H | N | S |
|---|---|---|---|---|
| Calculated (%) | 71.87 | 59.91 | 6.98 | 7.99 |
| Found (%) | 71.92 | 6.02 | 7.04 | 7.49 |

Figure 20:
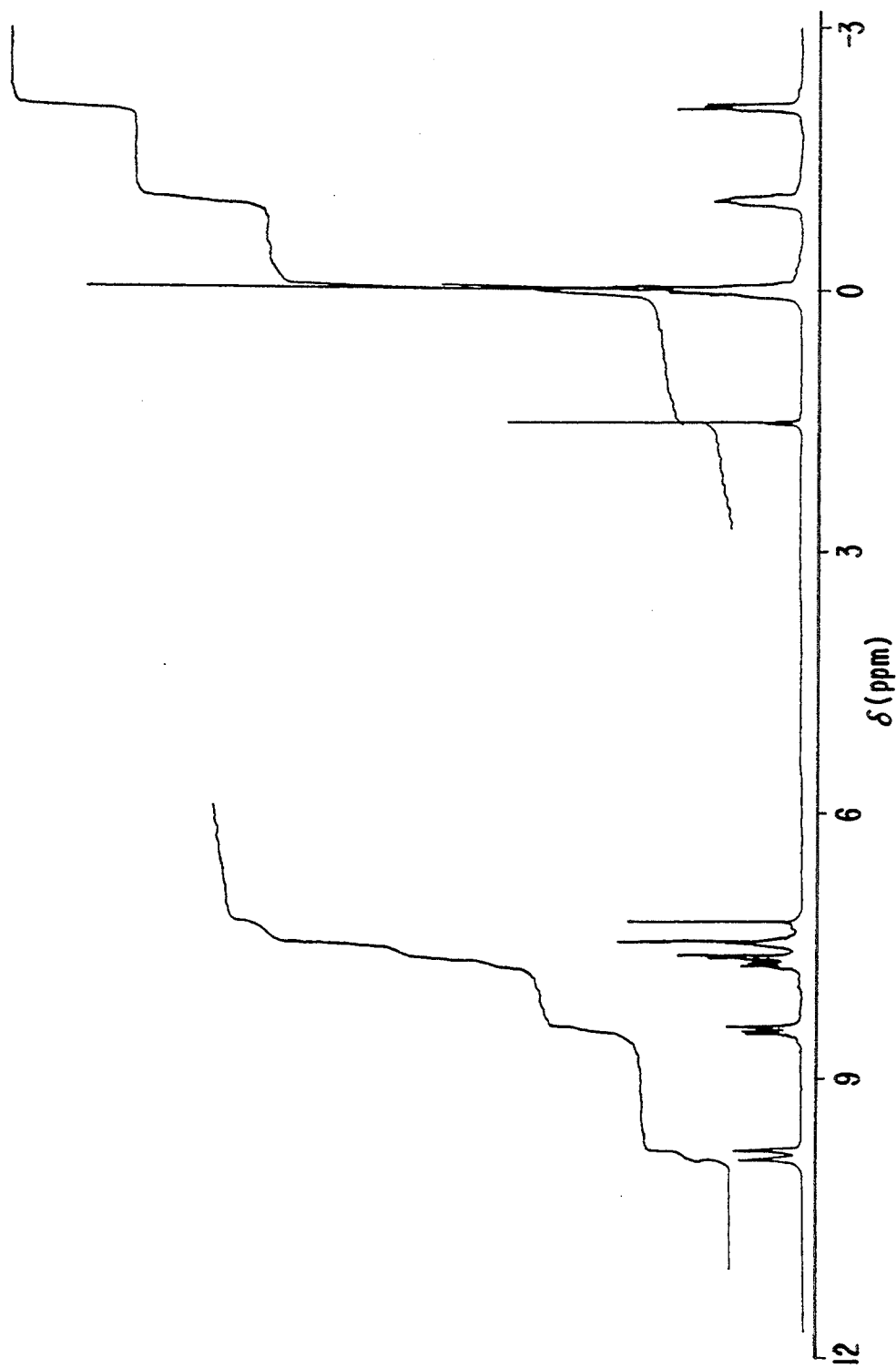

(2) NMR spectrum values (the NMR spectrum is shown in FIG. 20): CDCl$_3$ δ values 9.99 (4H, d, J=3.66 Hz) 9.89 (4H, br-s) 8.53 (4H, d, J=8.85 Hz) 8.46 (4H, br-s) 7.76 (4H, dd, J=8.85, 1.22 Hz) 7.65 (8H, m) 7.50 (12H, m) −0.02 (30H, m) −0.99 (12H, quintet-like m) −2.09 (12H, t-like m)

(3) Melting point: 293°–295° C.

Figure 21:
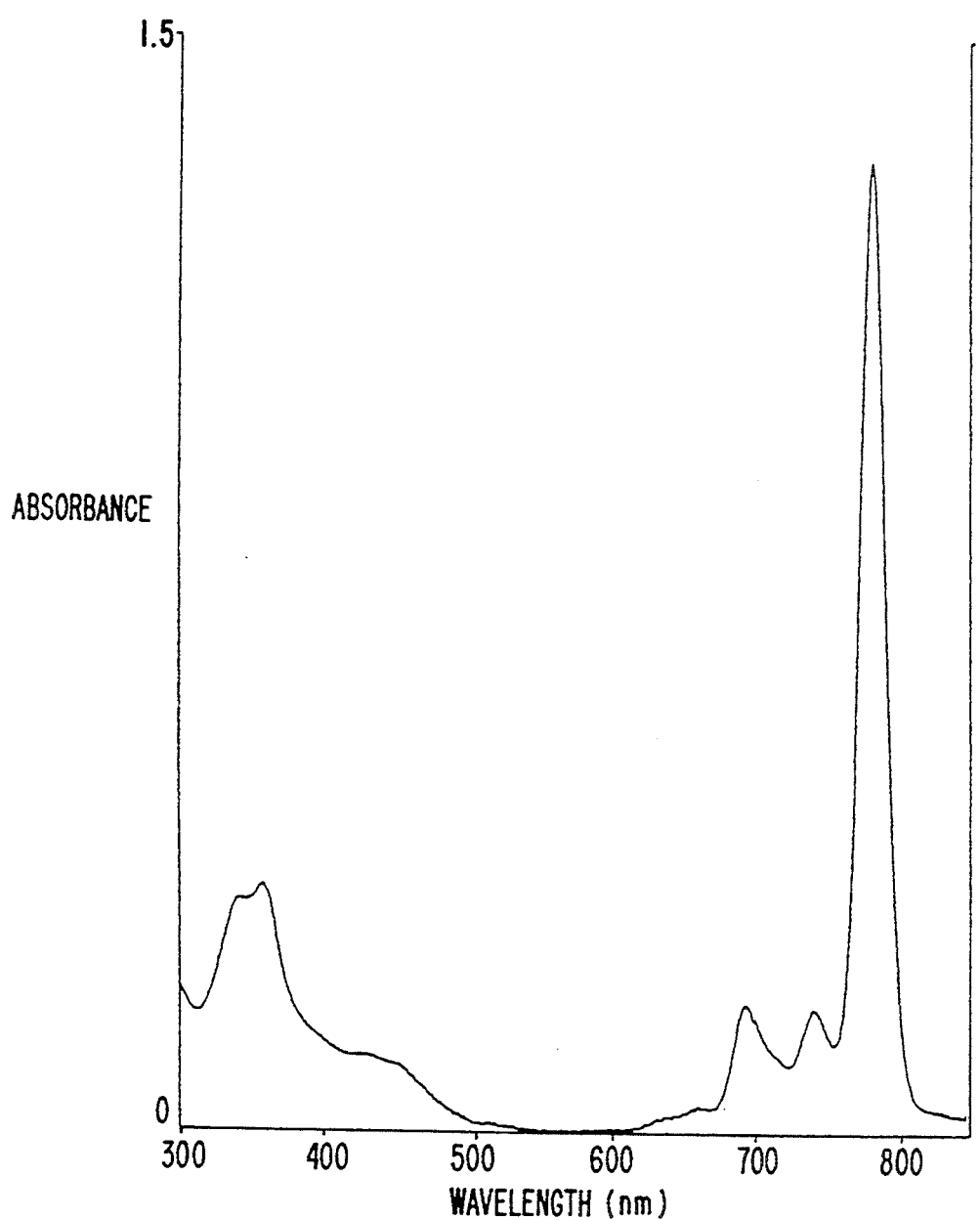
FIG. 21 is an electronic spectrum ($CH_2Cl_2$ solution) of a compound of this invention.

(4) Electronic spectrum (methylene chloride solution) is shown in FIG. 21.

Figure 22:
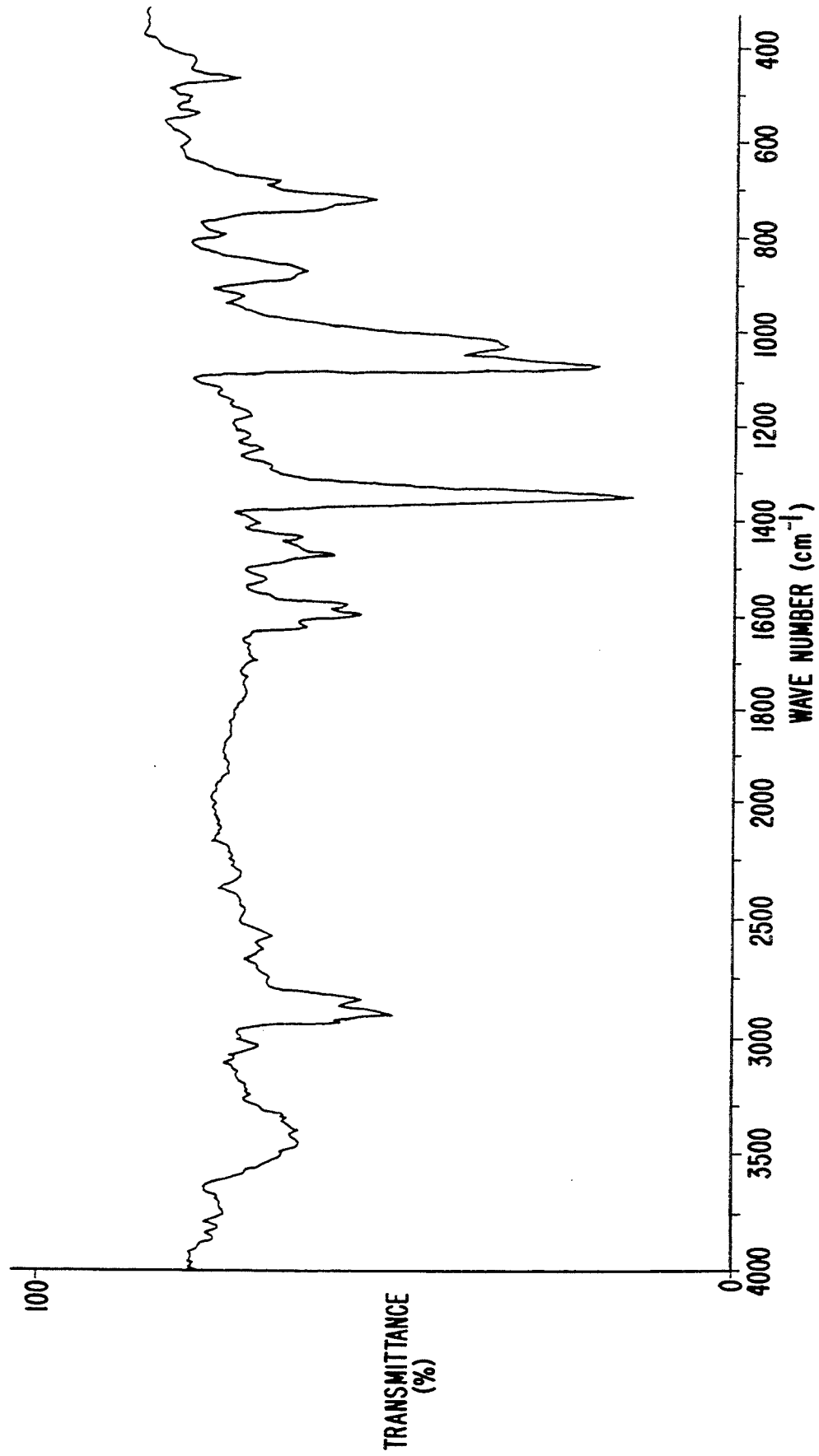

(5) IR spectrum (KBr) is shown in FIG. 22.

Synthetic Examples 11

Synthesis of bis(tri-n-propylsiloxy)silicon-tetrakis[2-(2'-ethylhexyloxycarbonyl)ethylthio]naphthalocyanine]

To a solution of 140 mg (0.1 mmol) of bis(tri-n-propylsiloxy)silicon-tetrabromonaphthalocyanine in a mixture of 10 ml of quinoline and 3.2 ml of pyridine was added 2.47 g (8.8 mmols) of cuprous 2-(2'-ethylhexyloxycarbonyl)ethylthiolate synthesized according to the method described in Organic Syntheses, vol. 44, p. 22, and the resulting mixture was refluxed at 160° to 170° C. for 8 hours. After cooling, the reaction mixture was treated in the same manner as in Synthetic Example 10 to obtain 46 mg (24%) of yellow-green crystals. The yellow-green crystals were confirmed to be bis(tri-n-propylsiloxy)silicon-tetrakis[ 2-(2'-ethylhexyloxycarbonyl)ethylthio]naphthalocyanine from the following analysis results.

(1) Melting point: 125°–127° C.

(2) Elementary analysis values:

|  | C | H | N |
|---|---|---|---|
| Calculated (%) | 67.65 | 7.54 | 5.74 |
| Found (%) | 67.89 | 7.42 | 5.65 |

Figure 23:
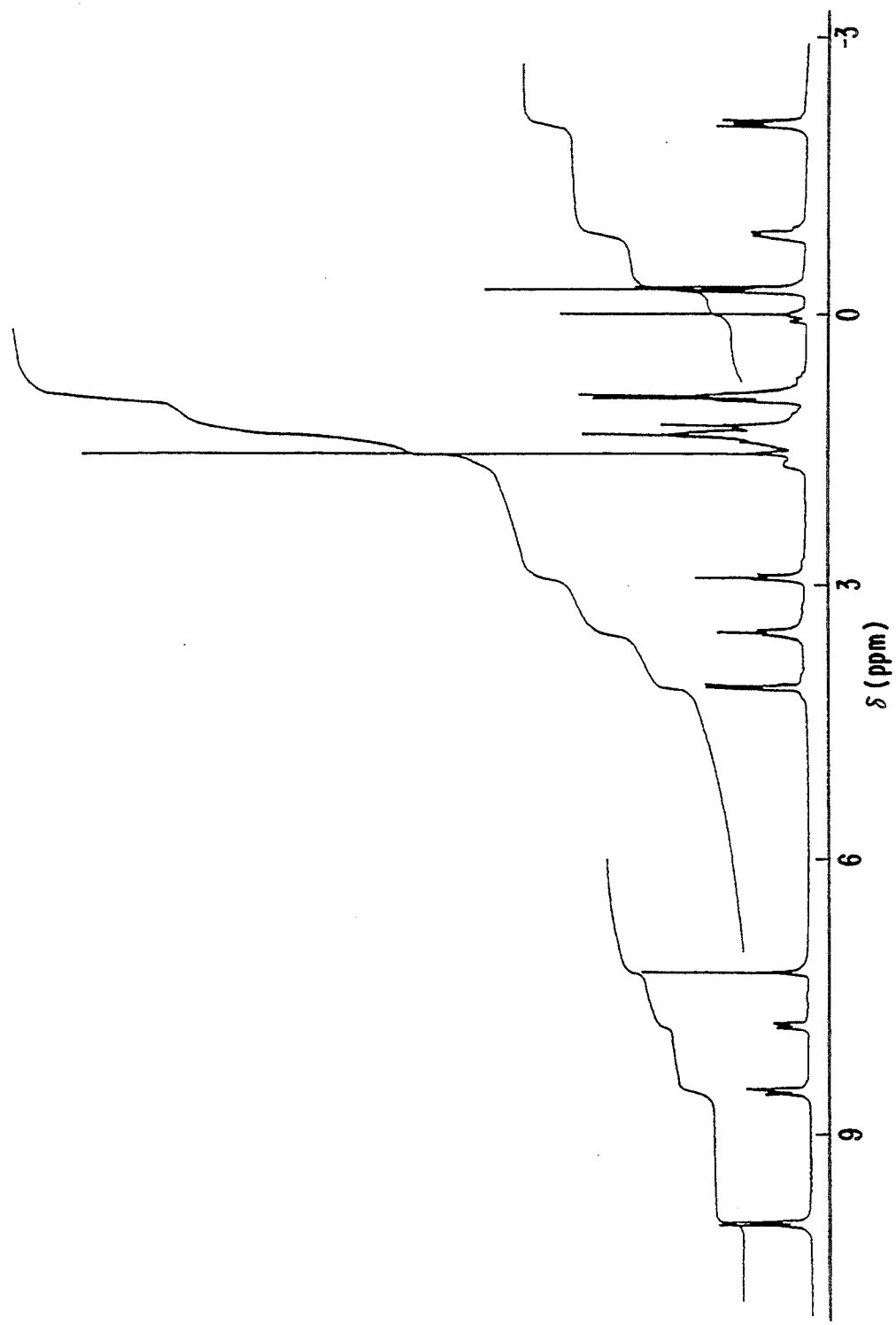

(3) NMR spectrum values (the NMR spectrum is shown in FIG. 23): CDCl$_3$ δ values 10.04 (4H, br-s) 10.00 (4H, br-s) 8.57 (4H, d, J=8.85 Hz) 8.53 84H, br-s) 7.84 (4H, d, J=8.85 Hz) 4.14 (8H, d, J=5.80 Hz) 3.56 (8H, t, J=7.33 Hz) 2.93 (8H, t, J=7.33 Hz) 0.7–1.8 (36H, m) 0.94 (36H, m) −0.27 (18H, t, J=7.33 Hz) −0.87 (12H, sextet-like m) −2.08 (12H, t-like m)

Figure 24:
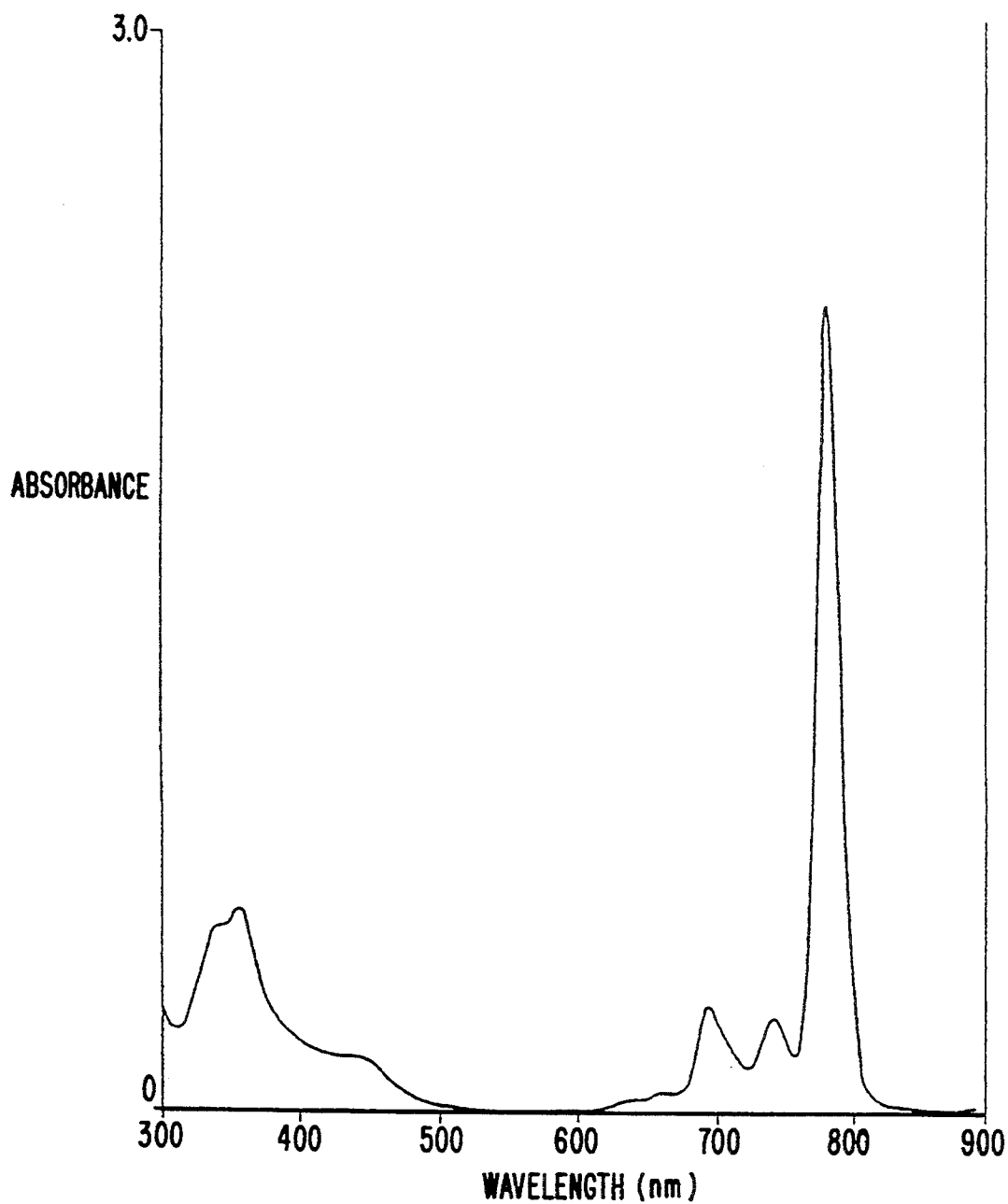

(4) Electronic spectrum (CHCl$_3$ solution) is shown in FIG. 24.

Figure 25:
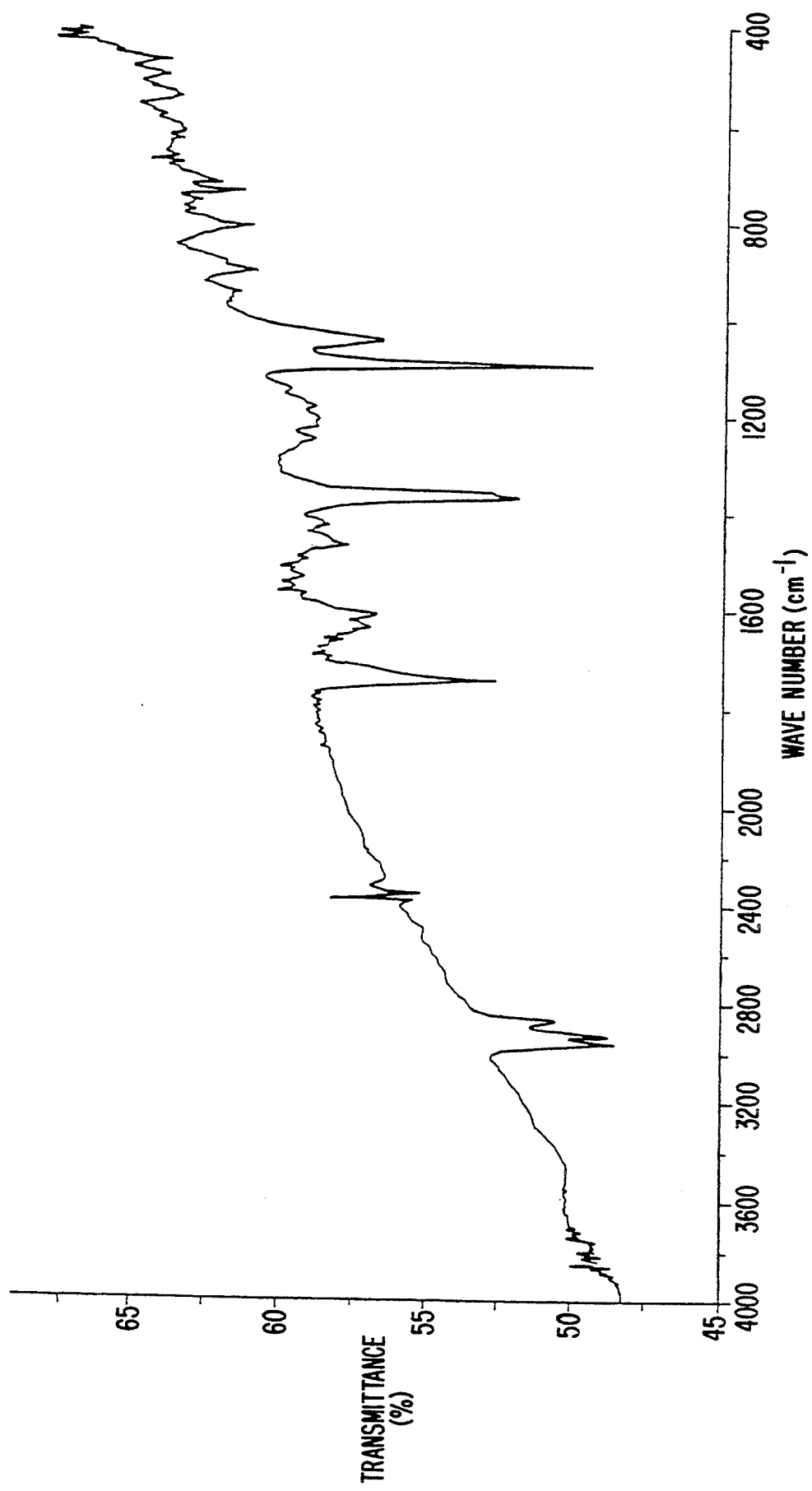

(5) IR spectrum (KBr) is shown in FIG. 25.

Synthetic Example 12

{Synthesis of bis(tri-n-propylsiloxy)silicon-tetrakis[2-(2',2',4',4'-tetramethylpentyloxycarbonyl)ethylthio]-naphthalocyanine}

To a solution of 140 mg (0.1 mmol) of bis(tri-n-Propylsiloxy)silicon-tetrabromonaphthalocyanine in a mixture of 10 ml of quinoline and 3.2 ml of pyridine was added 2.59 g (8.8 mmols) of cuprous 2-(2',2',4',4'-tetramethylpentyloxycarbonyl)ethylthiolate synthesized according to the method described in Organic Syntheses, vol. 42, p. 22, and the resulting mixture was refluxed at 160° to 170° C. for 8 hours. After cooling, the reaction mixture was treated in the same manner as in Synthetic Example 10 to obtain 52 mg (26%) of yellow-green crystals. The yellow-green crystals were confirmed to be bis(tri-n-propylsiloxy)silicon-tetrakis[2-(2',2',4',4'-tetramethylpentyloxycarbonyl)ethylthio]-naphthalocyanine from the following analysis results:

(1) Melting point: 131° to 133° C.

(2) Elementary analysis values:

|  | C | H | N |
|---|---|---|---|
| Calculated (%) | 68.15 | 7.73 | 5.58 |
| Found (%) | 68.13 | 7.65 | 5.37 |

Figure 26:
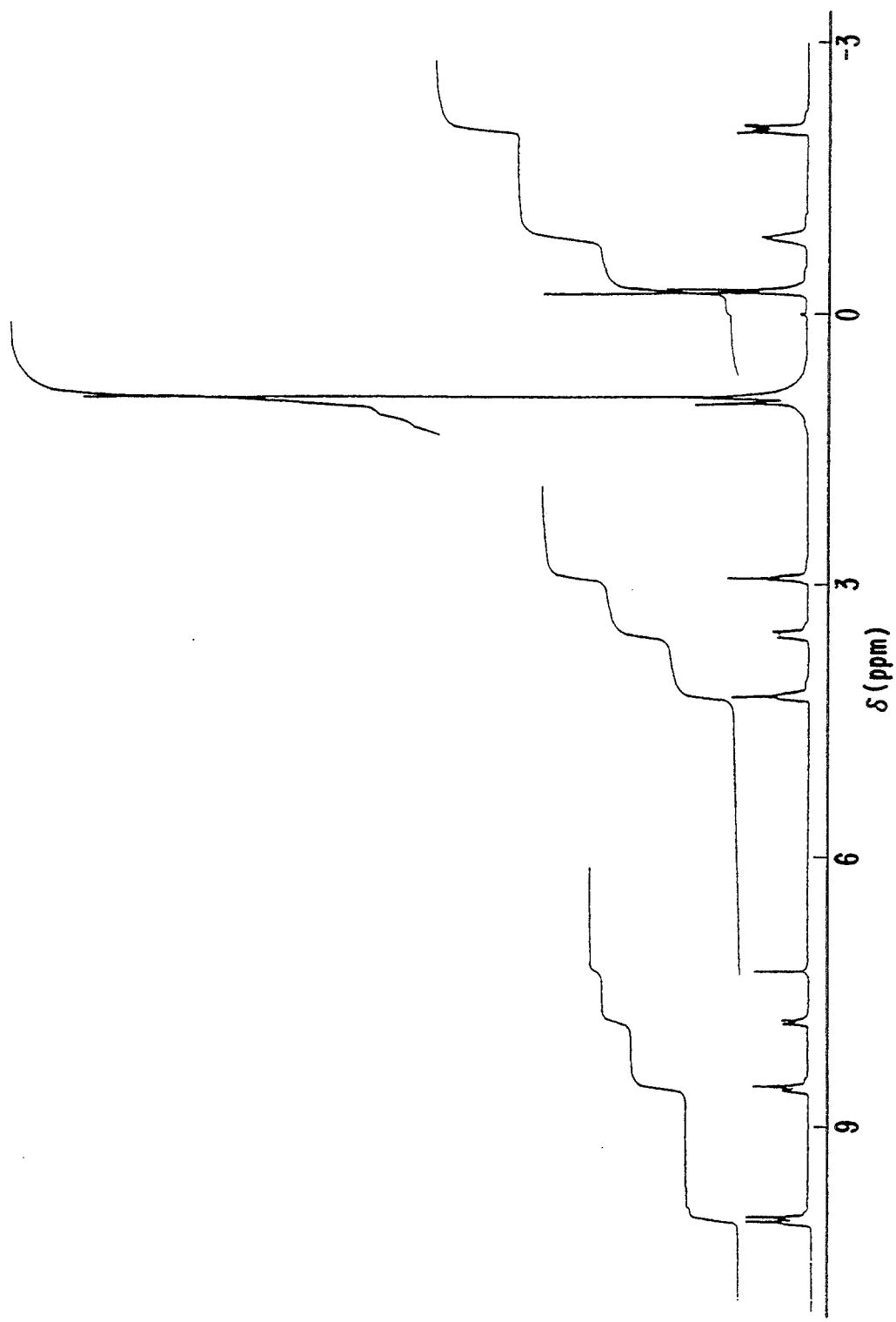

(3) NMR spectrum values (the NMR spectrum is shown in FIG. 26): CDCl$_3$ δ values 10.05 (4H, br-s) 10.01 (4H, br-s) 8.57 (4H, d, J=8.55 Hz) 8.54 (4H, br-s) 7.84 (4H, d, J=8.55 Hz) 4.24 (8H, t, J=6.56 Hz) 3.57 (8H, t, J=7.33 Hz) 2.93 (8H, t, J=7.33 Hz) 1.01 (8H, d, J=5.5 Hz) 0.94 (60H, br-s) −0.26 (18H, t, J=7.33 Hz) −0.85 (12H, sextet-like m) −2.06 (12H, t-like m)

Figure 27:
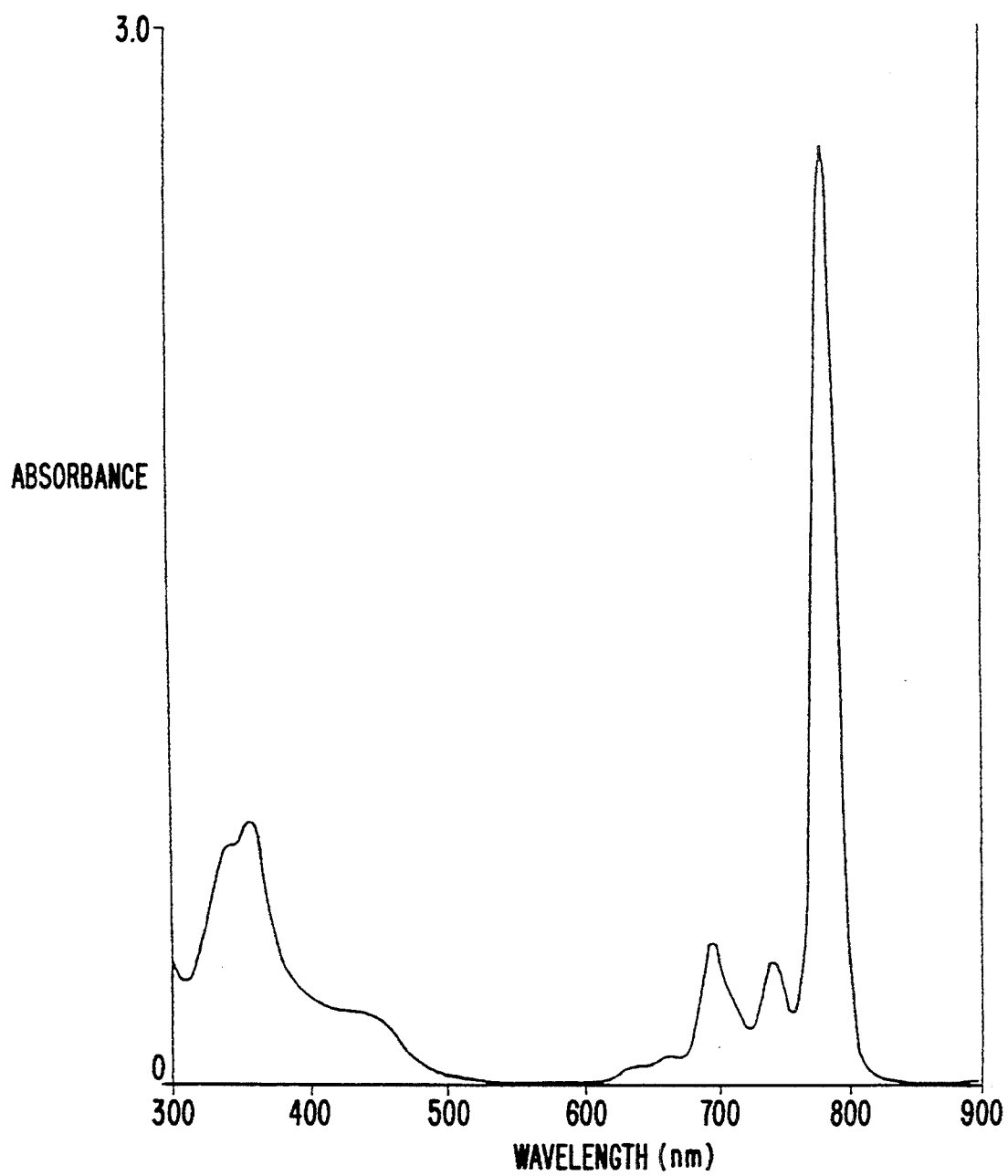

(4) Electronic spectrum (CHCl$_3$ solution) is shown in FIG. 27.

Figure 28:
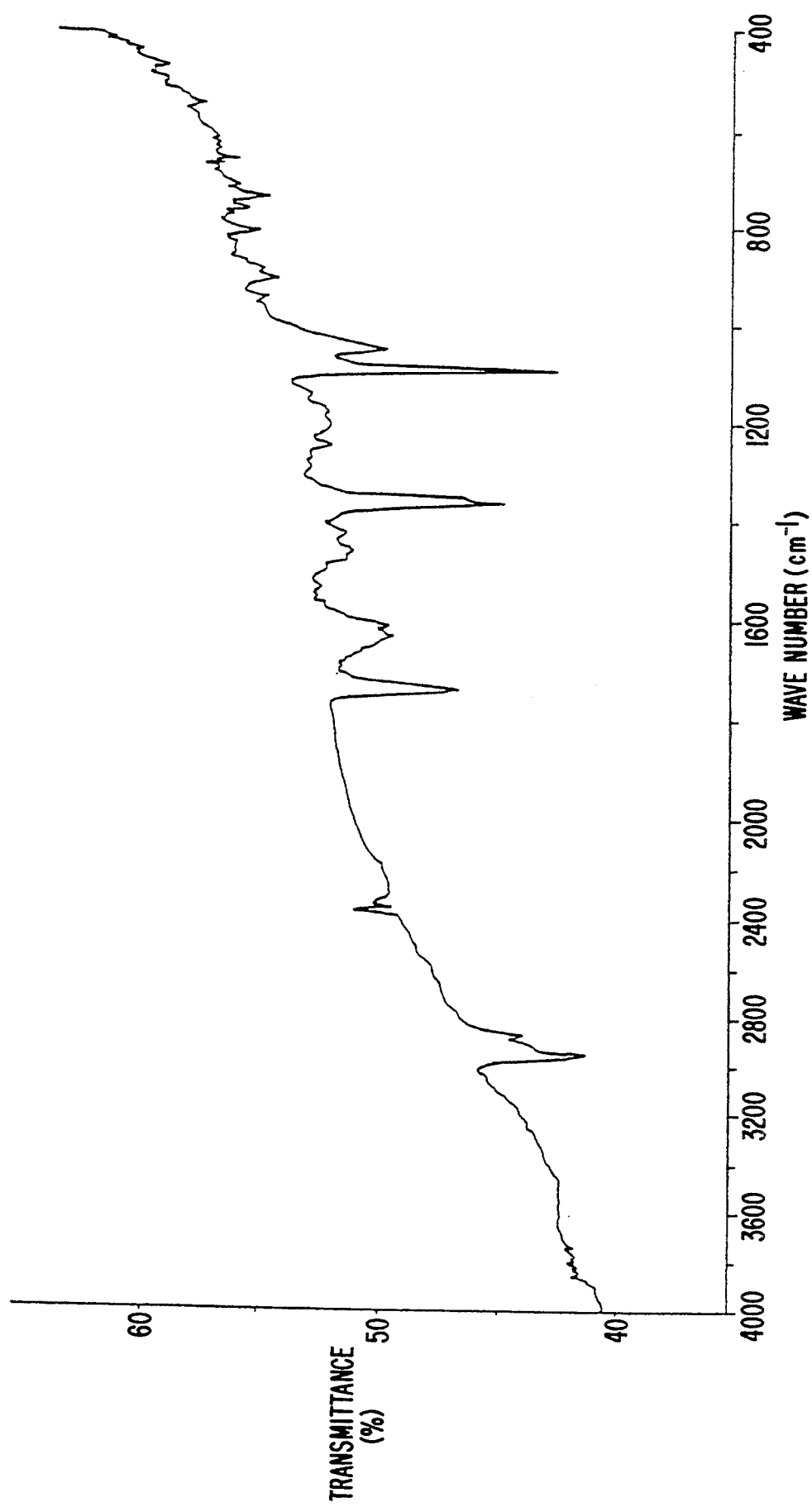

(5) IR spectrum (KBr) is shown in FIG. 28.

Synthetic Example 13

[Synthesis of methyl 3,4-dimethylbenzoate]

To 200 ml of methanol was added 47.6 g (0.317 mol) of 3,4-dimethylbenzoic acid, and the resulting mixture was refluxed for about 4 hours in the presence of about 6 ml of concentrated sulfuric acid with continuous extraction of water by use of Molecular Sieves 3A (a drying agent mfd. by Wako Pure Chemical Industries, Ltd.). After cooling, 600 ml of water was added and the resulting mixture was extracted three times with about 200 ml of benzene. The benzene solution thus obtained was washed three times with a saturated aqueous sodium hydrogencarbonate solution and then three times with water, and dried with anhydrous sodium sulfate. The benzene solution thus treated was concentrated and then distilled under reduced pressure to obtain 49.4 g of a colorless liquid at a boiling point of 133°-134° C./30 mmHg. This liquid was confirmed to be methyl 3,4-dimethylbenzoate from the following analysis results:

(1) Elementary analysis values:

|  | C | H |
| --- | --- | --- |
| Calculated (%) | 73.15 | 7.37 |
| Found (%) | 73.13 | 7.46 |

(2) NMR spectrum values: $CDCl_3$ δ values 7.81 (1H, br-s) 7.76 (1H, dd, J=7.93, 1.53 Hz) 7.18 (1H, d, J=7.93 Hz) 3.89 (3H, s) 2.30 (6H, s)

Figure 29:
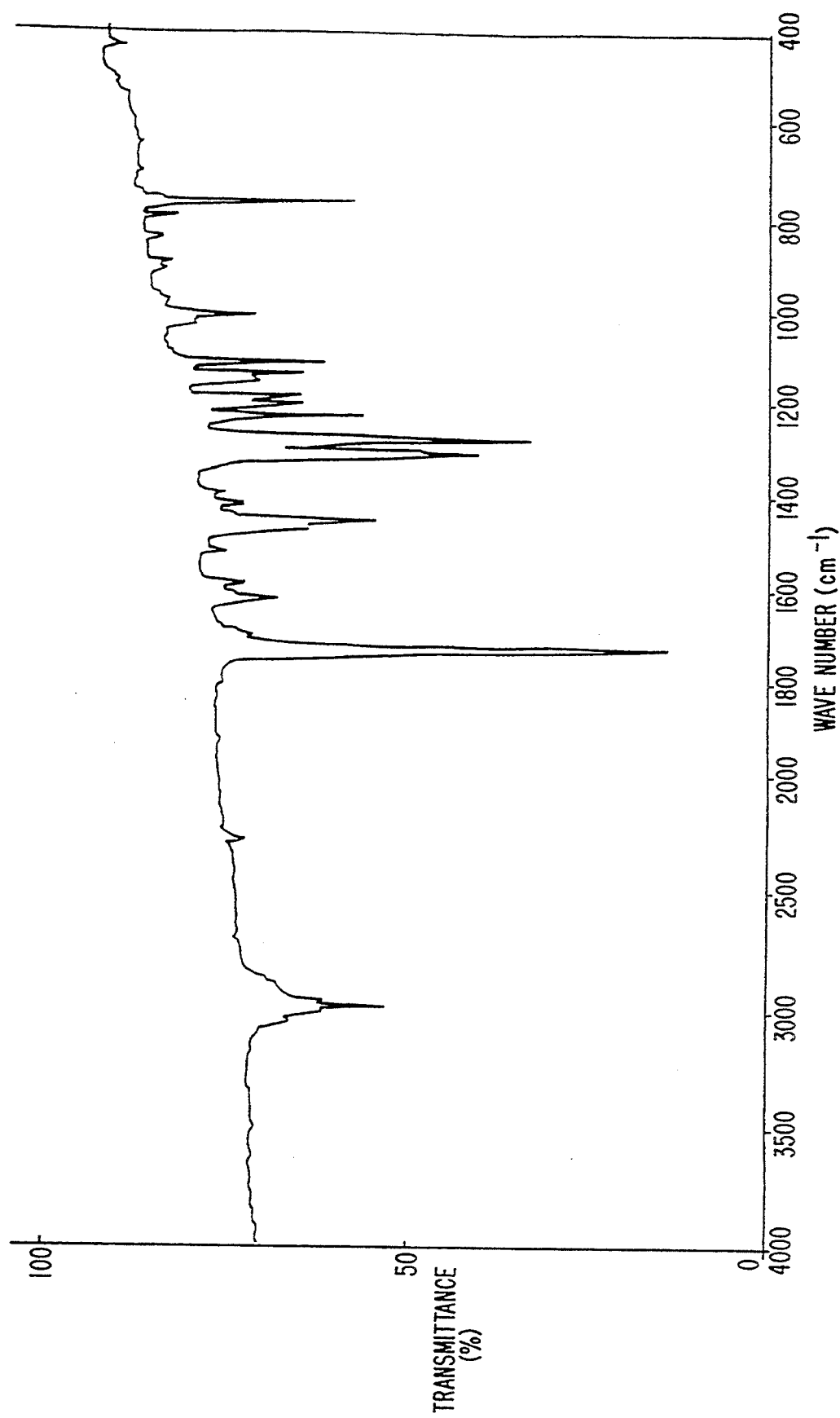

(3) IR spectrum (neat) is shown in FIG. 29.

The spectrum shows an absorption due to ester C=O stretching vibration near 1710 $cm^{-1}$.

Synthetic Example 14

[Synthesis of 6-methoxycarbonyl-2,3-dicyanonaphthalene]

To a solution of 33.8 g (0.2 mol) of methyl 3,4-dimethylbenzoate and 142.2 g (0.8 mol) of N-bromosuccinimide in 500 ml of carbon tetrachloride was added 1 g of benzoyl peroxide, and the resulting mixture was irradiated by a 100-W high pressure mercury arc lamp for 8 to 12 hours under reflux. After cooling, the white crystals precipitated were removed by filtration and the carbon tetrachloride solution, i.e., the mother liquor was concentrated under reduced pressure. The solid thus obtained was recrystallized from hexane/methylene chloride to obtain 79 g of methyl 3,4-bis(dibromomethyl)benzoate as colorless crystals. Physical properties of methyl 3,4-bis(dibromomethyl)benzoate were as follows:

(1) Melting point: 99.5°-100.5° C.
(2) Elementary analysis values:

|  | C | H | Br |
| --- | --- | --- | --- |
| Calculated (%) | 25.03 | 1.68 | 66.62 |
| Found (%) | 25.07 | 1.54 | 65.72 |

(3) NMR spectrum values: $CDCl_3$ δ values 8.29 (1H, br-s) 8.03 (1H, dd, J=8.24, 1.53 Hz) 7.81 (1H, d, J=8.24 Hz) 7.18 (1H, br-s) 7.09 (1H, br-s) 3.96 (3H, s)

Figure 30:
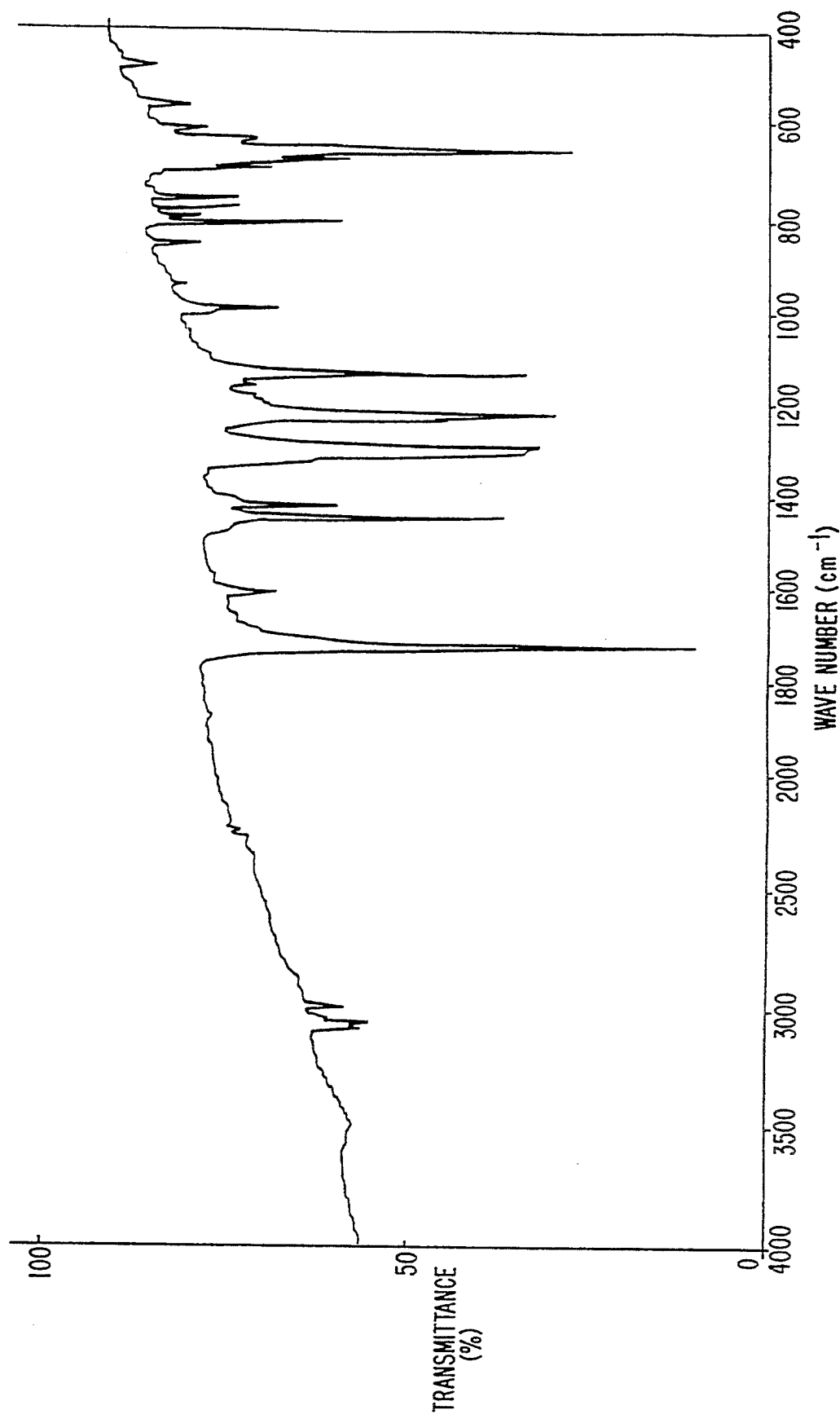

(4) IR spectrum (KBr) is shown in FIG. 30.

The spectrum shows an absorption due to ester C=O stretching vibration near 1705 $cm^{-1}$.

Next, 100 g (0.67 mol) of sodium iodide was added to a solution of 48 g (0.1 mol) of the methyl 3,4-bis(dibromomethyl)benzoate obtained and 13.5 g (0.173 mol) of fumaronitrile in 400 ml of anhydrous N,N-dimethylformamide with sufficient stirring, and the resulting mixture was stirred under nitrogen at about 75° C. After completion of the reaction, the reaction mixture was poured onto about 2 kg of ice. Sodium hydrogensulfite was slowly added until the reddish-brown aqueous solution thus obtained turned light-yellow. Sodium hydrogensulfite was added in a slight excess and after stirring for a while, the resulting mixture was allowed to stand overnight at room temperature. The light-yellow solid precipitated was filtered and sufficiently washed with water and then methanol. The light-yellow solid was recrystallized from acetone/methanol to obtain 13.9 g of colorless needles. The crystals were confirmed to be 6-methoxycarbonyl-2,3-dicyanonaphthalene from the following analysis results:

(1) Melting point: 264°-265° C.
(2) Elementary analysis values:

|  | C | H | N |
| --- | --- | --- | --- |
| Calculated (%) | 71.18 | 3.41 | 11.86 |
| Found (%) | 71.21 | 3.37 | 11.87 |

(3) NMR spectrum values: $CDCl_3$ δ values 8.72 (1H, br-s) 8.47 (1H, s) 8.41 (1H, s) 8.38 (1H, dd, J=8.55, 1.53 Hz) 8.06 (1H, d, J=8.55 Hz) 4.04 (3H, s)

Figure 31:
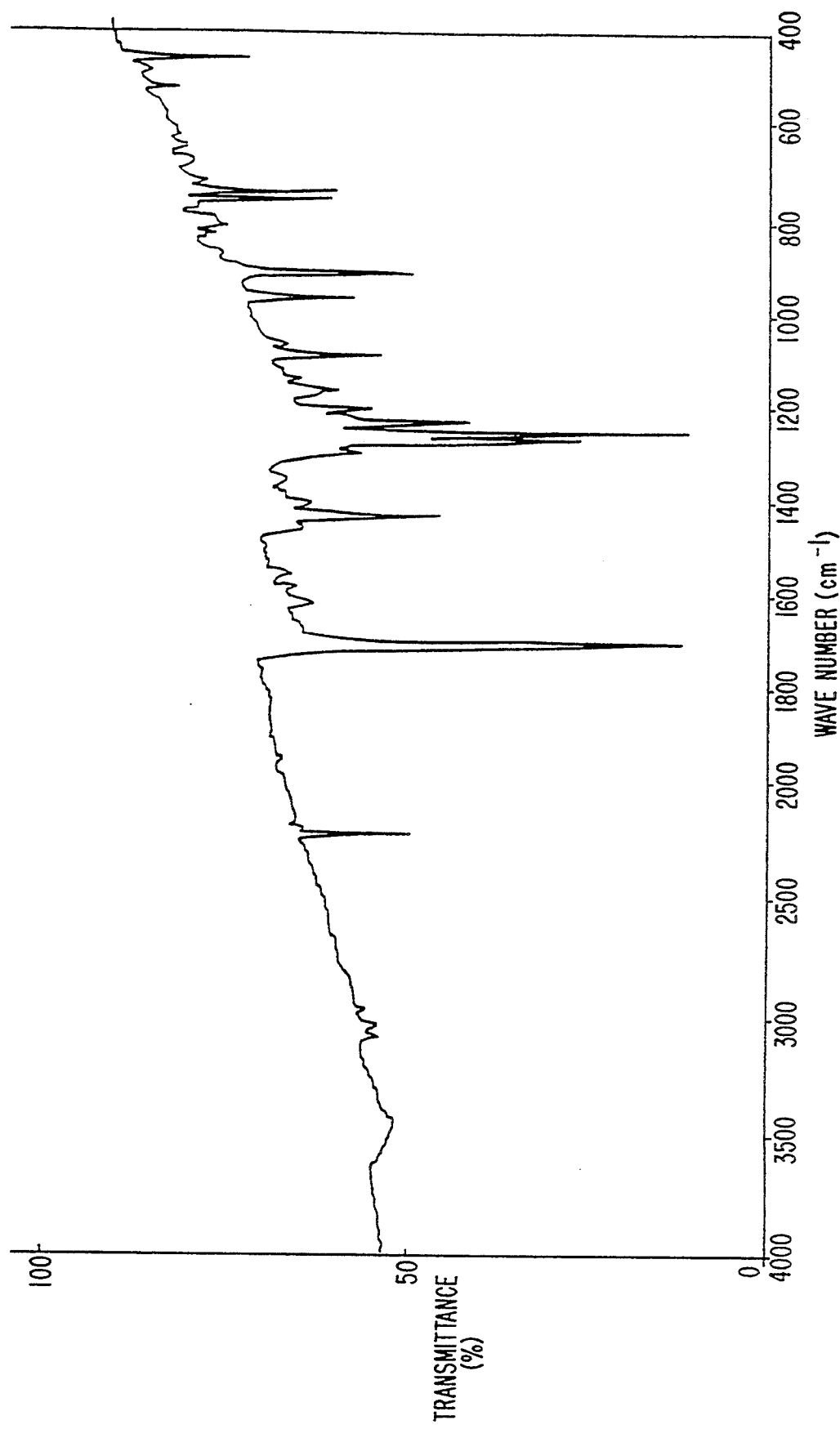

(4) IR spectrum (KBr) is shown in FIG. 31.

The spectrum shows an absorption due to ester C=O stretching vibration near 1700 $cm^{-1}$.

Synthetic Example 15

[Synthesis of n-amyl 3,4-dimethylbenzoate]

To 150 ml of benzene were added 60 g (0.4 mol) of 3,4-dimethylbenzoic acid, 43 ml (0.4 mol) of n-amyl alcohol and 22 g (0.116 mol) of p-toluenesulfonic acid monohydrate, and the resulting mixture was refluxed for 6 hours with continuous extraction of water using a Dean-Stark trap and then Molecular Sieves 3A. After cooling, the reaction mixture was washed three times with 100 ml of a saturated aqueous sodium hydrogencarbonate solution and then three times with water. The benzene solution was then dried over anhydrous magnesium sulfate and concentrated under reduced pressure. The resulting oil thus obtained was distilled under reduced pressure to obtain 77 g of a colorless liquid at 145°-148° C./8 mmHg. This liquid was confirmed to be n-amyl 3,4-dimethylbenzoate from the following analysis results:

(1) Elementary analysis values:

|  | C | H |
| --- | --- | --- |
| Calculated (%) | 76.33 | 9.15 |
| Found (%) | 76.22 | 9.25 |

(2) NMR spectrum values: $CDCl_3$ δ values 7.81 (1H, br-s) 7.77 (1H, dd, J=7.94, 1.98 Hz) 7.18 (1H, d, J=7.94 Hz) 4.29 (2H, t, J=6.72 Hz) 2.30 (6H, s) 1.76 (2H, quintet, J=6.72 Hz) 1.40 (4H, m) 0.93 (3H, t, J=6.72 Hz)

Figure 32:
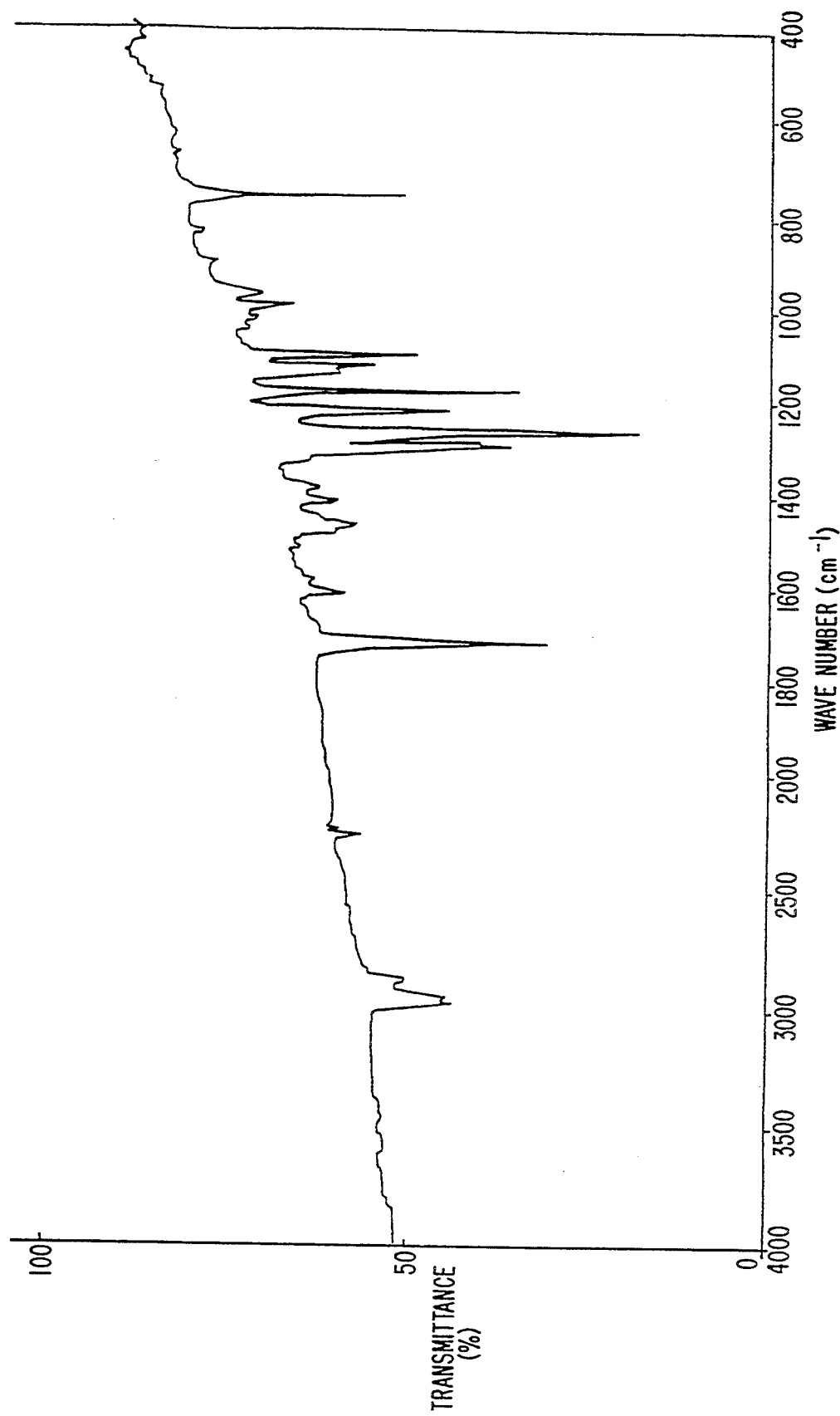

(3) IR spectrum (neat) is shown in FIG. 32.

The spectrum shows an absorption due to ester C=O stretching vibration near 1710 $cm^{-1}$.

Synthetic Example 16

[Synthesis of 6-(n-amyloxycarbonyl)-2,3-dicyanonaphthalene]

To a solution of 44.1 g (0.2 mol) of n-amyl 3,4-dimethylbenzoate and 142.4 g (0.8 mol) of N-bromosuccinimide in 500 ml of carbon tetrachloride was added 1 g of benzoyl peroxide, and the resulting mixture was irradiated by a 100-W high pressure mercury arc lamp for 11 hours under reflux. After cooling, the white crystals precipitated were removed by filtration and the carbon tetrachloride solution, i.e., the mother liquor was sufficiently concentrated under reduced pressure. The light-brown oil obtained was dissolved in 800 ml of N,N-dimethylformamide. To the solution 27 g (0.346 mol) of fumaronitrile and 200 g (1.34 mols) of sodium iodide were added with sufficient stirring. The resulting mixture was stirred under nitrogen at 75° C. for about 7 hours. After completion of the reaction, the reaction mixture was poured onto about 4 kg of ice. Sodium hydrogensulfite was slowly added until the reddish-brown aqueous solution thus obtained turned light-yellow. Sodium hydrogensulfite was added in a slight excess and stirred for a while. The resulting mixture was allowed to stand overnight at room temperature. The light-yellow solid precipitated was filtered, sufficiently washed with water, and then washed several times with methanol. The light-yellow solid was dissolved in about 500 ml of chloroform, and the chloroform layer was separated from the aqueous layer and then dried over anhydrous magnesium sulfate. The chloroform solution was concentrated under reduced pressure, and two times of recrystallization from chloroform/ethanol gave 20 g of colorless needles. The crystals were confirmed to be 6-(n-amyloxycarbonyl)-2,3-dicyanonaphthalene from the following analysis results:

(1) Melting point: 150°–152° C.
(2) Elementary analysis values:

|  | C | H | N |
| --- | --- | --- | --- |
| Calculated (%) | 73.95 | 5.52 | 9.52 |
| Found (%) | 73.82 | 5.38 | 9.51 |

(3) NMR spectrum values: CDCl$_3$ δ values 8.70 (1H, br-s) 8.49 (1H, s) 8.41 (1H, s) 8.38 (1H, dd, J=8.55, 1.53 Hz) 8.06 (1H, d, J=8.55 Hz) 4.43 (2H, t, J=6.72 Hz) 1.84 (2H, quitet, J=6.72 Hz) 1.44 (1H, m) 0.96 (3H, t, J=6.72 Hz)

Figure 33:
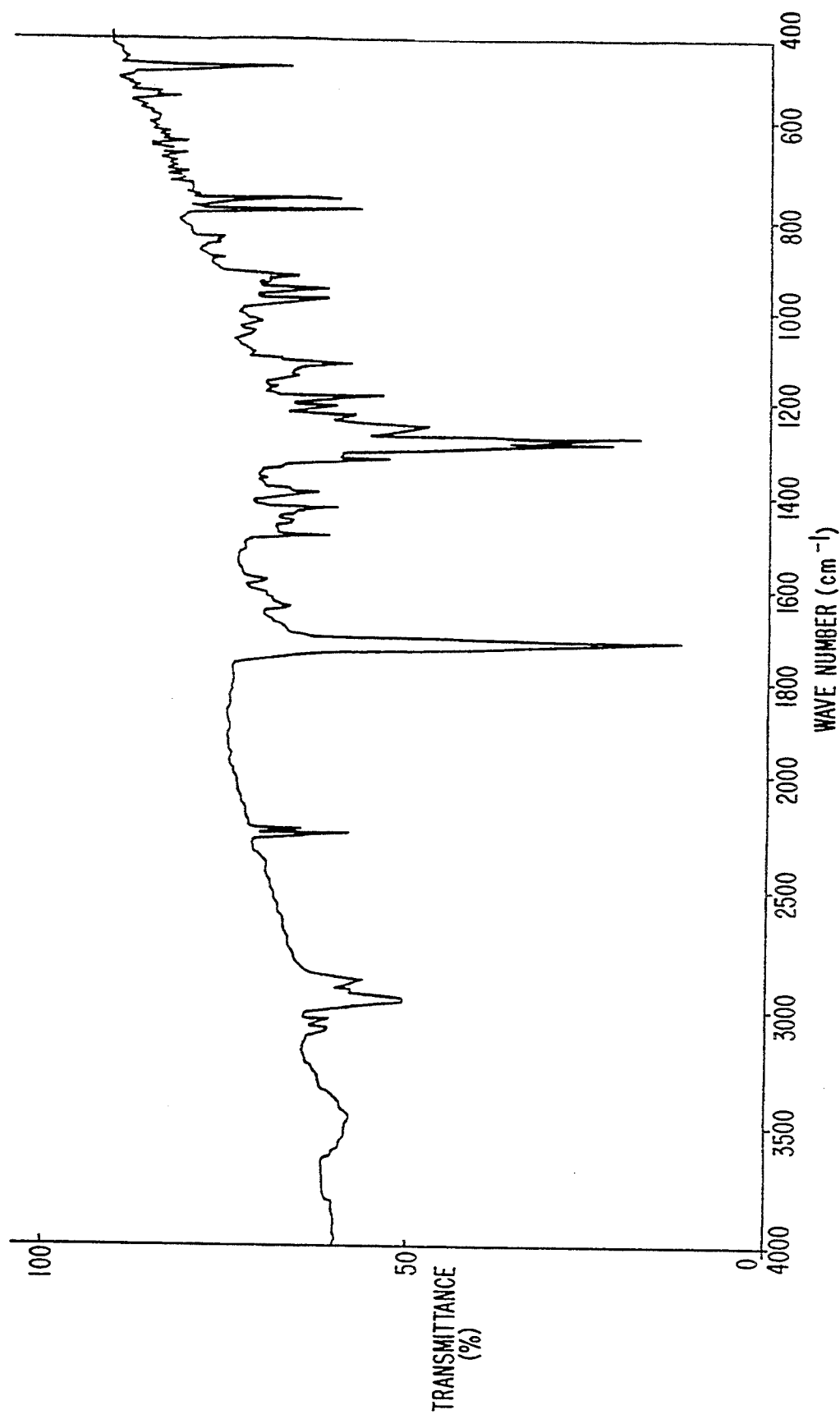

(4) IR spectrum (KBr) is shown in FIG. 33.

The spectrum shows an absorption due to ester C=O stretching vibration near 1700 cm$^{-1}$.

Synthetic Example 17

[Synthesis of n-octyl 3,4-dimethylbenzoate]

To 100 ml of benzene were added 40 g (0.27 mol) of 3,4-dimethylbenzoic acid, 100 ml (0.635 mol) of n-octanol and 22 g (0.116 mol) of p-toluenesulfonic acid monohydrate, and the resulting mixture was refluxed for about 6 hours with continuous extraction of water using a Dean-Stark trap and then Molecular Sieves 3A. After cooling, the reaction-mixture was treated in the same manner as in Synthetic Example 15, and distillation under reduced pressure gave 60.5 g of a colorless liquid at a boiling point of 148°–152° C./3 mmHg. This liquid was confirmed to be n-octyl 3,4-dimethylbenzoate from the following analysis results:

(1) Elementary analysis values:

|  | C | H |
| --- | --- | --- |
| Calculated (%) | 77.82 | 9.99 |
| Found (%) | 77.21 | 10.07 |

(2) NMR spectrum values: CDCl$_3$ δ values 7.81 (1H, br-s) 7.77 (1H, dd, J=7.63, 1.83 Hz) 7.19 (1H, d, J=7.63 Hz) 4.29 (2H, t, J=6.72 Hz) 2.31 (6H, s) 1.76 (2H, quintet, J=6.72 Hz) 1.1–1.5 (10H, m) 0.88 (3H, t, J=6.72 Hz)

Figure 34:
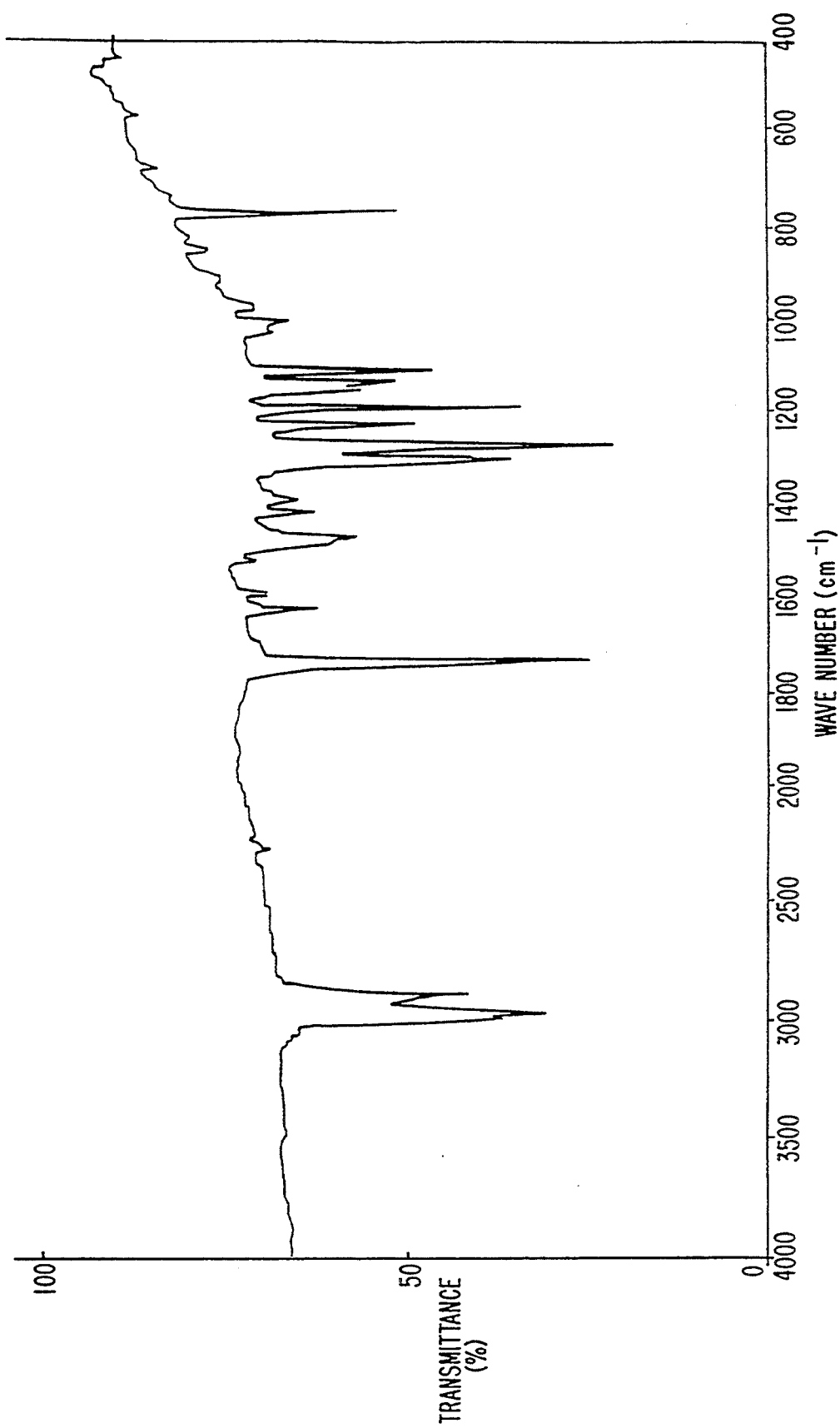

(3) IR spectrum (neat) is shown in FIG. 34.

The spectrum shows an absorption due to ester C=O stretching vibration near 1710 cm$^{-1}$.

Synthetic Example 18

[Synthesis of 6-(n-octyloxycarbonyl)-2,3-dicyanonaphthalene]

To a solution of 52.5 g (0.2 mol) of n-octyl 3,4-dimethylbenzoate and 142.2 g (0.8 mol) of N-bromosuccinimide in 500 ml of carbon tetrachloride was added 1 g of benzoyl peroxide, and the resulting mixture was irradiated by a 100-W high pressure mercury arc lamp for about 11 hours under reflux. After cooling, the reaction mixture was treated in the same manner as in Synthetic Example 16, followed by reaction with fumaronitrile, treatment in the same manner as in Synthetic Example 16, and several times of recrystallization from chloroform/ethanol, whereby about 7 g of colorless reedles were obtained. The crystals were confirmed to be 6-(n-octyloxycarbonyl)-2,3-dicyanonaphthalene from the following analysis results:

(1) Melting point: 142°–144° C.
(2) Elementary analysis values:

|  | C | H | N |
| --- | --- | --- | --- |
| Calculated (%) | 75.42 | 6.63 | 8.38 |
| Found (%) | 75.20 | 6.41 | 7.99 |

(3) NMR spectrum values: CDCl$_3$ δ values 8.70 (1H, br-s) 8.49 (1H, s) 8.42 (1H, s) 8.38 (1H, dd, J=8.55, 1.52 Hz) 8.06 (1H, d, J=8.55 Hz) 4.42 (2H, t, J=6.72 Hz) 1.83 82H, quintet, J=6.72 Hz) 1.2–1.6 (10H, m) 0.89 (3H, t, J=6.72 Hz)

(4) IR spectrum (KBr) is shown in FIG. 35.

The spectrum shows an absorption due to ester C=O stretching vibration near 1700 cm$^{-1}$.

Synthetic Example 19

[Synthesis of tetra(n-amyloxycarbonyl)zinc naphthalocyanine]

1.46 Grams (5 mmols) of 6-(n-amyloxycarbonyl)-2,3-dicyanonaphthalene, 105 mg (1.6 mmols) of powdered zinc, 10 mg of ammonium molybdate and 5 g of urea were reacted with one another with sufficient stirring at about 220° C. for about 2.5 hours. After cooling, 40 ml of hydrochloric acid was added to the reaction mixture solidified to loosen the mixture to a certain extent, followed by sufficient stirring at about 50° C. for 30 minutes. After the stirring, the insoluble materials were filtered and sufficiently washed successively with water, methanol and acetone. From the solid thus obtained, impurities were extracted by means of a Soxhlet extractor for about 50 hours using a mixed solvent of methanol and acetone (1:1). Next, Soxhlet extraction was carried out for 20 hours by using chloroform in place of the mixed solvent. The dark-green chloroform solution thus obtained was filtered with heating, after which the residue was concentrated to dryness under reduced pressure to obtain 937 mg of lustrous, black crystals. The crystals were confirmed to be tetra(n-amyloxycarbonyl)zinc naphthalocyanine from the following analysis results:

(1) Melting point: >300° C.
(2) Elementary analysis values:

|  | C | H | N |
| --- | --- | --- | --- |
| Calculated (%) | 70.04 | 5.22 | 9.08 |
| Found (%) | 69.35 | 5.22 | 9.08 |

Figure 36:
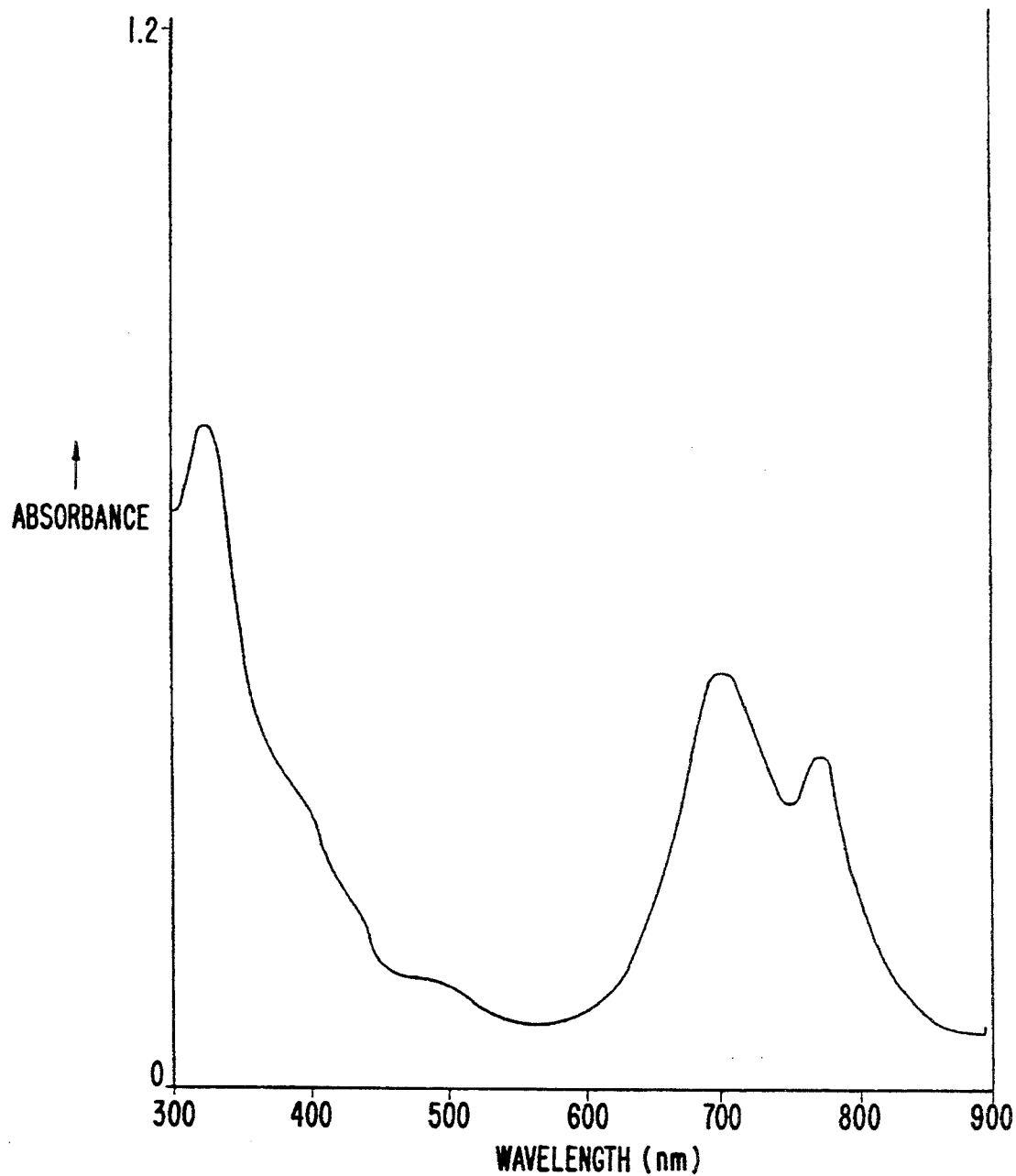

(3) Electronic spectrum (CHCl₃ solution) is shown in FIG. 36.

Figure 37:
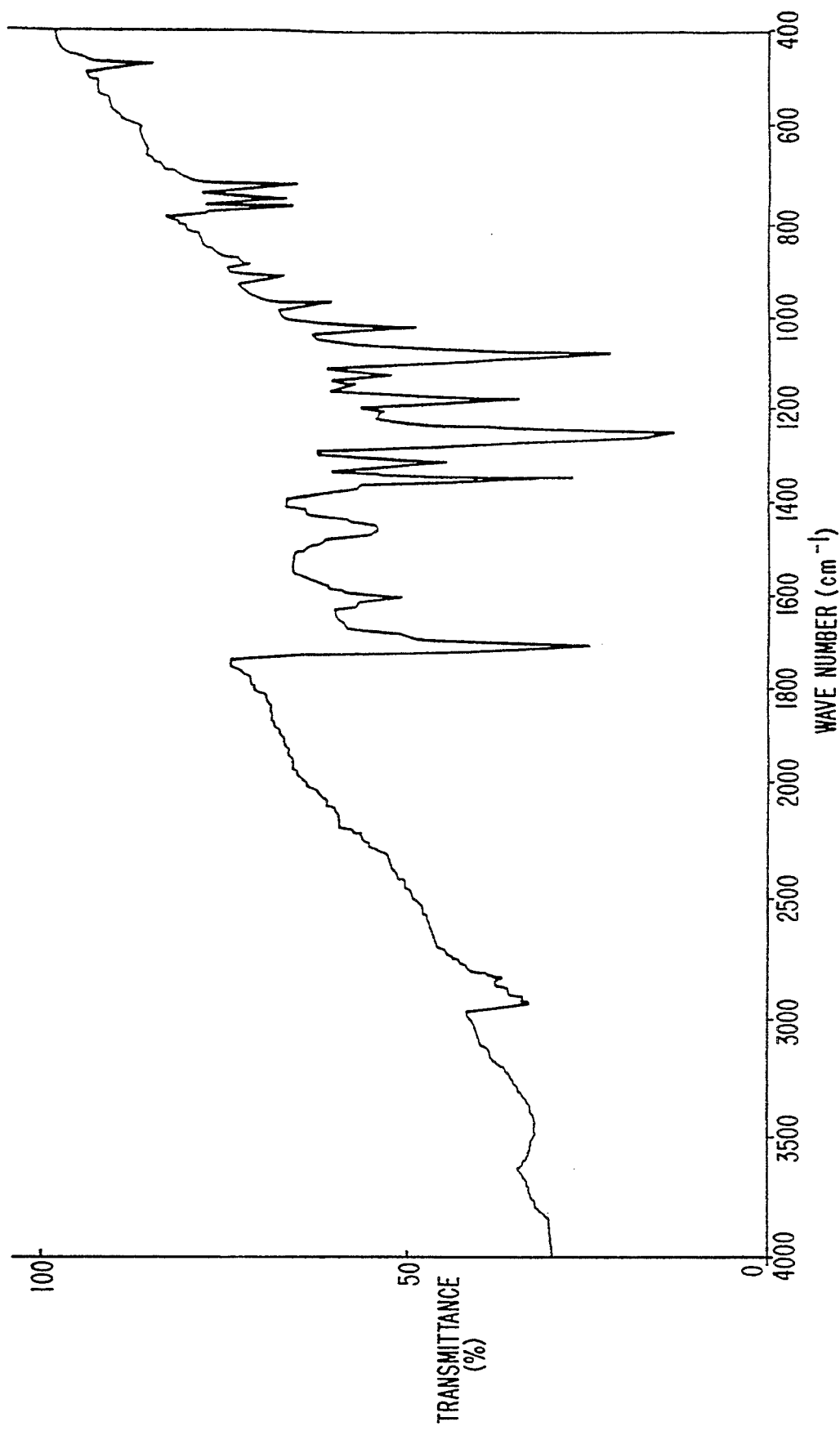

(4) IR spectrum (KBr) is shown in FIG. 37.

The spectrum shows an absorption due to ester C=O stretching vibration near 1700 cm⁻¹.

Synthetic Example 20

[Synthesis of tetra(n-octyloxycarbonyl)chloroaluminum naphthalocyanine]

1.67 Grams (5 mmols) of 6-(n-octyloxycarbonyl)-2,3-dicyanonaphthalene, 213 mg (1.6 mmols) of aluminum chloride, 10 mg of ammonium molybdate and 5 g of urea were reacted with one another with sufficient stirring at about 220° C. for about 2.5 hours. After cooling, 40 ml of methanol was added to the reaction mixture solidified to loosen the mixture to a certain extent, followed by sufficient stirring at about 50° C. for 30 minutes. After the stirring, the insoluble materials were filtered and sufficiently washed with methanol and then acetone. From the solid thus obtained, impurities were extracted by means of a Soxhlet extractor with methanol for about 100 hours and then with acetone for about 50 hours. Next, Soxhlet extraction was carried out for about 20 hours using chloroform in place of the above solvents. The dark-green chloroform solution thus obtained was filtered with heating, after which the residue was concentrated to dryness under reduced pressure to obtain 243 mg of lustrous, black crystals. The crystals were confirmed to be tetra(n-octyloxycarbonyl) chloroaluminum naphthalocyanine from the following analysis results:

(1) Melting point: >300° C.

(2) Elementary analysis values:

|  | C | H | N | Cl |
|---|---|---|---|---|
| Calculated (%) | 72.06 | 6.34 | 8.00 | 2.53 |
| Found (%) | 71.81 | 6.27 | 7.74 | 2.07 |

Figure 38:
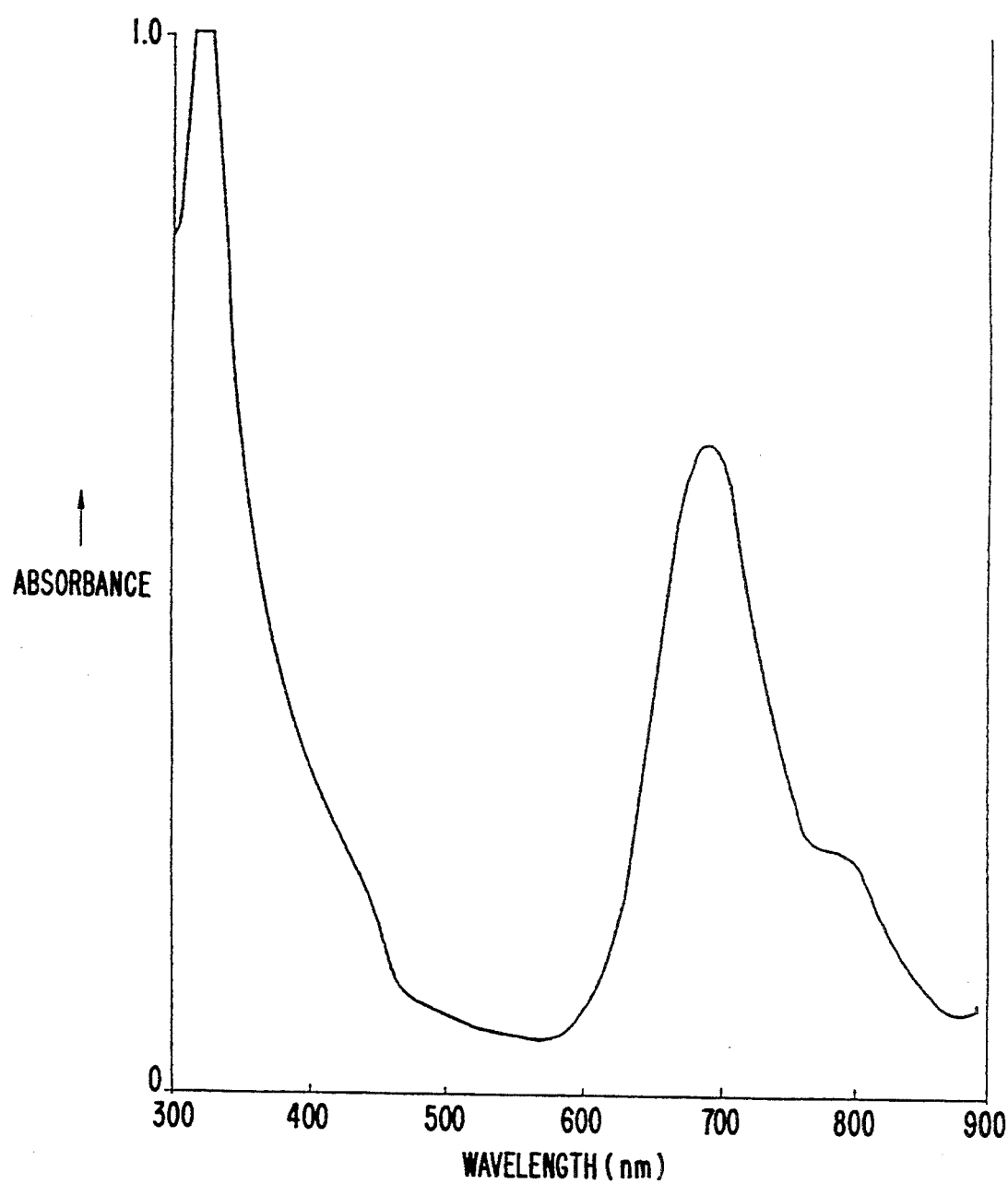

(3) Electronic spectrum (CHCl₃ solution) is shown in FIG. 38.

Figure 39:
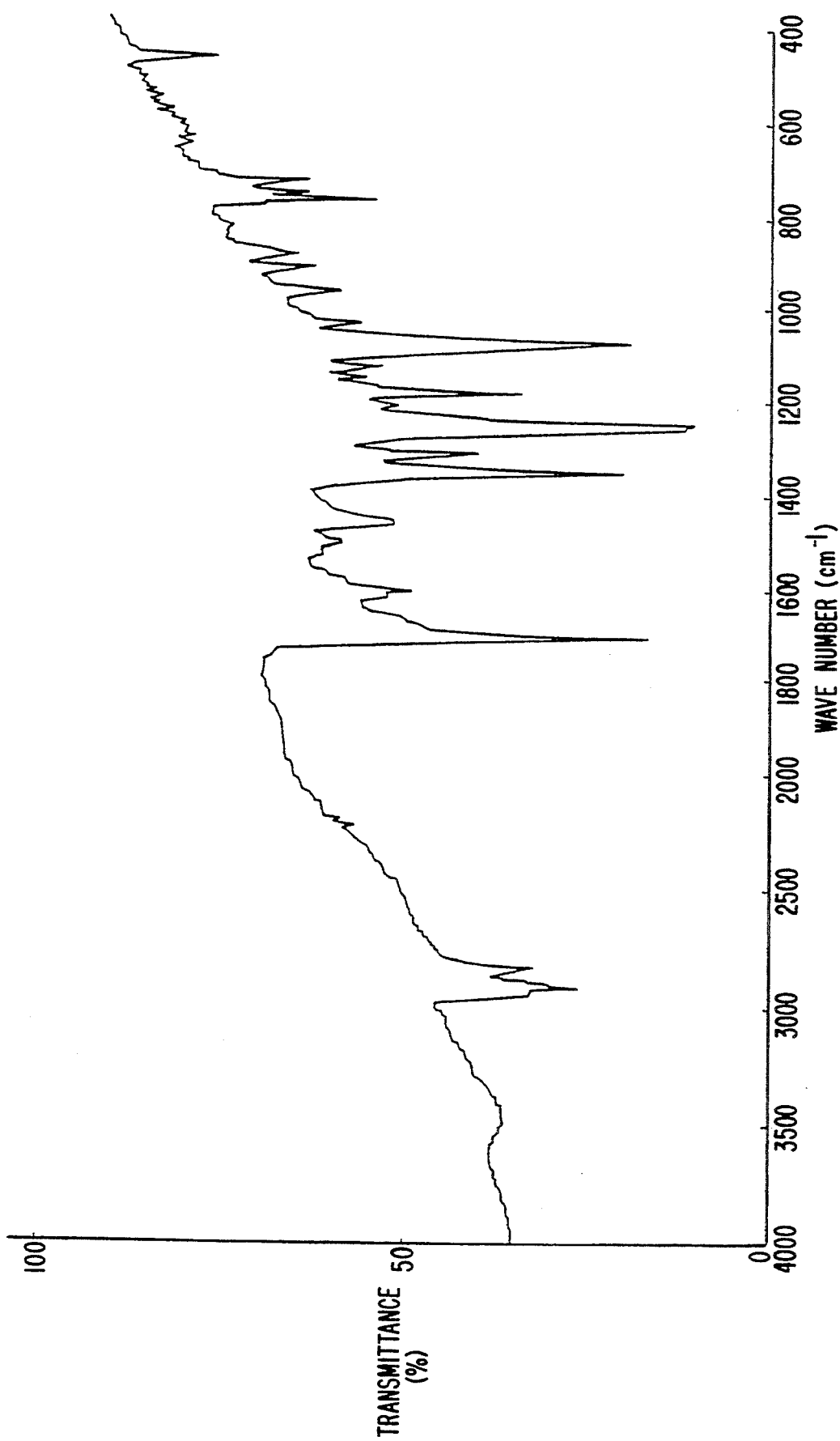

(4) IR spectrum (KBr) is shown in FIG. 39.

The spectrum shows an absorption due to ester C=O stretching vibration near 1700 cm⁻¹.

Synthetic Example 21

[Synthesis of 6-chloro-2,3-dicyanoquinoxaline]

To 300 ml of ethyl acetate were added 5 g (46.3 mmols) of diaminomaleonitrile, 5 g (41.5 mmols) of anhydrous magnesium sulfate and 15 g (170.3 mmols) of activated manganese dioxide, followed by ultrasonication at about 45° C. for about 30 hours. The reaction mixture was filtered and the filtrate was sufficiently washed with ethyl acetate. The light-yellow mother liquor was concentrated, followed by separation and purification by a silica gel chromatography (eluent: hexane/ethyl acetate=75/25), whereby 2.90 g (59%) of diiminosuccinonitrile was obtained as colorless crystals.

A mixture of 0.5 g (4.7 mmols) of the diiminosuccinonitrile and 0.67 g (4.7 mmols) of 4-chloro-1,2-phenylenediamine was slowly added to 10 ml of trifluoroacetic acid at about 20° C. over a period of 30 minutes, and the resulting mixture was stirred at room temperature for 8 hours and then allowed to stand overnight. To the reaction mixture was added 50 ml of water, and the solid precipitated was filtered and sufficiently washed with water. The solid thus obtained was dried under reduced pressure, followed by a silica gel column chromatography (eluent: hexane/ethyl acetate (75/25)) and then recrystallization from chloroform/ethanol, wherein 0.6 g (59%) of 6-chloro-2,3-dicyanoquinoxaline was obtained as colorless crystals.

(1) NMR spectrum values: CDCl₃ δ values 8.28 (1H, d, J=2.13 Hz) 8.23 (1H, d, J=9.16 Hz) 8.04 (1H, dd, J=9.16, 2.13 Hz)

(2) Melting point: 188°-189° C.

Figure 40:
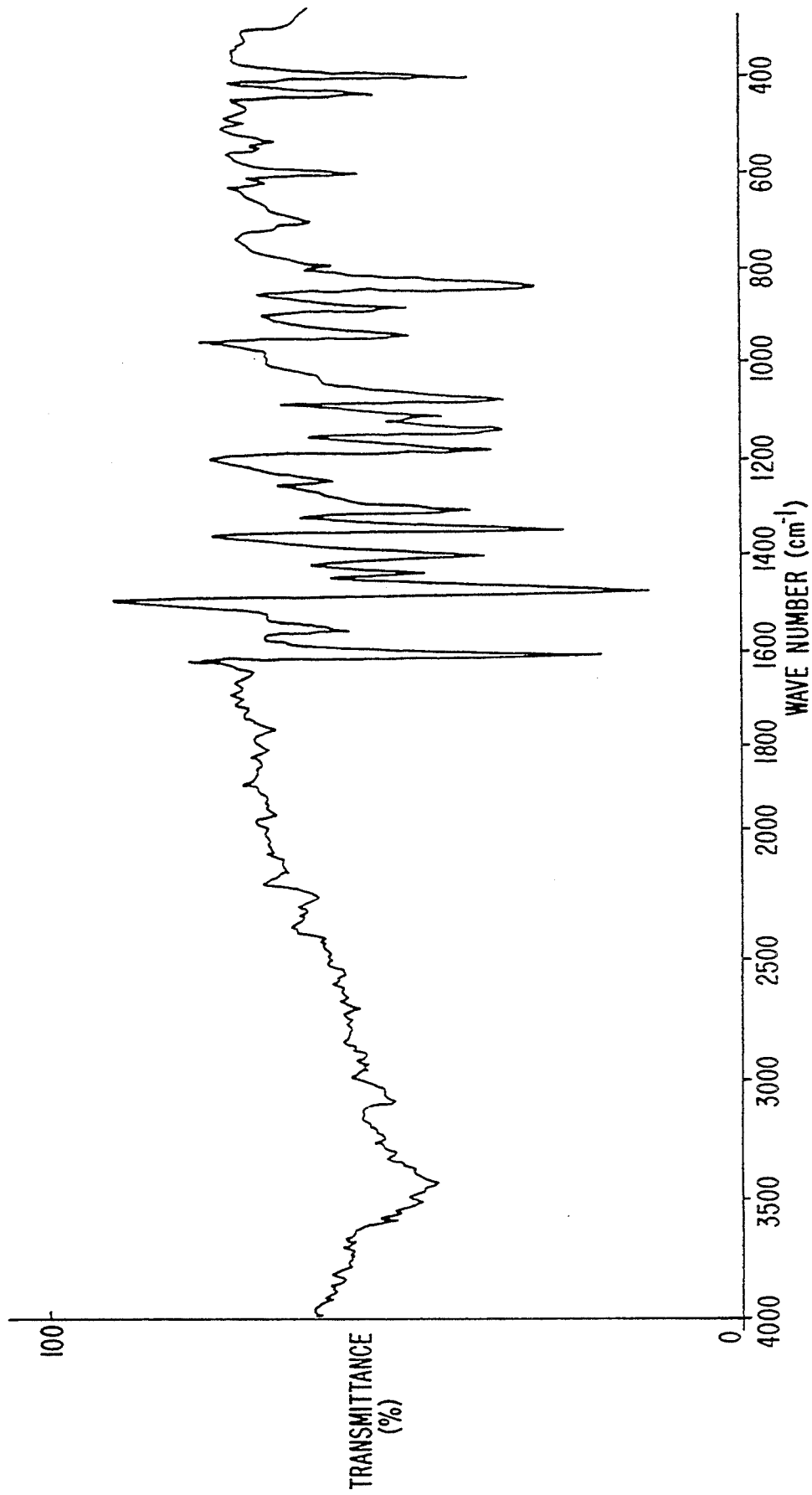

(3) IR spectrum (KBr) is shown in FIG. 40.

Synthetic Example 22

[Synthesis of dihydroxysilicon-tetrachloroquinoxalocyanine]

Under nitrogen, 5.97 g (27.8 mmols) of 6-chloro-2,3-dicyanoquinoxaline was added to a solution of sodium methoxide in methanol prepared by adding 0.12 g (5.4 mmols) of metallic sodium to 72 ml of absolute methanol, and anhydrous ammonia gas was bubbled into the resulting mixture with sufficient stirring at room temperature for about 1 hour. The mixture was refluxed for about 3 hours, while bubbling therethrough anhydrous ammonia gas. After cooling, the reaction mixture was filtered and the residue was sufficiently washed with methanol and dried under reduced pressure to obtain 5.23 g of isoindoline derivative of 6-chloro-2,3-dicyanoquinoxaline as a light-gray solid. The isoindoline derivative was used in the subsequent reaction without further purification.

Under nitrogen, 10 ml (90 mmols) of silicon tetrachloride was added to a suspension of 5.1 g (22.0 mmols) of the above isoindoline derivative in 108 ml of anhydrous quinoline, and the resulting mixture was refluxed for about 3 hours. After cooling, the reaction mixture was poured into 300 ml of methanol, and the resulting mixture was allowed to stand overnight at room temperature. The solid precipitated was filtered, sufficiently washed with methanol, and then dried under reduced pressure to obtain a black solid quantitatively. To 100 ml of ethanol were added 6 g of the black solid and then 100 ml of aqueous ammonia, and the resulting mixture was refluxed for about 5 hours. After cooling, the reaction mixture was filtered and the residue was sufficiently washed with methanol and then dried under reduced pressure to obtain 4.5 g of a black solid. The black solid was considered dihydroxysilicon-tetrachloroquinoxalocyanine and used in the subsequent reaction without further purification.

Synthetic Example 23

[Synthesis of bis(tributylsiloxy)silicon-tetrachloroquinoxalocyanine]

Figure 41:
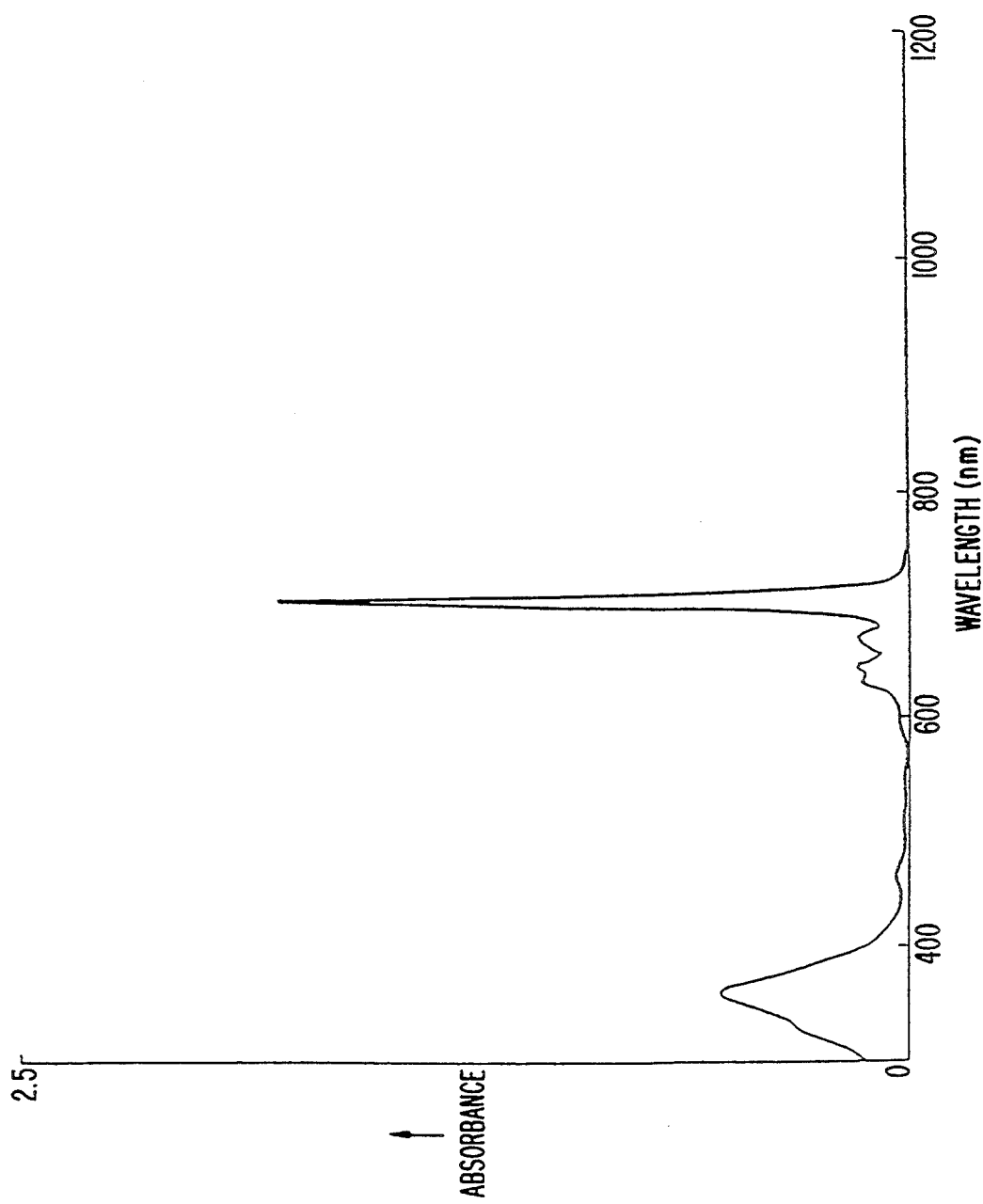

1 Gram (1.09 mmols) of dihydroxysilicon-tetrachloroquinoxalocyanine and 2 ml (9.24 mmols) of tributylsilanol were stirred in 20 ml of quinoline at 200° C. for 4 hours. After cooling, the reaction mixture was poured into 100 ml of methanol, and the resulting mixture was sufficiently stirred and then allowed to stand. The solid precipitated was filtered and sufficiently washed with methanol. With hot chloroform, only a soluble material in the solid was extracted, and the chloroform solution thus obtained was subjected to alumina column chromatography, followed by recrystallization from chloroform-methanol, whereby 108 mg of dark-green crystals were obtained. The dark-green crystals were confirmed to be bis(tributylsiloxy)silicon-tetrachloroquinoxalocyanine from their electronic spectrum (FIG. 41).

Elementary analysis values:

|  | C | H | N | Cl |
|---|---|---|---|---|
| Calculated (%) | 58.35 | 5.05 | 17.01 | 10.76 |
| Found (%) | 58.51 | 5.08 | 17.32 | 10.99 |

Synthetic Example 24

[Synthesis of bis(tributylsiloxy)silicon-octabromophenanthracyanine]

1 Gram (0.62 mmol) of dihdyroxysilicon-octabromophenanthracyanine synthesized by use of 4-bromophenylacetonitrile as a starting material according to the method described in a reference (Synthetic Metals, vol. 9, p. 329–340 (1984)) and Synthetic Examples 3, 4 and 5, and 1 ml (4.62 mmols) of tributylsilanol were stirred in 20 ml of quinoline at 200° C. for 5 hours. After cooling, the reaction mixture was poured into 100 ml of methanol, and the resulting mixture was sufficiently stirred and then allowed to stand. The solid precipitated was filtered and sufficiently washed with methanol. Only a material soluble in hot chloroform was extracted from the solid with hot chloroform and recrystallized from chloroform to obtain 482 mg of dark-green crystals. The dark-green crystals were confirmed to be bis(tributylsiloxy)silicon-octabromophenanthracyanine from the following analysis results:

Elementary analysis values:

|  | C | H | N | Br |
|---|---|---|---|---|
| Calculated (%) | 52.77 | 3.92 | 5.59 | 31.92 |
| Found (%) | 52.54 | 3.87 | 5.46 | 32.11 |

Synthetic Example 25

[Synthesis of bis(tributylsiloxy)silicon-octabromoanthracyanine]

Dihydroxysilicon-octabromoanthracyanine was obtained in accordance with Synthetic Examples 3, 4 and 5 from 9,10-dibromo-2,3-dicyanoanthracene synthesized according to the methods described in references [Monatshefte für Chemie, vol. 117, p. 475–489 (1986), J. prakt Chem. vol. 329, p. S365–373 (1987) and Khim. Geterotsikl. Soedin p. 274–278 (1972)].

1 Gram (0.62 mmol) of the dihydroxysilicon-octabromoanthracyanine and 1 ml (4.62 mmols) of tributylsilanol were stirred in 20 ml of quinoline at 200° C. for 5 hours. After cooling, the reaction mixture was poured into 100 ml of methanol, and the resulting mixture was sufficiently stirred and then allowed to stand. The solid precipitated was filtered and sufficiently washed with methanol. Only a material soluble in hot chloroform was extracted from the solid with hot chloroform and recrystallized from chloroform to obtain 378 mg of dark-brown crystals. The dark-brown crystals were confirmed to be bis(tributylsiloxy)silicon-octabromoanthracyanine from the following analysis results:

Elementary analysis values:

|  | C | H | N | Br |
|---|---|---|---|---|
| Calculated (%) | 52.77 | 3.92 | 5.59 | 31.91 |
| Found (%) | 52.94 | 4.01 | 5.78 | 32.20 |

Synthetic Example 26

[Synthesis of bis(tributylsiloxy)silicon-tetrabromo(1,2-naphthalocyanine)]

Dihydroxysilicon-tetrabromo(1,2-naphthalocyanine) was obtained in accordance with Synthetic Examples 3, 4 and 5 from bromo-1,2-dicyanonaphthalene synthesized according to the method described in a reference [Chem. Ber., 121, 1479–1486 (1988)].

1 Gram (0.92 mmol) of the dihydroxysilicon-tetrabromo(1,2-naphthalocyanine) and 2 ml (9.24 mmols) of tributylsilanol were stirred in 20 ml of quinoline at 200° C. for 4 hours. After cooling, the reaction mixture was poured into 100 ml of methanol, and the resulting mixture was sufficiently stirred and then allowed to stand. The solid precipitated was filtered and sufficiently washed with methanol. Only a material soluble in hot chloroform was extracted from the solid with hot chloroform and recrystallized from chloroform to obtain 405 mg of dark-green crystals. The dark-green crystals were confirmed to be bis(tributylsiloxy)silicon-tetrabromo(1,2-naphthalocyanine) from the following analysis results:

Elementary analysis values:

|  | C | H | N | Br |
|---|---|---|---|---|
| Calculated (%) | 58.14 | 5.02 | 7.53 | 21.49 |
| Found (%) | 57.83 | 4.93 | 7.36 | 21.18 |

Synthetic Example 27

[Synthesis of bis(tributylsiloxy)silicon-tetrabromoquinolocyanine]

Dihydroxysilicon-tetrabromoquinolocyanine was obtained by treating 6-bromo-2,3-dicyanoquinoline synthesized according to the methods described in references [U.S. Pat. No. 4,459,409 (1984) and Khim. Geterotrikl, Soedin, p. 274–278 (1972)], in accordance with Synthetic Examples 3, 4 and 5.

Figure 42:
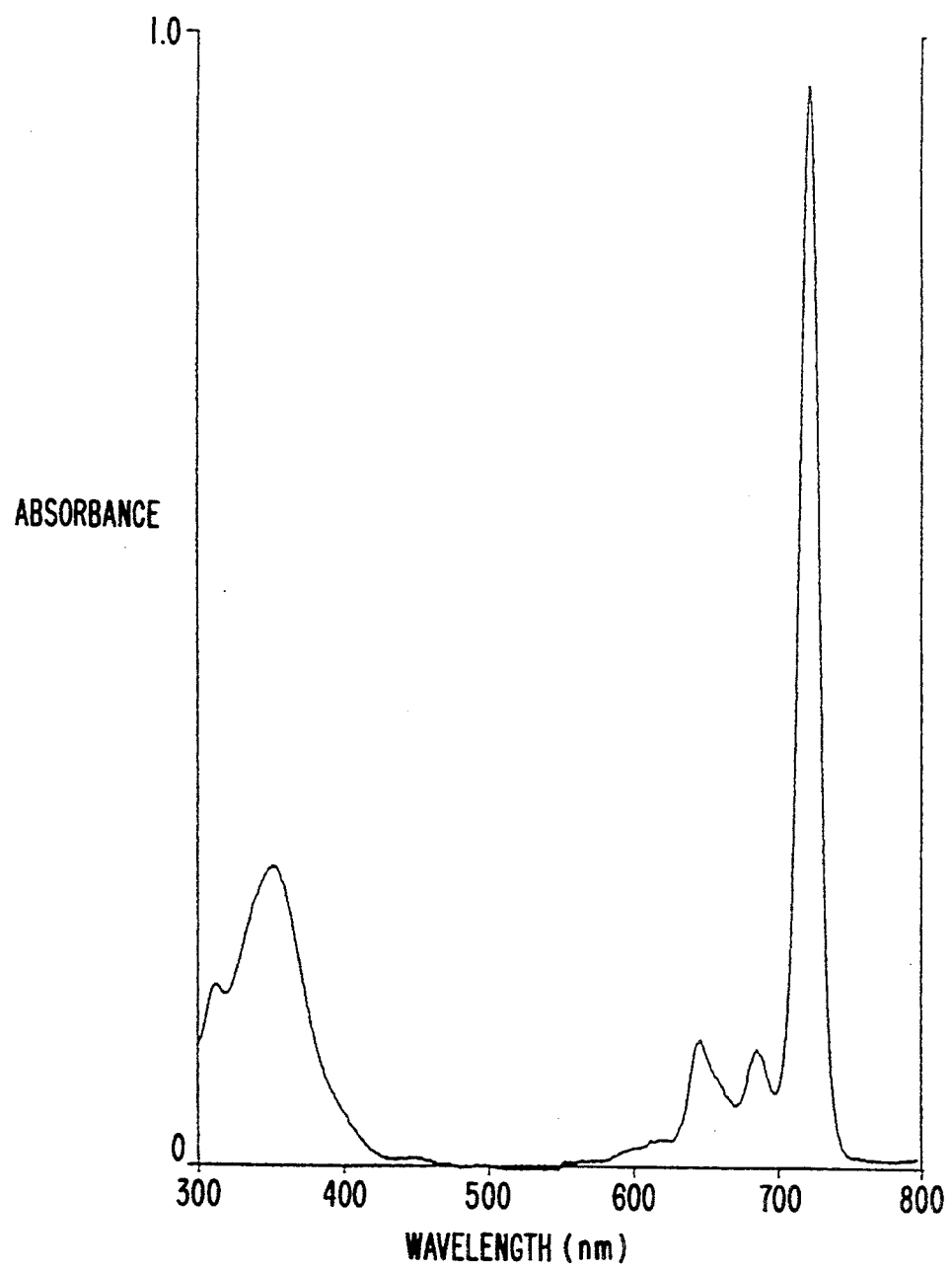

1 Gram (0.91 mmol) of the dihydroxysilicon-tetrabromoquinolocyanine and 2 ml (9.24 mmols) of tributylsilanol were stirred in 20 ml of quinoline at 200° C. for 5 hours. After cooling, the reaction mixture was poured into 100 ml of methanol, and the resulting mixture was sufficiently stirred and then allowed to stand. The solid precipitated was filtered and sufficiently washed with methanol. Only a material soluble in hot chloroform was extracted from the solid with hot chloroform and recrystallized from chloroform to obtain 452 mg of dark-green crystals. The dark-green crystals were confirmed to be bis(tributylsiloxy)silicon-tetrabromoquinolocyanine from their electronic spectrum (FIG. 42).

Elementary analysis values:

|  | C | H | N | Br |
|---|---|---|---|---|
| Calculated (%) | 54.77 | 4.73 | 11.27 | 21.43 |
| Found (%) | 54.85 | 4.76 | 11.34 | 21.27 |

Synthetic Example 28

[Synthesis of 2,3-dicyano-6-(3′,5′-dimethoxycarbonylphenylthio)naphthalene]

10 Grams (38.9 mmols) of the 6-bromo-2,3-dicyanonaphthalene obtained in Synthetic Example 2 and 12.9 g (44.7 mmols) of copper (I) 3,5-dimethoxycarbonylphenylthiolate were stirred in 200 ml of quinoline at 160° C. for 10 hours. After cooling, the reaction mixture was poured into 600 ml of methanol/water (1/1) and the resulting mixture was allowed to stand overnight. The precipitate formed was filtered and sufficiently washed with methanol. The solid thus obtained was transferred to a Soxhlet extractor and extracted with acetone for 20 hours. The acetone solution thus obtained was concentrated, after which methanol was added and the solid precipitated was filtered and sufficiently washed with methanol. The solid thus treated was purified by a silica gel column chromatography (eluent: ethyl acetate) and then recrystallized from acetone to obtain 4.32 g of colorless crystals. The crystals were confirmed to be 2,3-dicyano-6-(3',5'-dimethoxycarbonylphenylthio)naphthalene from the following analysis results:

(1) Melting point: 222°-224° C.
(2) Elementary analysis values:

|  | C | H | N | S |
|---|---|---|---|---|
| Calculated (%) | 65.66 | 3.51 | 6.96 | 7.97 |
| Found (%) | 65.93 | 3.60 | 7.18 | 8.02 |

(3) NMR spectrum values: $CDCl_3$ δ values: 8.71 (1H, t, J=1.53 Hz) 8.35 (2H, d, J=1.53 Hz) 8.29 (1H, br-s) 8.16 (1H, br-s) 7.88 (1H, d, J=8.55 Hz) 7.66 (1H, br-s) 7.58 (1H, dd, J=8.55, 1.83 Hz) 3.96 (6H, s)

Figure 43:
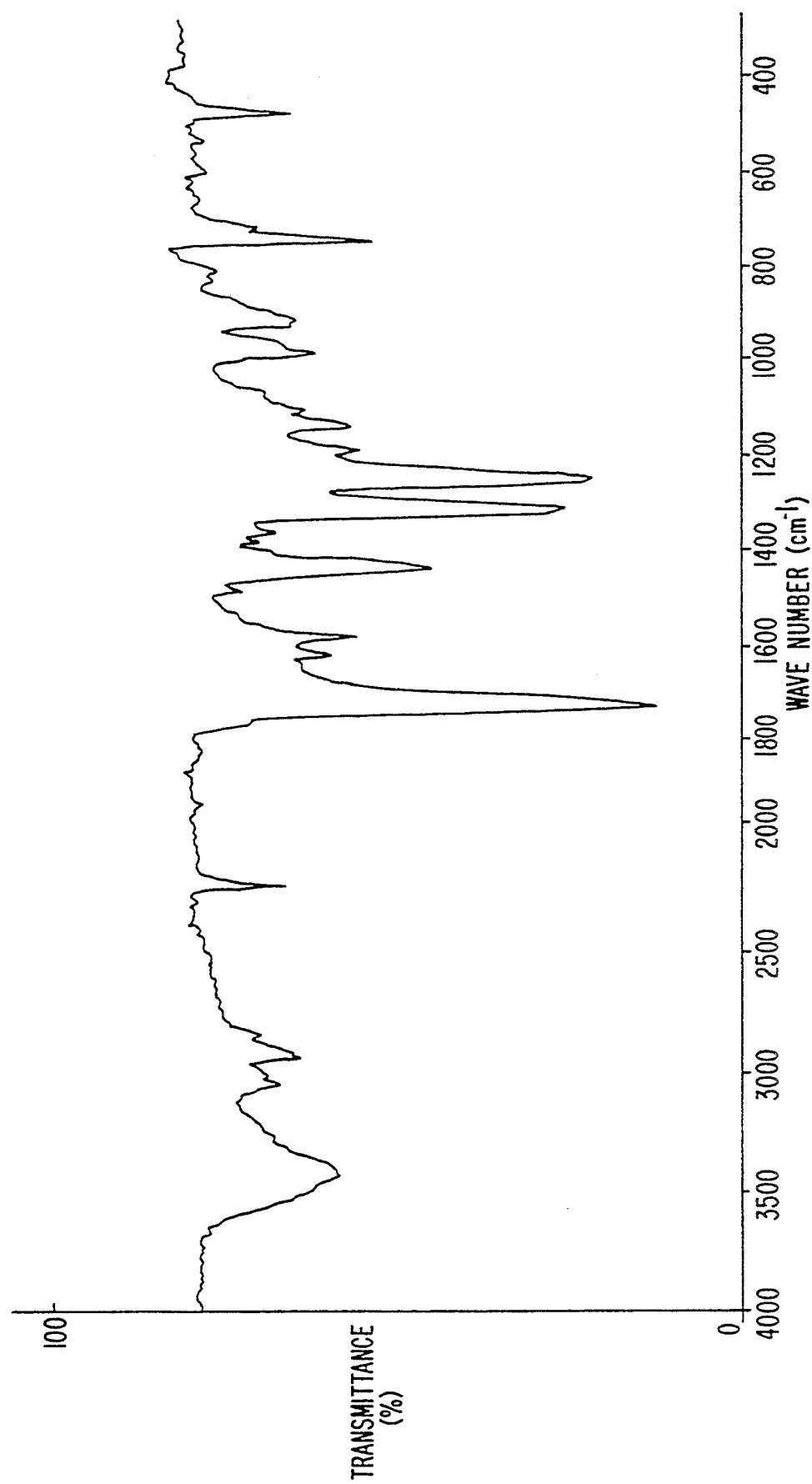

(4) IR spectrum (KBr) is shown in FIG. 43.

Example 1

[Synthesis of sodium zinc-naphthalocyaninetetracarboxylate (illustrative compound No. 126)]

Figure 44:
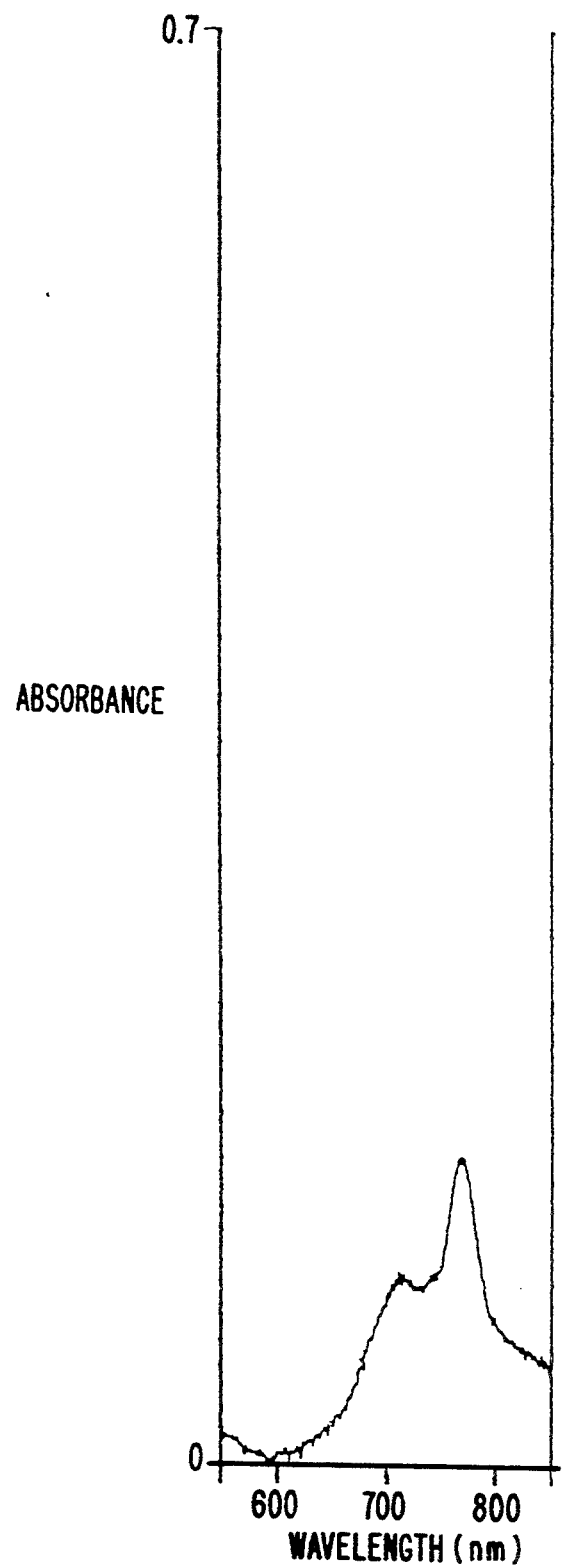
FIG. 44 shows an electronic spectrum (ethanol solution) of a compound of this invention.

After 100 mg ($8.10 \times 10^{-5}$ mol) of the compound obtained in Synthetic Example 19 was stirred in a mixture of 1.2 ml of a 1% aqueous NaOH solution and 1 ml of ethanol at 120° C. for 7 hours, the resulting mixture was concentrated under reduced pressure. The residue was transferred to a Soxhlet extractor and extracted with methanol. The methanol solution thus obtained was concentrated, followed by purification by reverse phase short-column chromatography (eluent: methanol), whereby 52 mg of sodium zinc-naphthalocyaninetetracarboxylate [illustrative compound No. 126] was obtained. Electronic spectrum of this compound is shown in FIG. 44.

Example 2

[Synthesis of sodium bis(triethylsiloxy)silicon-naphthalocyaninetetracarboxylate (illustrative comound No. 121)]

Figure 45:
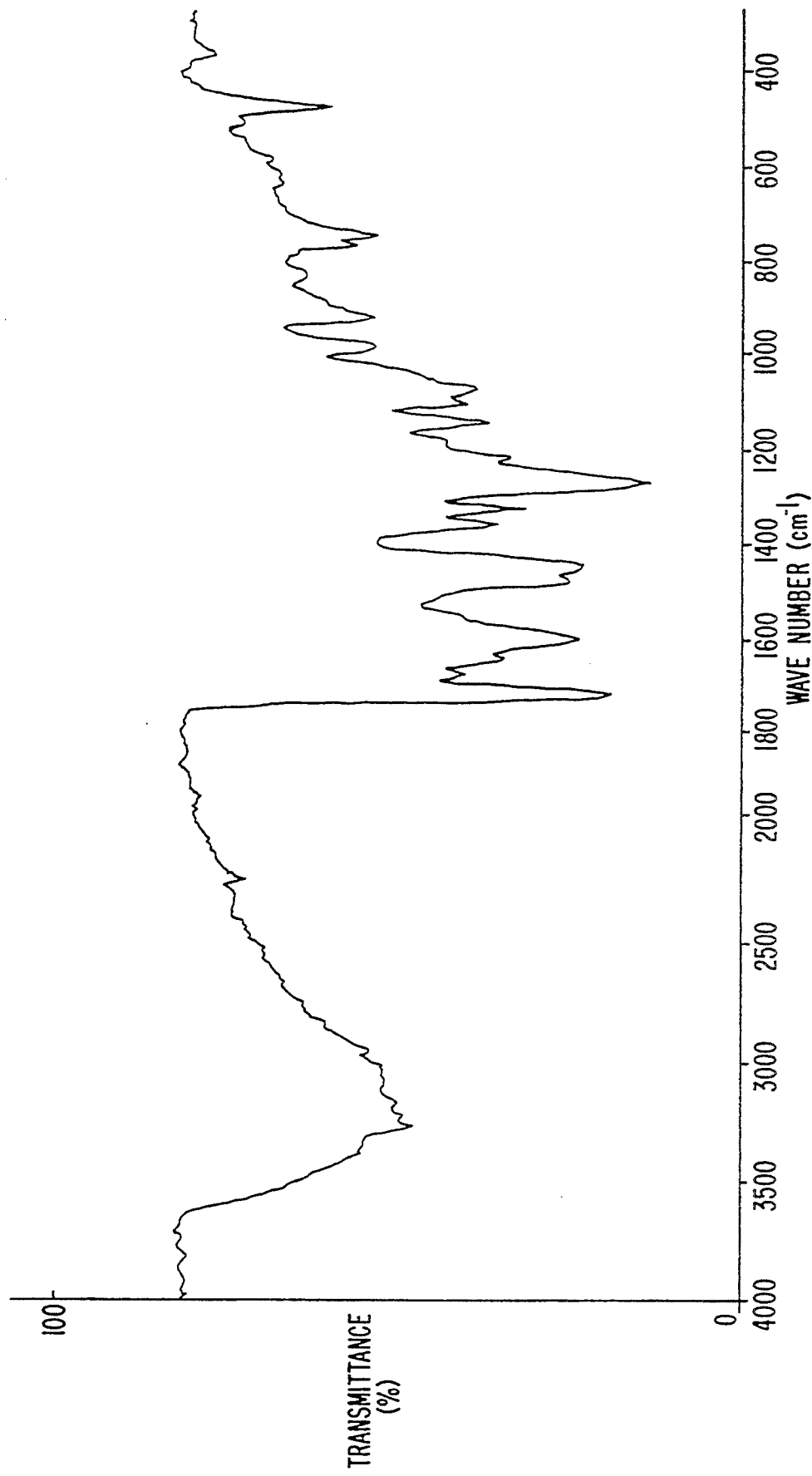

To a solution of sodium methoxide in methanol prepared by adding 0.1 g (4.35 mmols) of metallic sodium to 20 ml of absolute methanol was added 2 g (8.47 mmols) of 6-methoxycarbonyl-2,3-dicyanonaphthalene, and anhydrous ammonia gas was bubbled into the resulting mixture with sufficient mixing at room temperature for about 1 hour. The mixture was refluxed for about 3 hours, while bubbling therethrough anhydrous ammonia gas. After cooling, the yellow solid precipitated was filtered, and the solid was sufficiently washed with methanol and dried under reduced pressure to obtain 1.785 g (88%) of 6-carbamoyl-1,3-diiminobenz[f]isoindoline as a yellow solid. IR spectrum of this 6-carbamoyl-1,3-diiminobenz[f]isoindoline is shown in FIG. 45. The 6-carbamoyl-1,3-diiminobenz[f]isoindoline was used in the subsequent reaction without further purification.

Figure 46:
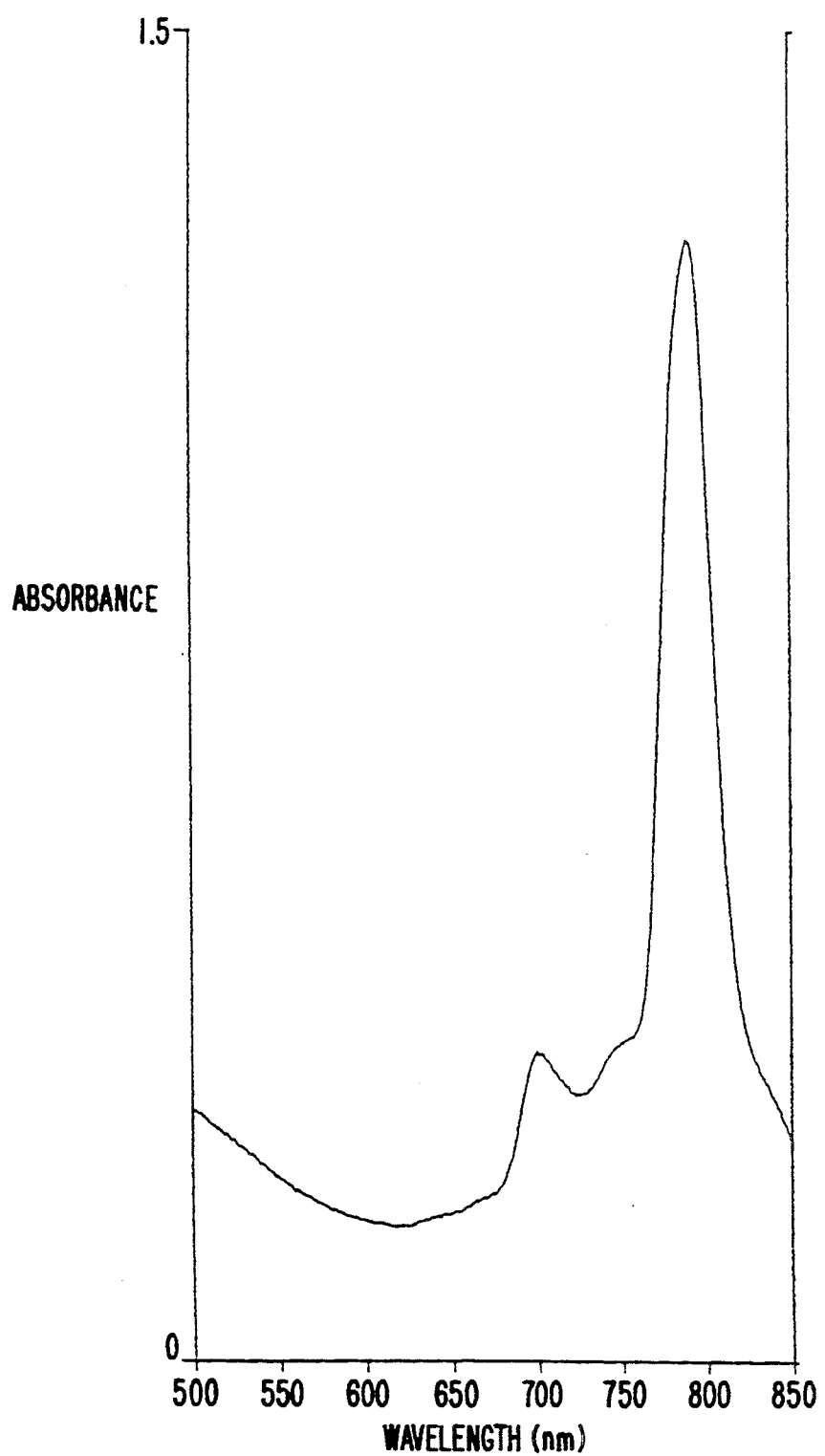
FIG. 46 shows an electronic spectrum (quinoline solution) of a compound of this invention.

To a suspension of 500 mg (2.10 mmols) of the 6-carbamoyl-1,3-diiminobenz[f]isoindoline in 10 ml of anhydrous quinoline was added 1.8 ml of silicon tetrachloride, and the resulting mixture was stirred at 220° C. for 3 hours. Then, an excess amount of the silicon tetrachloride was distilled off. After cooling, 40 ml of ethanol and 20 ml of aqueous ammonia were added to the residue, and the resulting mixture was refluxed for 5 hours. After cooling, a dark-green solid thus obtained was filtered and the residue was sufficiently washed with methanol and dried under reduced pressure to obtain 934 mg of a dark-green solid. The dark-green solid was considered to be containing dihydroxysilicon-tetracarbamoylnaphthalocyanine from the electronic spectrum shown in FIG. 46. The dihydroxysilicon-tetracarbamoylnaphthalocyanine was used in the subsequent reaction without further purification.

Figure 47:
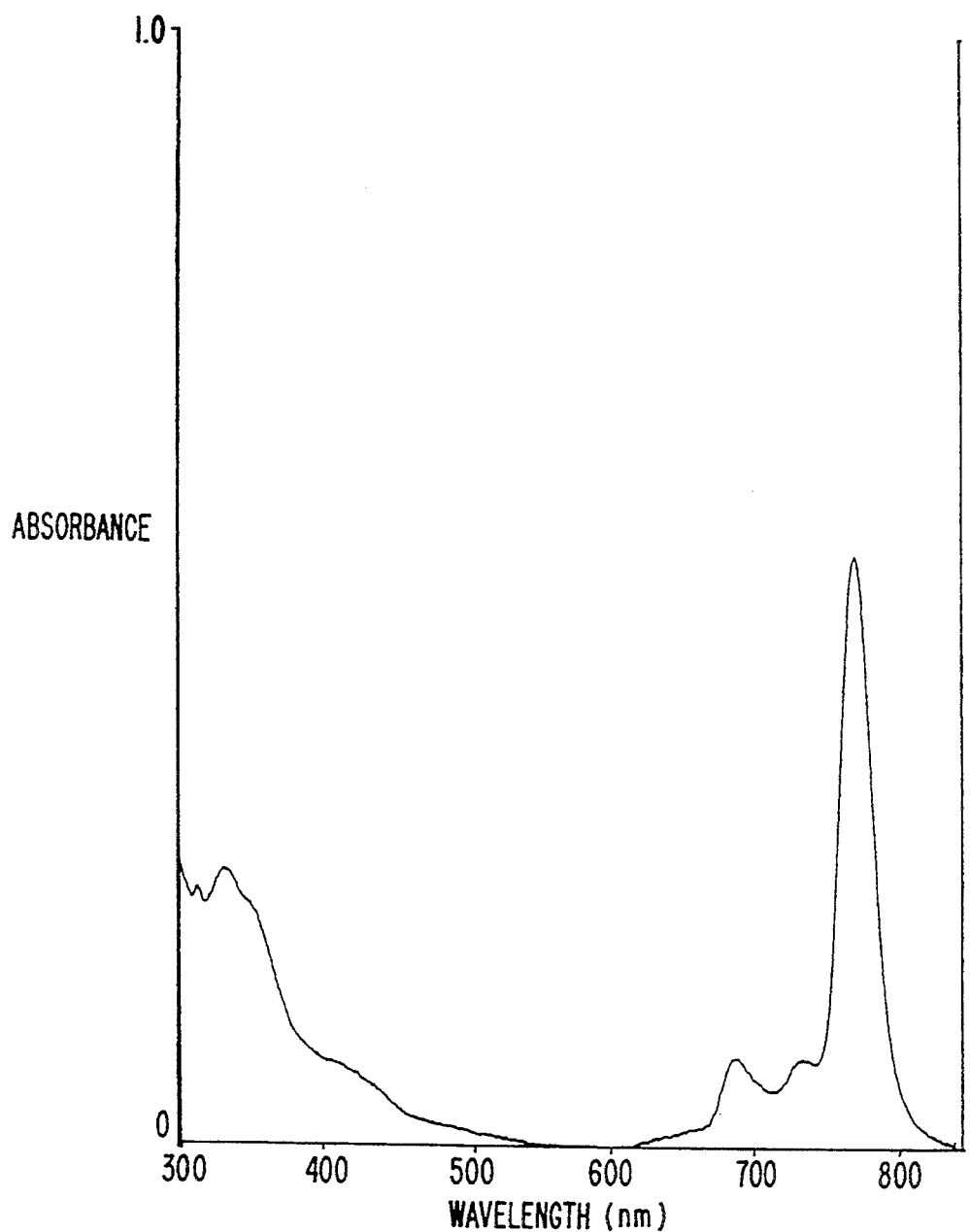

To a suspension of 600 mg ($6.34 \times 10^{-4}$ mol) of the dihydroxysilicon-tetracarbamoylnaphthalocyanine in 10 ml of quinoline was added 2 ml of triethylsilanol, and the resulting mixture was stirred at 200° C. for 3 hours. After completion of the reaction, quinoline was distilled off under reduced pressure. To the resulting residue were added 17 ml of a 1% aqueous NaOH solution and 24 ml of ethanol, and the resulting mixture was refluxed for 5 hours. The reaction mixture was filtered while hot and the filtrate was sufficiently washed with methanol and acetone. The mother liquor collected was concentrated and then subjected to reverse phase chromatography (eluent: methanol) to obtain 54 mg of the desired compound sodium bis(triethylsiloxy)silicon-naphthalocyaninetetracarboxylate [ilustrative compound No. 121] as a green solid. Electronic spectrum of this compound is shown in FIG. 47.

Example 3

[Synthesis of sodium bis(tributylsiloxy)silicon-tetraphenylthionaphthalocyaninesulfonate (illustrative compound No. 6)]

Figure 48:
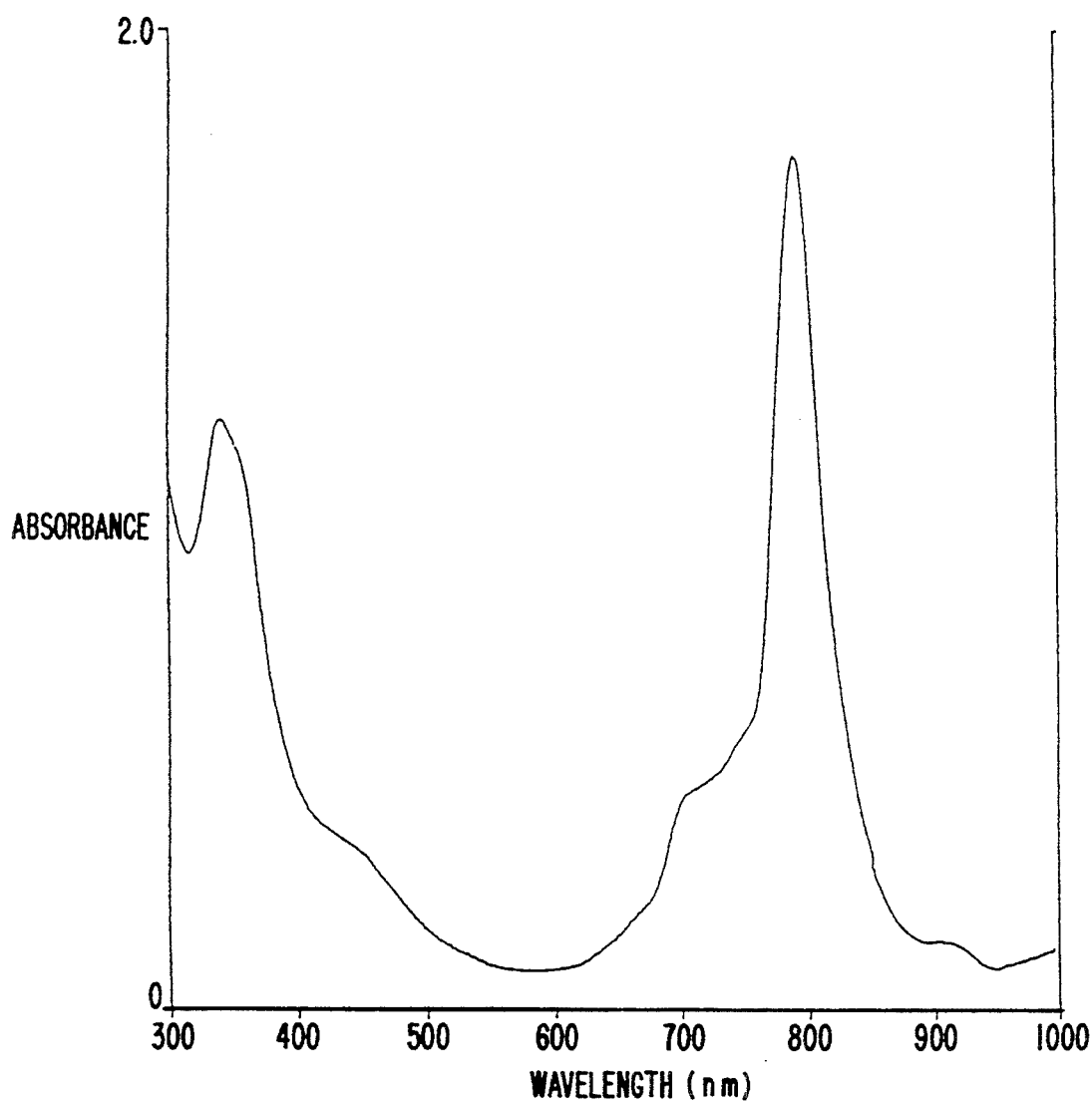

A solution of 100 mg ($6.23 \times 10^{-5}$ mol) of bis(tributylsiloxy)silicon-tetraphenylthionaphthalocyanine in 6 ml of chlorosulfonic acid was heated at 100° C. for 2 hours. After cooling, the reaction was quenched by adding about 25 g of ice with cooling on an ice bath. The reaction mixture was allowed to stand at room temperature for 4 hours, after which the solid precipitated was filtered. Only a material soluble in distilled water was extracted from the thus obtained dark-brown solid with distilled water. The brown acidic aqueous solutionn thus obtained was neutralized with a 20% aqueous NaOH solution and then concentrated under reduced pressure. The residue was transferred to a Soxhlet extractor and extracted with methanol for about 30 hours. The methanol solution thus obtained was concentrated followed by purification by reverse phase chromatography (eluent: methanol). The methanol solution obtained was concentrated, and aceton was added to precipitate dark-green crystals. The crystals were filtered and the residue was dried under reduced pressure to obtain 77 mg of sodium bis(tributylsiloxy)silicon-tetraphenylthionaphthalocyaninesulfonate [illustrative compound No. 6]. Electronic spectrum of this compound is shown in FIG. 48.

Example 4

[Synthesis of sodium bis(tributylsiloxy)silicon-tetraphenylthionaphthalocyanine octacarboxylate [illustrative compoud No. 1)]

Figure 49:
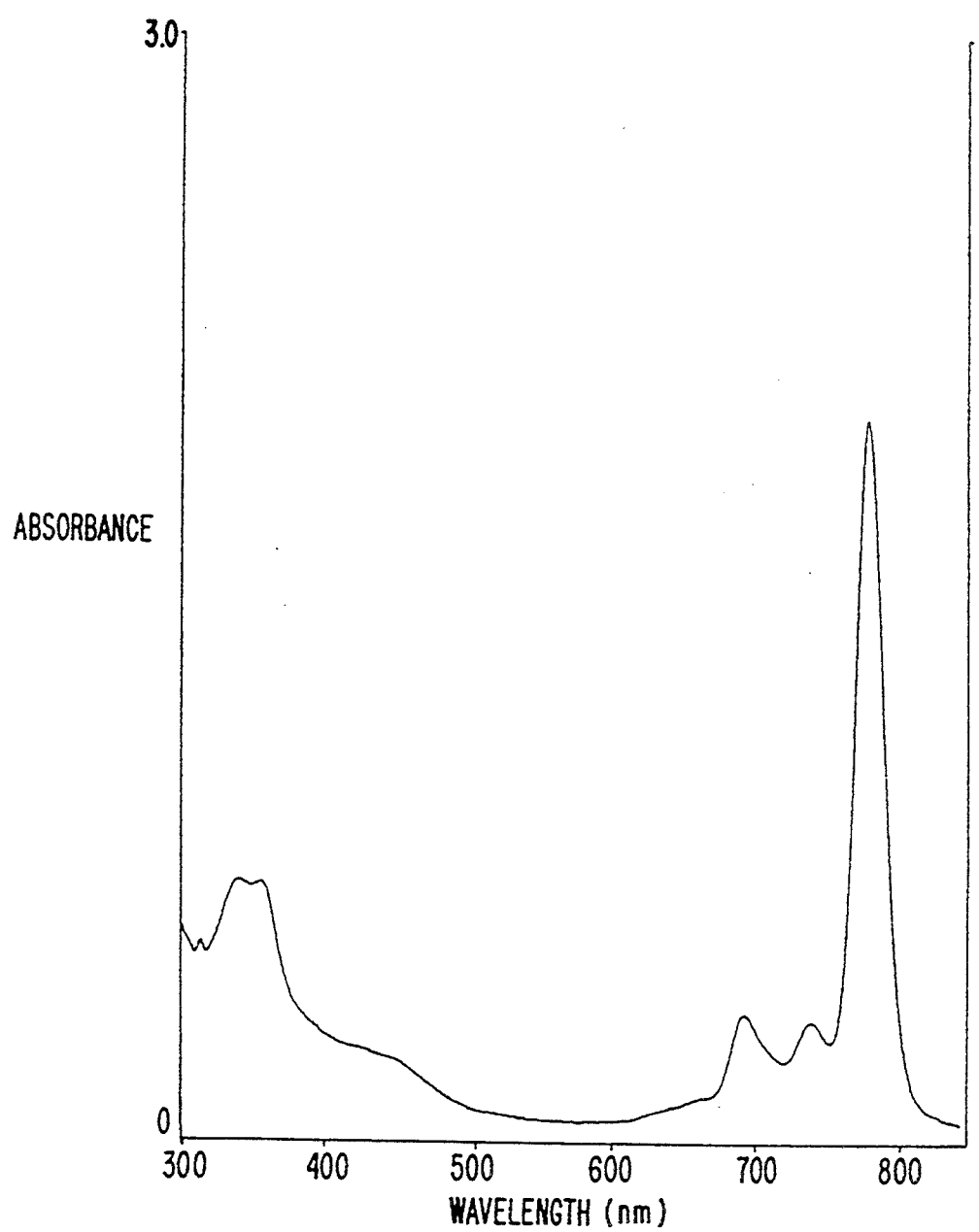

A suspension of 500 mg ($3.36 \times 10^{-4}$ mol) of bis(tributylsiloxy)silicon-tetrabromonaphthalocyanine and 418 mg ($1.45 \times 10^{-3}$ mol) of copper(I) 3,5-dimethoxycarbonylphenylthiolate in 8 ml of quinoline was stirred at 140° C. for 16 hours. After cooling, 40 ml of methanol/water (1/1) was added and the resulting mixture was allowed to stand overnight at room temperature. The solid precipitated was filtered and the residue was washed with methanol and dried under reduced pressure to obtain 798 mg of a green solid. Then, 100 mg of the green solid in a mixed solution of 10 ml of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 76 mg of sodium bis(tributylsiloxy)silicon-tetraphenylthionaphthalocyanineoctacarboxylate [illustrated compound No. 1] was obtained as dark-green crystals. Electronic spectrum of this compound is shown in FIG. 49.

Example 5

[Synthesis of sodium bis(tributylsiloxy)silicon-tetraphenylthioquinoxalocyanineoctacarboxylate (illustrative compound No. 41)]

Figure 50:
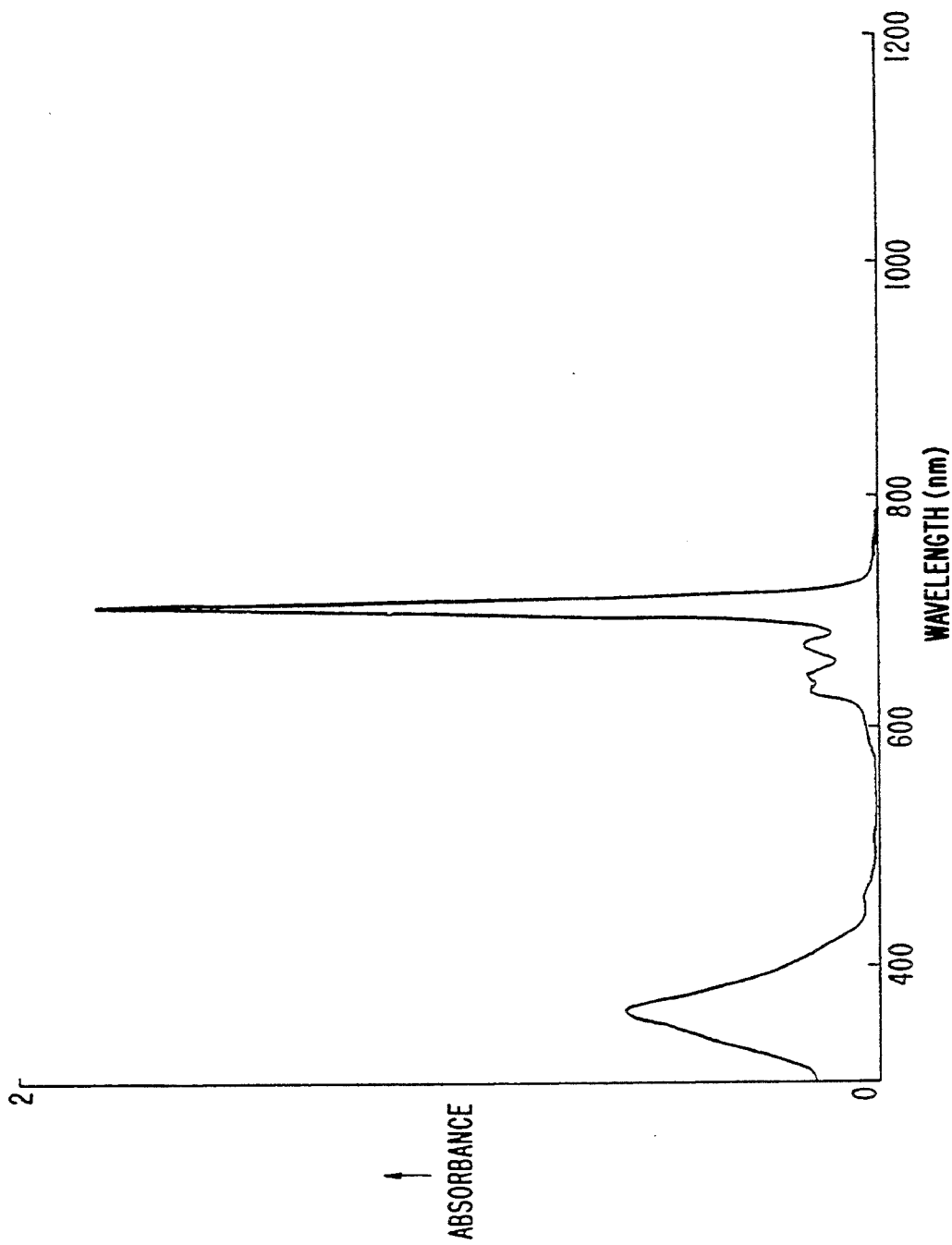

A suspension of 500 mg ($3.80 \times 10^{-4}$ mol) of bis(tributylsiloxy)silicon-tetrachloroquinoxalocyanine and 418 mg ($1.45 \times 10^{-3}$ mol) of copper(I) 3,5-dimethoxycarbonylphenylthiolate in 8 ml of quinoline was stirred at 200° C. for 10 hours. After cooling, 40 ml of methanol/water (1/1) was added and the resulting mixture was allowed to stand overnight at room temperature. The solid precipitated was filtered and the residue was washed with methanol and dried under reduced pressure to obtain 670 mg of a bluish-green solid. Then, 100 mg of the bluish-green solid in a mixed solution of 10 ml of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 51 mg of sodium bis(tributylsiloxy)silicon-tetraphenylthioquinoxalocyanineoctacarboxylate [illustrative compound No. 41] was obtained as dark-green crystals. Electronic spectrum of this compound is shown in FIG. 50.

Example 6

[Synthesis of sodium bis(tributylsiloxy)silicon-octaphenylthiophenanthracyaninehexadecacarboxylate [illustrative compound No. 62)]

A suspension of 500 mg ($2.50 \times 10^{-4}$ mol) of bis(tributylsiloxy)silicon-octabromophenanthracyanine and 418 mg ($1.45 \times 10^{-3}$ mol) of copper(I) 3,5-dimethoxycarbonylphenylthiolate in 8 ml of quinoline was stirred at 140° C. for 16 hours. After cooling, 40 ml of methanol/water (1/1) was added and the resulting mixture was allowed to stand overnight at room temperature. The solid precipitated was filtered and the residue was washed with methanol and dried under reduced pressure to obtain 798 mg of a green solid. Then, 100 mg of the green solid in a mixed solution of 10 ml of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 48 mg of sodium bis(tributylsiloxy)silicon-octaphenylthiophenanthracyaninehexadecacarboxylate [illustrative compound No. 62] was obtained as dark-green crystals.

Example 7

[Synthesis of sodium bis(tributylsiloxy)silicon-octaphenylthioanthracyaninehexadecacarboxylate illustrative compound No. 82)]

A suspension of 500 mg ($2.50 \times 10^{-4}$ mol) of bis(tributylsiloxy)silicon-octabromoanthracyanine and 418 mg ($1.45 \times 10^{-3}$ mol) of copper(I) 3,5-dimethoxycarbonylphenylthiolate in 8 ml of quinoline was stirred at 150° C. for 14 hours. After cooling, 40 ml of methanol/water (1/1) was added and the resulting mixture was allowed to stand overnight at room temperature. The solid precipitated was filtered and the residue was washed with emthanol and dried under reduced pressure to obtain 824 mg of a dark-brown solid. Then, 100 mg of the dark-brown solid in a mixed solution of 10 ml of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 53 mg of sodium bis(tributylsiloxy)silicon-octaphenylthioanthracyaninehexadecacarboxylate [illustrative compound No. 82] was obtained as dark-brown crystals.

Example 8

[Synthesis of sodium bis(tributylsiloxy)silicon-tetraphenylthio(1,2-naphthalocyanine)octacarboxylate (illustrative compound No. 101)]

A suspension of 500 mg ($3.36 \times 10^{-4}$ mol) of bis(tributylsiloxy)silicon-tetrabromo(1,2-naphthalocyanine) and 418 mg ($1.45 \times 10^{-3}$ mol) of copper (I) 3,5-dimethoxycarbonylphenylthiolate in 8 ml of quinoline was stirred at 140° C. for 20 hours. After cooling, 40 ml of methanol/water (1/1) was added and the resulting mixture was allowed to stand overnight at room temperature. The solid precipitated was filtered and the residue was washed with methanol and dried under reduced pressure to obtain 745 mg of a green solid. Then, 100 mg of the green solid in a mixed solution of 10 m of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 61 mg of sodium bis(tributylsiloxy)silicon-tetraphenylthio(1,2-naphthalocyanine)octacarboxylate [illustrative compound No. 101] was obtained as dark-green crystals.

Example 9

[Synthesis of sodium bis(tributylsiloxy)silicon-tetraphenylthioquinolocyanineoctacarboxylate (illustrative compound No. 21)]

Figure 51:
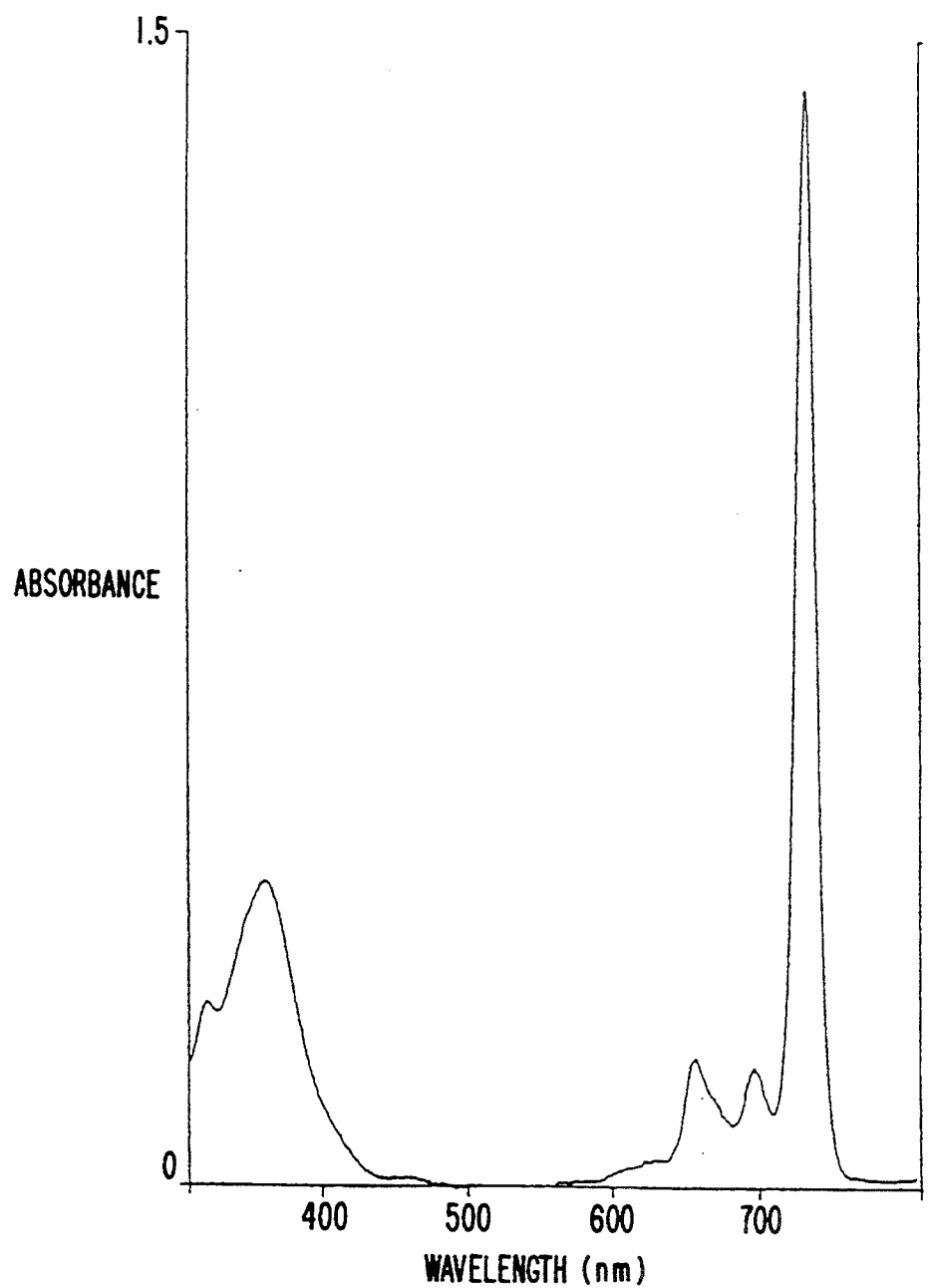

A suspension of 500 mg ($3.35 \times 10^{-4}$ mol) of bis(tributylsiloxy)silicon-tetrabromoquinolocyanine and 418 mg ($1.45 \times 10^{-3}$ mol) of copper(I) 3,5-dimethoxycarbonylphenylthiolate in 8 ml of quinoline was stirred at 140° C. for 18 hours. After cooling, 40 ml of methanol/water (1/1) was added and the resulting mixture was allowed to stand overnight at room temperature. The solid precipitated was filtered and the residue was washed with methanol and dried under reduced pressure to obtain 642 mg of a green solid. Then, 100 mg of the green solid in a mixed solution of 10 ml of a 2% aqueous NaOH solution and 10 ml of ethanol was stirred at 90° C. for 2 hours. After cooling, the resulting mixture was neutralized with concentrated hydrochloric acid and concentrated under reduced pressure. By separation and purification from the resulting residue by a reverse phase chromatography (eluent: methanol), 68 mg of sodium bis(tributylsiloxy)silicon-tetraphenylthioquinolocyanineoctacarboxylate [illustrative compound No. 21] was obtained as dark-green crystals. Electronic spectrum of this compound is shown in FIG. 51.

Example 10

[Synthesis of sodium bis(trihydroxyneopentoxy)silicon-tetraphenylthionaphthalocyanineoctacarboxylate (illustrative compound No. 11)]

Figure 52:
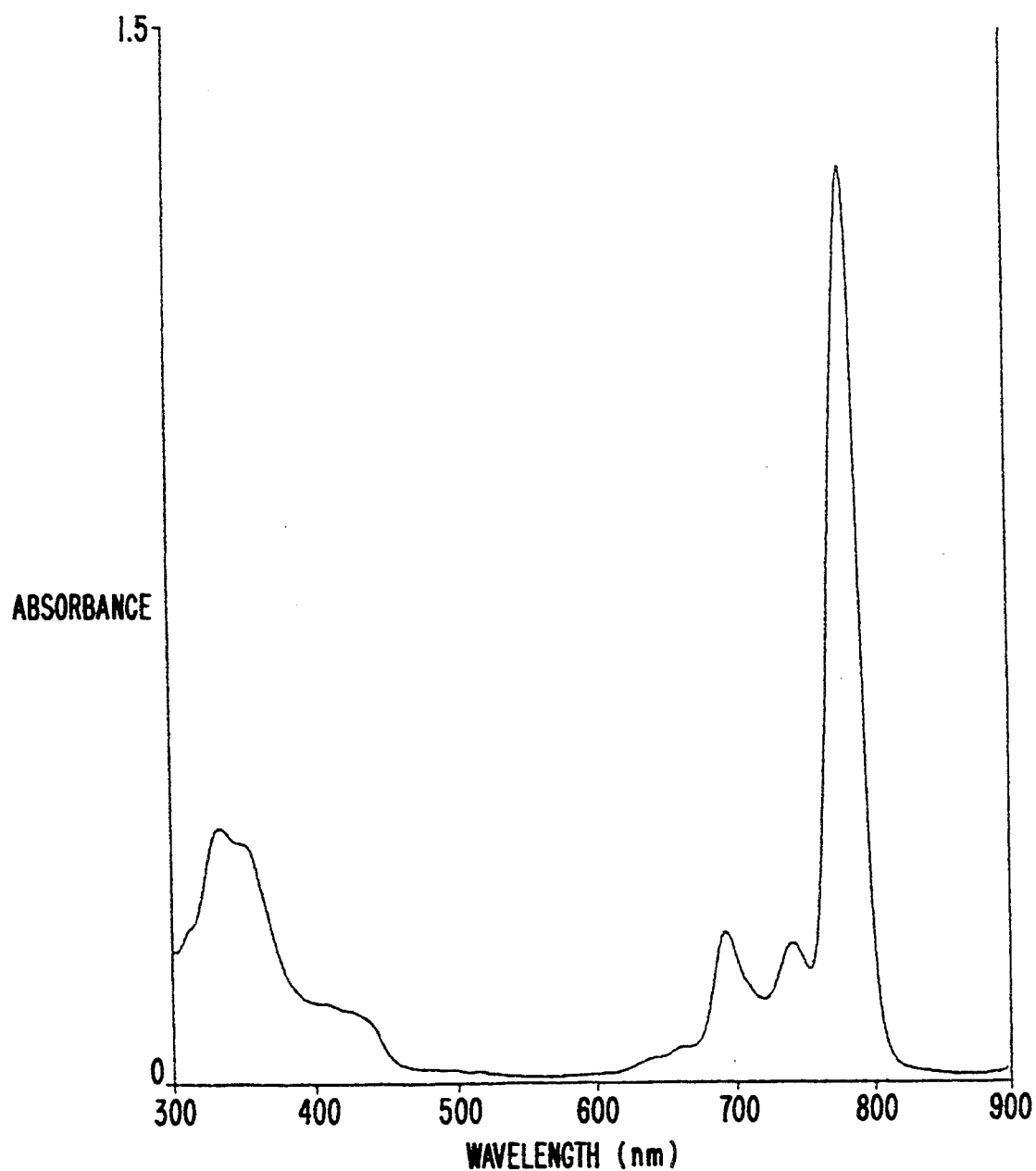

Octacarbamoylated dihydroxysilicon-tetraphenylthionaphthalocyanine was obtained by treating 2,3-dicyano-6-(3',5'-dimethoxycarbonylphenylthio)naphthalene as a starting material in the same manner as in Synthetic Examples 3, 4 and 5. Then, 50 mg ($3.22 \times 10^{-5}$ mol) of the compound obtained and 68 mg ($5 \times 10^{-4}$ mol) of pentaerythritol were stirred in 5 ml of quinoline at 200° C. for 4 hours. After completion of the reaction, the reaction mixture was concentrated under reduced pressure and 5 ml of ethanol and a 2% aqueous NaOH solution were added, followed by stirring at 90° C. for 3 hours. After cooling, the resulting mixture was neutralized with concentrated hydrochloric acid and concentrated under reduced pressure. By separation and purification from the resulting residue by a reverse phase chromatography (eluent: methanol), 18 mg of sodium bis(trihydroxyneopentoxy)silicon-tetraphenylthionaphthalocyanineoctacarboxylate [illustrative compound No. 11] was obtained as dark-green crystals. Electronic spectrum of this compound is shown in FIG. 52.

Example 11

[Synthesis of sodium bis(tripropylsiloxy)silicon-tetraethylthionaphthalocyaninetetracarboxylate (illustrative comound No. 16)]

Figure 53:
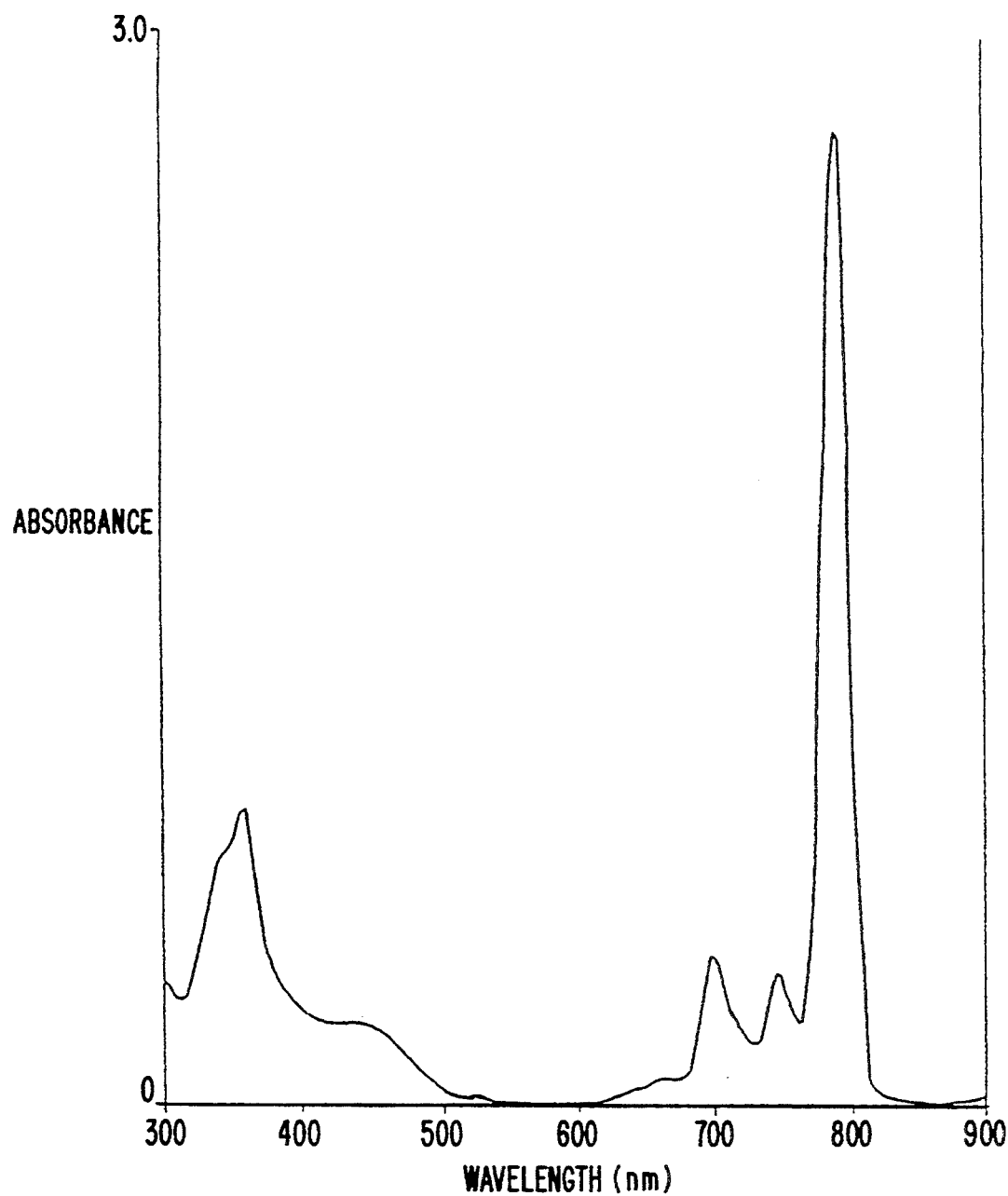

To a mixture of 5 ml of ethanol and 5 ml of a 2% aqueous NaOH solution was added 20 mg of the bis(tripropylsiloxy)silicon-tetrakis[2-(2',2',4',4'-tetramethylpentyloxycarbonyl)ethylthio]naphthalocyanine obtained in Synthetic Example 12, and stirred at 90° C. for 3 hours. After cooling, the resulting mixture was neutralized with concentrated hydrochloric acid and concentrated under reduced pressure. By separation and purification from the resulting residue by a reverse phase chromatography (eluent: methanol), 9 mg of sodium bis(tripropylsiloxy)silicon-tetraethylthionaphthalocyaninetetracarboxylate [illustrative compound No. 16 was obtained as dark-green crystals. Electronic spectrum of this compound is shown in FIG. 53.

Text Example 1

[Measurement of fluorescence quantum yield]

For the tetraazaporphins obtained in Examples 1 to 11 and tetraaxzaporphins of this invention obtained in the same manner as in Examples 1 to 11, fluorescence quantum yield was measured according to the method for measuring relative quantum yield described in a reference [J. Photochem. Photobiol, A. Chemistry, vol. 45, p. 117–121 (1988)] using 1,1',3,3,3',3'-hexamethylindotricarbocyanine perchlorate or oxazine-720 as a standard substance in the near infrared region. The results obtained are shown in Tables 10 to 12. As is clear from Tables 10 to 12, all of the fluorochromes for labeling of this invention show a sufficient fluorescence quantum yield.

TABLE 10

| Illustrative compound No. | Solvent | Excitation wavelength (nm) | Fluorescence quantum yield |
|---|---|---|---|
| 1 | Methanol | 700 | 0.33 |
| 6 | " | " | 0.30 |
| 8 | " | " | 0.31 |
| 9 | " | " | 0.33 |
| 11 | " | " | 0.34 |
| 12 | " | " | 0.36 |
| 16 | " | " | 0.32 |
| 21 | " | 650 | 0.52 |
| 29 | " | " | 0.56 |
| 30 | " | " | 0.55 |
| 31 | " | " | 0.55 |
| 32 | " | " | 0.53 |
| 41 | " | " | 0.56 |
| 48 | " | " | 0.54 |
| 49 | " | " | 0.53 |
| 51 | " | " | 0.56 |
| 52 | " | " | 0.54 |
| 62 | " | " | 0.37 |
| 65 | " | " | 0.35 |
| 68 | " | " | 0.40 |

TABLE 11

| Illustrative compound No. | Solvent | Excitation wavelength (nm) | Fluorescence quantum yield |
|---|---|---|---|
| 69 | Methanol | 650 | 0.38 |
| 71 | " | " | 0.35 |
| 72 | " | " | 0.37 |
| 77 | " | " | 0.40 |
| 82 | " | 780 | 0.32 |
| 86 | " | " | 0.30 |
| 89 | " | " | 0.29 |
| 91 | " | " | 0.30 |
| 92 | " | " | 0.32 |
| 97 | " | " | 0.41 |
| 101 | " | 610 | 0.35 |
| 105 | " | " | 0.34 |
| 108 | " | " | 0.34 |
| 109 | " | " | 0.36 |
| 111 | " | " | 0.35 |
| 112 | " | " | 0.36 |
| 117 | " | " | 0.45 |
| 121 | " | 700 | 0.18 |
| 126 | Ethanol | " | 0.10 |
| 131 | Methanol | 650 | 0.16 |

TABLE 12

| Illustrative compound No. | Solvent | Excitation wavelength (nm) | Fluorescence quantum yield |
|---|---|---|---|
| 136 | Methanol | 650 | 0.17 |
| 141 | " | " | 0.15 |
| 146 | " | " | 0.11 |
| 150 | " | " | 0.17 |

TABLE 12-continued

| Illustrative compound No. | Solvent | Excitation wavelength (nm) | Fluorescence quantum yield |
|---|---|---|---|
| 151 | " | " | 0.18 |
| 156 | " | " | 0.14 |
| 158 | " | " | 0.19 |
| 161 | " | 780 | 0.17 |
| 167 | " | " | 0.11 |
| 172 | " | 610 | 0.17 |
| 178 | " | " | 0.15 |
| 180 | " | " | 0.19 |

Example 12

Figure 54:
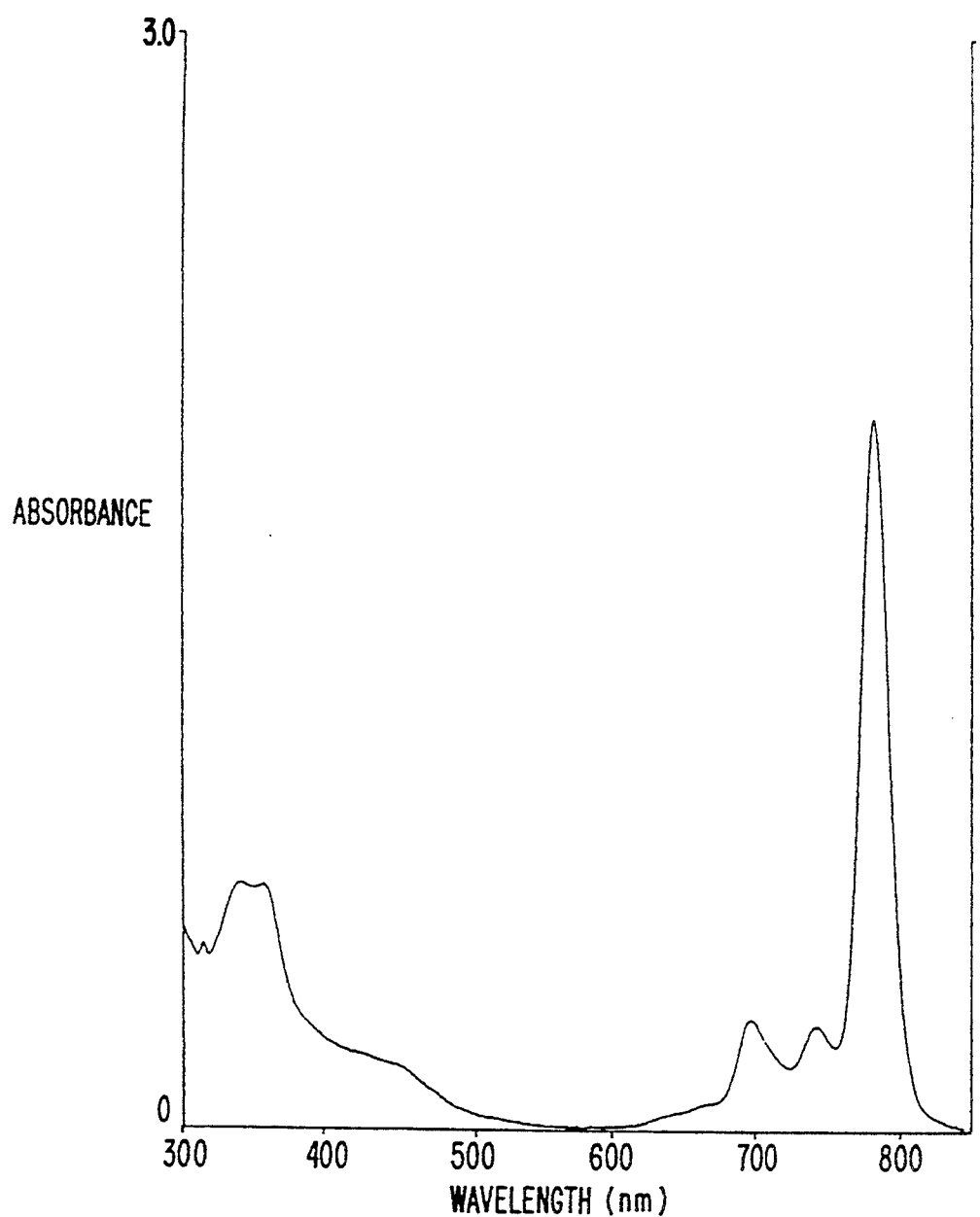

A solution of 10 mg ($4.69 \times 10^{-6}$ mol) of sodium bis(tributylsiloxy)silicon-tetraphenylthionaphthalocyanineoctacarboxylate [illustrative compound No. 1] in 10 ml of methanol was acidified with dilute hydrochloric acid and quickly concentrated to dryness under reduced pressure. Only a material soluble in anhydrous DMF was extracted from the resulting residue with 30 ml of anhydrous DMF, and 0.1 mg ($8.14 \times 10^{-7}$ mol) of N,N-dimethylaminopyridine and 0.35 mg ($4.60 \times 10^{-8}$ mol) of 1,3-propanediol were added to the extract solution, followed by adding thereto 1 mg ($4.85 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure. Separation and purification from the resulting residue by reverse phase chromatography gave 5 mg of bis(tributylsiloxy)silicon-tetraphenylthionaphthalocyanineoctacarboxylic acid monohydroxypropyl ester heptasodium salt. Electronic spectrum of this compound is shown in FIG. 54.

Example 13

Figure 55:
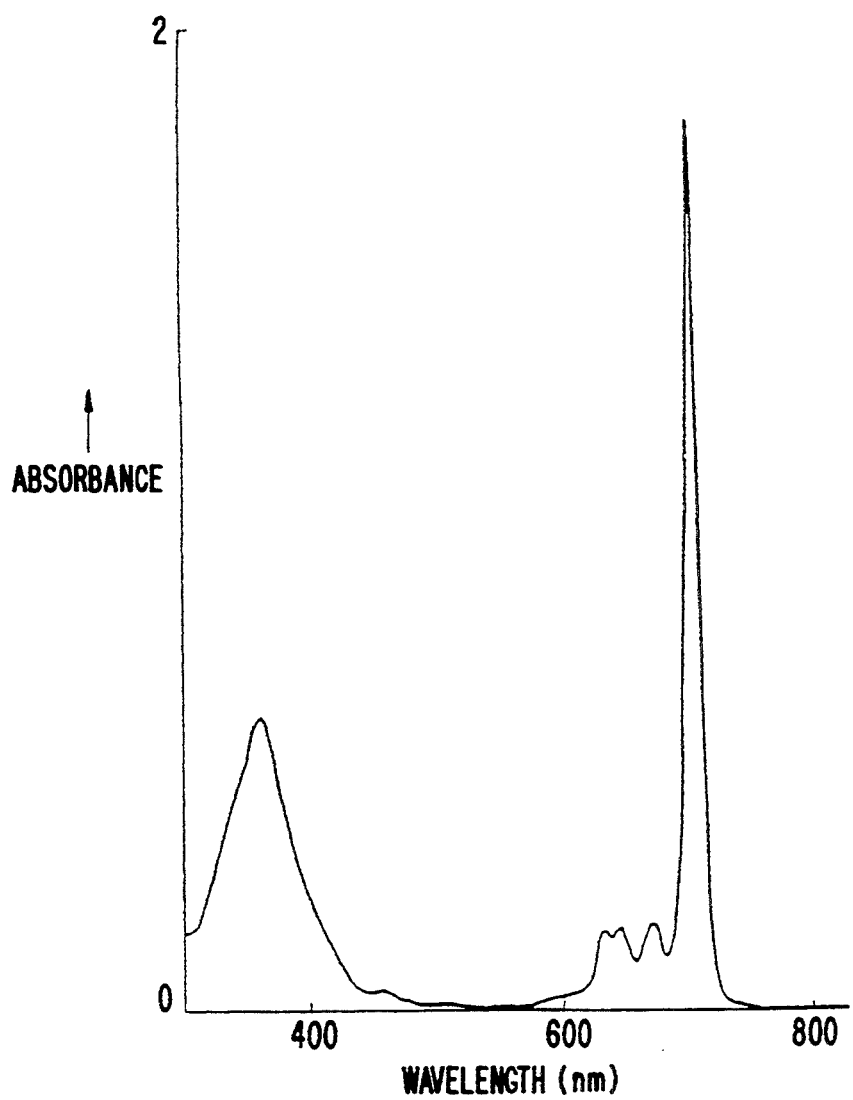

A solution of 10 mg ($4.67 \times 10^{-6}$ mol) of sodium bis(tributylsiloxy)silicon-tetraphenylthioquinoxalocyanineoctacarboxylate [illustrative compound No. 41] in 10 ml of methanol was acidified with dilute hydrochloric acid and quickly concentrated to dryness under reduced pressure. Only a material soluble in anhydrous DMF was extracted from the resulting residue with 30 ml of anhydrous DMF, and 0.1 mg ($8.14 \times 10^{-7}$ mol) of N,N-dimethylaminopyridine and 0.35 mg ($4.60 \times 10^{-6}$ mol) of 1,3-propanediol were added to the extract solution, followed by adding thereto 1 mg ($4.85 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure. Separation and purification from the resulting residue by a reverse phase chromatography gave 4 mg of bis(tributylsiloxy)silicon-tetraphenylthioquinoxalocyanineoctacarboxylic acid monohydroxypropyl ester heptasodium salt. Electronic spectrum of this compound is shown in FIG. 55.

Example 14

A solution of 10 mg ($3.04 \times 210^{-6}$ mol) of sodium bis(tributylsiloxy)silicon-octaphenylthiophenanthracyaninehexadecacarboxylate [illustrative compound No. 62] in 10 ml of methanol was acidified with dilute hydrochloric acid and quickly concentrated to dryness under reduced pressure. Only a material soluble in anhydrous DMF was extracted from the resulting residue with 20 ml of anhydrous DMF, and 0.1 mg ($8.14 \times 10^{-7}$ mol) of N,N-dimethylaminopyridine and 0.22 mg ($2.89 \times 10^{-6}$ mol) of 1,3-propanediol were added to the extract solution, followed by adding thereto 0.64 mg ($3.10 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure. Separation and purification from the resulting residue by a reverse phase chromatography gave 5 mg of bis(tributylsiloxy)-silicon-octaphenylthiophenanthracyaninehexadecacarboxylic acid monohydroxypropyl ester pentadecasodium salt.

Example 15

A solution of 10 mg ($3.04 \times 10^{-6}$ mol) of sodium bis(tributylsiloxy)silicon-octaphenylthioanthracyaninehexadecacarboxylate [illustrative compound No. 82] in 10 ml of methanol was acidified with dilute hydrochloric acid and quickly concentrated to dryness under reduced pressure. Only a material soluble in anhydrous DMF was extracted from the resulting residue with 20 ml of anhydrous DMF, and 0.1 mg ($8.14 \times 10^{-7}$ mol) of N,N-dimethylaminopyridine and 0.22 mg ($2.89 \times 10^{-6}$ mol) of 1,3-propanediol were added to the extract solution, followed by adding thereto 0.64 mg ($3.10 \times 10^{-6}$ mol) of 1,3-dicyclohexylcarbodiimide (DCC) with sufficient stirring. The stirring was continued at room temperature for 4 hours. To the reaction mixture was added 1 ml of 0.2M $Na_2CO_3$ buffer (pH 9.3), after which the resulting mixture was concentrated under reduced pressure. Separation and purification from the resulting residue by a reverse phase chromatography gave 4 mg of bis(tributylsiloxy)-silicon-octaphenylthioanthracyaninehexadecacarboxylic acid monohydroxypropyl ester pentadecasodium salt.

Example 16

A solution of 10 mg ($4.69 \times 10^{-6}$ mol) of sodium bis(tributylsiloxy)silicon-octaphenylthio(1,2-naphthalocyanine)octacarboxylate [illustrative compound No. 101] in 10 ml of methanol was acidified with dilute hydrochloric acid and quickly concentrated to dryness under reduced pressure. Only a material soluble in anhydrous DMF was extracted from the resulting residue with 30 ml of anhydrous DMF, and 0.1 mg ($8.14 \times 10^{-7}$ mol) of N,N-dimethylaminopyridine and 0.35 mg ($4.60 \times 10^{-6}$ mol) of 1,3-propanediol were added to the extract solution, followed by adding thereto 1 mg ($4.85 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure. Separation and purification from the resulting residue by a reverse phase chromatography gave 5 mg of bis(tributylsiloxy)silicontetraphenylthio(1,2-naphthalocyanine)octacarboxylic acid monohydroxypropyl ester heptasodium salt.

Example 17

A solution of 10 mg ($4.68 \times 10^{-6}$ mol) of sodium bis(tributylsiloxy)silicon-tetraphenylthioquinolocyanineoctacarboxylate [illustrative compound No. 21] in 10 ml of methanol was acidified with dilute hydrochloric acid and quickly concentrated to dryness under reduced pressure. Only a material soluble in anhydrous DMF was extracted from the resulting residue with 30 ml of anhydrous DMF, and 0.1 mg ($8.14 \times 10^{-7}$ mol) of N,N-dimethylaminopyridine and 0.35 mg ($4.60 \times 10^{-6}$ mol) of 1,3-propanediol were added to the extract solution, followed by adding thereto 1 mg ($4.85 \times 10^{-6}$ mol) of 1,3-dicyclohexylcarbodiimide (DCC) with sufficient stirring. The stirring was continued at room temperature for 5 hours. To the reaction mixture was added 1 ml of 0.2M $Na_2CO_3$ buffer (pH 9.3), after which the resulting mixture was concentrated under reduced pressure to obtain 4 mg of bis(-tributylsiloxy)silicon-tetraphenylthioquinolocyanineoctacarboxylic acid monohydroxypropyl ester heptasodium salt. Electronic spectrum of this compound is shown in FIG. 56.

Example 18

[Synthesis of a phosphorylated oligonucleotide primer]

A primer (5'-GTTTCCCAGTCACGAC-3') was synthesized by means of an automatic DNA synthesizer using the solid phase CED-phosphoramide method. The primer synthesized was phosphorylated by incubating the same in 100 μl of a reaction solution containing 50 mM Tris-hydrochloric acid (pH 7.6), 10 mM magnesium chloride, 10 mM dithiothreitol, 3 mM ATP and $T_4$-nucleotide kinase, at 37° C. for 1 hour. The primer phosphorylated was separated by a high pressure liquid chromatography (HPLC) using a column for gel filtration. A fraction corresponding to a peak due to the primer phosphorylated was collected, and the solvent was removed by freeze-drying.

Example 19

To 100 μl of a 0.05 mM solution of the bis(tributylsiloxy)silicon-tetraphenylthionaphthalocyanineoctacarboxylic acid monohydroxypropyl ester heptasodium salt synthesized in Example 12 in DMF were added 100 μl of a 0.05 mM solution of the phosphorylated oligonucleotide primer obtained in Example 18 in DMF, and then 100 μl of a 0.05 mM solution of DCC in DMF. The resulting mixture was stirred overnight at room temperature. To the reaction mixture was added 100 μl of 0.2M $Na_2CO_3$ buffer (pH 9.3), after which the resulting mixture was concentrated under reduced pressure. By separation from the resulting residue by HPLC, the oligonucleotide primer labeled with illustrative compound No. 1 was obtained.

Example 20

The oligonucleotide primer labeled with illustrative compound No. 41 was obtained by treating 100 μl of a 0.05 mM solution of the bis(tributylsiloxy)silicon-tetraphenylthioquinoxalocyanineoctacarboxylic acid monohydroxypropyl ester heptasodium salt synthesized in Example 13 in DMF, in the same manner as in Example 19.

Example 21

The oligonucleotide primer labeled with illustrative compound No. 62 was obtained by treating 100 μl of a 0.05 mM solution of the bis(tributylsiloxy)silicon-octaphenylthiophenanthracyaninehexadecacarboxylic acid monohydroxypropyl ester pentadecasodium salt synthesized in Example 14 in DMF, in the same manner as in Example 19.

Example 22

The oligonucleotide primer labeled with illustrative compound No. 82 was obtained by treating 100 μl of a 0.05 mM solution of the bis(tributylsiloxy)silicon-octaphenylthioanthracyaninehexadecacarboxylic acid monohydroxypropyl ester pentadecasodium salt synthesized in Example 15 in DMF, in the same manner as in Example 19.

Example 23

The oligonucleotide primer labeled with illustrative compound No. 101 was obtained by treating 100 μl of a 0.05 mM solution of the bis(tributylsiloxy)silicon-tetraphenylthio(1,2-naphthalocyanine)octacarboxylic acid monohydroxypropyl ester heptasodium salt synthesized in Example 16 in DMF, in the same manner as in Example 19.

Example 24

The oligonucleotide primer labeled with illustrative compound No. 21 was obtained by treating 100 μl of a 0.05 mM solution of the bis(tributylsiloxy)silicon-tetraphenylthioquinolocyanineoctacarboxylic acid monohydroxypropyl ester heptasodium salt synthesized in Example 17 in DMF, in the same manner as in Example 19.

Example 25

The oligonucleotide primer which has been labeled with illustrative compound No. 11 was obtained by treating 100 μl of a 0.05 mM solution of the illustrative compound No. 11 synthesized in Example 10 in DMF, in the same manner as in Example 19.

Example 26

[Analysis of the base sequence of DNA]

A DNA having a known base sequence was used as a sample. Sanger reaction was carried out for the 4 kinds of bases using each of the labeled primers synthesized in Examples 19 to 25 or primers having a tetraazaporphin attached thereto through a linker synthesized in the same manner as in Examples 19 to 25. The DNA fragments thus obtained were separated by electrophoresis in different lanes for the 4 reaction systems, respectively, and analyzed by means of a DNA sequencer equipped with a semiconductor laser. The results obtained are summarized in Table 13. The reaction systems contained a nonionic surfactant as an addition if necessary.

TABLE 13

| Tetraazaporphin-labeled primer (illustrative compound No.) | Nonionic surfactant | Output wavelength of semiconductor laser (nm) | Number of bases of DNA | Precision |
| --- | --- | --- | --- | --- |
| 1 | Triton X-100 | 770 | 350 | 99.7% |
| 41 | " | 670 | 320 | 99.4% |
| 62 | " | " | 290 | 99.7% |

TABLE 13-continued

| Tetraazaporphin-labeled primer (illustrative compound No.) | Nonionic surfactant | Output wavelength of semiconductor laser (nm) | Number of bases of DNA | Precision |
|---|---|---|---|---|
| 82 | Tween 20 | 830 | 340 | 99.7% |
| " | " | 780 | " | 100% |
| 101 | Triton X-100 | 670 | 300 | 100% |
| 21 | " | 680 | 350 | 99.7% |
| 11 | — | 770 | 330 | 99.7% |
| 13 | Triton X-100 | 780 | 340 | 99.4% |
| 4 | " | " | 380 | 99.7% |
| 53 | " | 670 | 280 | 100% |
| 44 | " | " | 320 | 100% |
| 151 | " | " | " | 98.8% |
| 156 | " | " | 350 | 99.1% |
| 157 | " | " | 300 | 99.1% |
| 154 | " | " | 320 | 98.8% |
| 172 | " | " | 370 | 98.5% |
| 176 | " | " | 310 | 98.8% |
| 178 | " | " | 330 | 98.8% |
| 174 | " | " | 300 | 98.8% |
| 126 | " | 780 | 300 | 98.5% |

Example 27

[Synthesis of tetrazaporphin-labeled primers (illustrative compound-ACACAACTGTGTTCACTAGC)]

Various labeled primers having a 5'-end labeled with a tetraazaporphin (illustrative compound No.-ACACAACTGTGTTCACTAGC) were synthesized in the same manner as in Example 18 and Example 19.

[Detection of β-globin gene in human DNA]

Human β-globin gene was detected by a gene detection method using the PCR (Polymorase Chain Reaction) method.

Sample 1

Twenty cycles of gene amplification was carried out (the total volume of solution: 100 μl) according to the protocol of Perkin-Elmer-Cetus Corporation by using human placental DNA (1 μg), each of the labeled primers, i.e., illustrative compound No.-ACACAACTGTGTTCACTAGC, synthesized in the manner described above (300 ng), HO-CAACTT-CATCCACGTTCACC (300 ng), a nonionic surfactant, and TaqDNA polymerase (Perkin-Elmer-Cetus Corporation).

Sample 2

Human placental DNA (1 μg), the same illustrative compound No.-ACACAACTGTGTTCACTAGC as in sample 1 (300 ng), HO-CAACTTCATCCACGTT-CACC (300 ng) and a nonionic surfactant were added to a reaction solution containing no TaqDNA polymerase which had been prepared according to the protocol of Perkin-Elmer-Cetus Corporation (the total volume of the solution: 100 μl).

To each of the samples (50 μl) was added 450 μl of buffer solution A (containing a nonionic surfactant, 50 mM NaCl, 10 mM Tris-HCl and 0.1 mM EDTA, pH 8.0), and the resulting mixture was added to octadecylsilane resin (Micro Bonda Pack C-18, Waters Co.) previously washed with buffer solution A. The octadecylsilane resin used was in the form of a layer formed by layering a suspension of the resin in ethanol over siliconized glass wool packed into the end of a pipet chip (for 1 ml).

After washing with buffer solution A (500 μl) and buffer solution A containing 5% ethanol (500 μl), elution was carried out using buffer solution A containing 10% ethanol (500 μl). The pH of the eluate was adjusted to about 8, and fluorescence intensity was measured by means of a photodiode array by using a semiconductor laser as an exciting light source. Consequently, the relative intensities shown in Tables 14 to 16 were attained.

Unreacted illustrative compound-No. ACACAACTGTGTTCACTAGC was usually not eluted at all with buffer solution A containing 10% ethanol, and was eluted only with buffer solution A containing 15% ethanol.

From these results, it was found that β-globin gene in human DNA can be detected using an oligodeoxynucleotide labeled with the tetraazaporphin of this invention at the 5'-end.

TABLE 14

| Illustrative compound No. | Nonionic surfactant | Output wavelength of semiconductor laser (nm) | Relative intensity | |
|---|---|---|---|---|
| | | | Sample 1 | Sample 2 |
| 1 | Triton X-100 | 770 | 2 | 167 |
| 2 | " | " | 5 | 152 |
| 5 | " | " | 8 | 133 |
| 7 | Tween 20 | " | 7 | 146 |
| 9 | " | " | 4 | 129 |
| 10 | Triton X-100 | " | 2 | 144 |
| 11 | " | " | 6 | 135 |
| 12 | — | " | 8 | 141 |
| 14 | — | " | 7 | 176 |
| 21 | Triton X-100 | 680 | 6 | 134 |
| 28 | " | " | 5 | 157 |
| 29 | " | " | 9 | 138 |
| 31 | " | " | 4 | 146 |
| 32 | " | " | 7 | 147 |
| 34 | — | " | 5 | 129 |
| 41 | Tween 20 | 670 | 6 | 135 |
| 42 | " | " | 3 | 142 |
| 48 | Triton X-100 | " | 4 | 166 |
| 49 | — | " | 6 | 157 |
| 51 | — | " | 7 | 150 |

TABLE 15

| Illustrative compound No. | Nonionic surfactant | Output wavelength of semiconductor laser (nm) | Relative intensity | |
|---|---|---|---|---|
| | | | Sample 1 | Sample 2 |
| 52 | Triton X-100 | 670 | 8 | 163 |
| 62 | " | " | 4 | 156 |
| 66 | " | " | 9 | 137 |

TABLE 15-continued

| Illustrative compound No. | Nonionic surfactant | Output wavelength of semiconductor laser (nm) | Relative intensity Sample 1 | Relative intensity Sample 2 |
|---|---|---|---|---|
| 70 | — | " | 3 | 145 |
| 74 | — | " | 5 | 132 |
| 77 | Triton X-100 | " | 7 | 114 |
| 82 | " | 780 | 4 | 166 |
| 86 | " | 830 | 5 | 143 |
| 90 | " | 780 | 5 | 136 |
| 91 | " | " | 7 | 164 |
| 94 | " | 830 | 8 | 128 |
| 101 | " | 670 | 7 | 155 |
| 105 | " | " | 2 | 138 |
| 109 | — | " | 5 | 149 |
| 112 | Tween 20 | " | 6 | 127 |
| 113 | " | " | 6 | 154 |
| 118 | " | " | 4 | 163 |
| 121 | Triton X-100 | 780 | 5 | 88 |
| 123 | " | " | 7 | 93 |
| 128 | " | " | 8 | 101 |

TABLE 16

| Illustrative compound No. | Nonionic surfactant | Output wavelength of semiconductor laser (nm) | Relative intensity Sample 1 | Relative intensity Sample 2 |
|---|---|---|---|---|
| 131 | Triton X-100 | 680 | 7 | 98 |
| 136 | " | " | 8 | 91 |
| 139 | " | " | 6 | 79 |
| 140 | " | " | 10 | 87 |
| 141 | " | 670 | 5 | 92 |
| 145 | " | " | 7 | 105 |
| 146 | " | " | 8 | 85 |
| 149 | " | " | 6 | 88 |
| 151 | " | " | 7 | 90 |
| 155 | " | " | 5 | 94 |
| 158 | " | " | 6 | 97 |
| 161 | " | 780 | 9 | 84 |
| 165 | " | 830 | 4 | 103 |
| 167 | " | " | 9 | 92 |
| 171 | Tween 20 | 670 | 8 | 86 |
| 175 | Triton X-100 | " | 7 | 90 |
| 177 | " | " | 6 | 85 |
| 179 | " | " | 9 | 89 |

Comparative Example 1

Each of the phthalocyanines disclosed in International Application Number PCT/US89/03807 was attached to the oligonucleotide primer obtained in Example 18, according to the methods of grafted patents and the methods described in Examples 19 to 25 of this invention. Using each of the phthalocyanine-attached oligonucleotides thus obtained, the base sequence of DNA was analyzed in the same manner as in Example 26.

The phthalocyanines used in this experiment are described below.

Comparative-example compound A: aluminum hydroxy-2,9,16,23-tetraphenoxyphthalocyaninesulfonate Comparative-example compound B: aluminum hydroxy-2,9,16,23-tetrathiophenylphthalocyaninesulfonate Comparative-example compound C: magnesium 20-phenyltetrabenztriazaporphinsulfonate Comparative-example compound D: sodium bis(-tributylsiloxy)silicon-phthalocyaninetetracarboxylate The results obtained are shown in Table 17.

As shown in Table 17, the phthalocyanines could not be excited by means of a semiconductor laser having an output wavelength of 730 nm or more, so that no fluorescence was observed at all. Therefore, measurement became impossible. Moreover, when a semiconductor laser having an output wavelength of 680 nm was used, the precision of measurement was significantly lowered by interference of scattered light.

TABLE 17

| Comparative example compound | Nonionic surfactant | Output wavelength of semiconductor laser (nm) | Number of bases of DNA | Precision |
|---|---|---|---|---|
| A | Triton X-100 | 830 | Not measurable | |
| " | " | 780 | " | |
| " | " | 730 | " | |
| " | " | 680 | 130 | 50% |
| B | " | 830 | Not measurable | |
| " | " | 780 | " | |
| " | " | 730 | " | |
| " | " | 680 | 120 | 48% |
| C | " | 830 | Not measurable | |
| " | " | 780 | " | |
| " | " | 730 | " | |
| " | " | 680 | 140 | 54% |
| D | " | 830 | Not measurable | |
| " | " | 780 | " | |
| " | " | 730 | " | |
| " | " | 680 | " | |

Comparative Example 2

The phthalocyanines of comparative-example compounds A to D were utilized for detecting β-globin in human DNA, in the same manner as in Example 27.

The results obtained are shown in Table 18.

As shown in Table 18, the phthalocyanines could not be excited by means of a semiconductor laser having an output wavelength of 730 nm or more, so that no fluorescence was observed at all. Therefore, measurement became impossible. Moreover, when a semiconductor laser having an output wavelength of 680 nm was used, it became difficult to distinguish relative fluorescence intensities between of sample 1 and of sample 2 because of interference of excitation light source.

TABLE 18

| Comparative example compound | Nonionic surfactant | Output wavelength of semiconductor laser (nm) | Relative intensity Sample 1 | Relative intensity Sample 2 |
|---|---|---|---|---|
| A | Triton X-100 | 830 | Not measurable | Not measurable |
| " | " | 780 | " | " |
| " | " | 730 | " | " |
| " | " | 680 | 125 | 146 |
| B | " | 830 | Not measurable | Not measurable |
| " | " | 780 | " | " |
| " | " | 730 | " | " |
| " | " | 680 | 118 | 151 |
| C | " | 830 | Not measurable | Not measurable |
| " | " | 780 | " | " |
| " | " | 730 | " | " |
| " | " | 680 | 131 | 144 |
| D | " | 830 | Not measurable | Not measurable |
| " | " | 780 | " | " |
| " | " | 730 | " | " |
| " | " | 680 | " | " |

Example 28

[Measurement of relative immuno-affinity for anti-morphine monoclonal antibody]

{Synthesis of sodium aluminum-naphthalocyaninemono-[N-(p-hydroxycarbonylphenyl)sulfamoyl]disulfonate (illustrative compound No. 128-PABA)}

To a solution of 150 mg of aluminum-naphthalocyaninetrisulfonic acid, i.e., a precursor for synthesis of illustrative compound No. 128, in 2 ml of benzene was added dropwise 0.75 ml of oxalyl chloride at 25° C. The resulting mixture was stirred at room temperature for 6 hours, after which the solvent was removed to obtain aluminum-naphthalocyaninetrisulfonyl chloride as a dark-green solid. On the other hand, 31 mg of p-aminobenzoic acid (PABA) was added to a solution of 61 mg of $Na_2CO_3$ in 1 ml of water at 80° C. The resulting mixture was stirred at 80° C. for 5 minutes and then 55 mg of the aluminum-naphthalocyaninetrisulfonyl chloride was added. The reaction mixture was stirred at 80° C. for 6 hours and the solvent was removed. The solid thus obtained was diluted with methanol containing 10 wt % $NH_4OH$, reconcentrated, and then ground by use of acetone to obtain sodium aluminum-naphthalocyaninemono[N-(p-hydroxycarbonylphenyl)sulfamoyl]disulfonate (illustrative compound No. 128-PABA).

{Synthesis of illustrative compound No. 1-PABA}

Octacarboxylic acid of illustrative compound No. 1 was obtained by acidifying 286 mg (0.13 mmol) of illustrative compound No. 1 with concentrated hydrochloric acid in methanol, followed by quick concentration under reduced pressure. The octacarboxylic acid of illustrative compound was dried under reduced pressure, after which 20 ml of DMF was added to extract only a soluble material from the dried product, whereby a dark-green DMF solution was obtained. To this solution was added 18 mg (0.13 mmol) of PABA. With cooling at least 0° C., to the resulting solution were added a solution of 0.02 ml of diethylphosphoryl cyanide (DEPC) in 3 ml of DMF, and then 0.04 ml (0.28 mmol) of triethylamine, and the resulting mixture was stirred at 0° C. for 30 minutes. Then, the stirring was continued at room temperature for 3 hours. After completion of the reaction, 1 ml of water was added to the reaction mixture, followed by concentration under reduced pressure and a reverse phase column chromatography, whereby illustrative compound No. 1-PABA was obtained.

{Synthesis of illustrative compound No. 21-PABA}

Illustrative compound No. 21-PABA was obtained by treating illustrative compound No. 21 in the same manner as that of the synthesis of illustrative compound No. 1-PABA.

{Synthesis of illustrative compound No. 42-PABA}

Illustrative compound No. 42-PABA was obtained by treating illustrative compound No. 42 in the same manner as that of the synthesis of illustrative compound No. 1-PABA.

{Synthesis of illustrative compound No. 62-PABA}

Illustrative compound No. 62-PABA was obtained by treating illustrative compound No. 62 in the same manner as that of the synthesis of illustrative compound No. 1-PABA.

{Synthesis of illustrative compound No. 82-PABA}

Illustrative compound No. 82-PABA was obtained by treating illustrative compound No. 82 in the same manner as that of the synthesis of illustrative compound No. 1-PABA.

{Synthesis of illustrative compound No. 101-PABA}

Illustrative compound No. 101-PABA was obtained by treating illustrative compound No. 101 in the same manner as that of the synthesis of illustrative compound No. 1-PABA.

{Synthesis of illustrative compound No. 128-PABA-morphine}

Illustrative compound No. 128-PABA-morphine was obtained by treating a solution of illustrative compound No. 128-PABA and 3-(4-aminobutyl)morphine in DMF with DEPC in the presence of triethylamine in the same manner as that of the synthesis of illustrative compound No. 1-PABA.

{Synthesis of illustrative compound No. 1-PABA-morphine}

Illustrative compound No. 1-PABA-morphine was obtained by treating illustrative compound No. 1-PABA in the same manner as that of the synthesis of illustrative compound No. 128-PABA-morphine.

{Synthesis of illustrative compound No. 21-PABA-morphine}

Illustrative compound No. 21-PABA-morphine was obtained by treating illustrative compound No. 21-PABA in the same manner as that of the synthesis of illustrative compound No. 128-PABA-morphine.

{Synthesis of illustrative compound No. 42-PABA-morphine}

Illustrative compound No. 42-PABA-morphine was obtained by treating illustrative compound No. 42-PABA in the same manner as that of the synthesis of illustrative compound No. 128-PABA-morphine.

{Synthesis of illustrative compound No. 62-PABA-morphine}

Illustrative compound No. 62-PABA-morphine was obtained by treating illustrative compound No. 62-PABA in the same manner as that of the synthesis of illustrative compound No. 128-PABA-morphine.

{Synthesis of illustrative compound No. 82-PABA-morphine]

Illustrative compound No. 82-PABA-morphine was obtained by treating illustrative compound No. 82-PABA in the same manner as that of the synthesis of illustrative compound No. 128-PABA-morphine.

{Synthesis of illustrative compound No. 101-PABA-morphine}

Illustrative compound No. 101-PABA-morphine was obtained by treating illustrative compound No. 101-PABA in the same manner as that of the synthesis of illustrative compound No. 128-PABA-morphine.

{Measurement of relative immuno-affinity for anti-morphine monoclonal antibody}

For morphine, aminomorphine and the above-mentioned fluorochrome-labeled morphines, relative immuno-affinity for anti-morphine monoclonal antibody was measured using a competitive reaction in which they competed with tritium-labeled morphine. The results obtained are summarized in Table 19.

From the results shown in Table 19, it can be seen that the relative affinity is hardly different for different molecular species, and that the labeling with the fluorochrome hardly changes the reactivity of morphine with the monoclonal antibody.

TABLE 19

| Molecular species | Relative affinity |
|---|---|
| Morphine | 1 |

TABLE 19-continued

| Molecular species | Relative affinity |
| --- | --- |
| Aminomorphine | 1 |
| Illustrative compound No. 128-PABA-morphine | 0.8 |
| Illustrative compound No. 1-PABA-morphine | 0.95 |
| Illustrative compound No. 21-PABA-morphine | 0.97 |
| Illustrative compound No. 42-PABA-morphine | 0.98 |
| Illustrative compound No. 62-PABA-morphine | 0.96 |
| Illustrative compound No. 82-PABA-morphine | 0.98 |
| Illustrative compound No. 101-PABA-morphine | 0.97 |

As described above, this invention provides a reagent or a reagent for clinical examination, which is not affected by substances in a living body, such as hemes present in blood, and is useful for assay of various antigens, drugs, DNAs, etc. and analysis of the base sequence of DNA which use an inexpensive semiconductor laser (670 to 840 nm).

What is claimed is:

1. A water-soluble tetraazaporphin represented by the formula (I):

wherein M is $H_2$, Mg, Al, Si, P, Zn, Ga, Ge or Sc; Y is a halogen atom, $-OR^1$, $-NR^2_2$ or $-SR^3$ (wherein $R^1$, $R^2$ and $R^3$ are independently a hydrogen atom, an alkyl group which may have one or more hydrophilic substituents, an aryl group which has 4 to 18 carbon atoms and which may have one or more hydrophilic substituents, an aralkyl group which has 7 to 8 carbon atoms and which may have one or more hydrophilic substituents, an acyl group which has 1 to 18 carbon atoms and which may have one or more hydrophilic substituents, said acyl group being derived from a carboxylic acid by the removal of the hydroxyl group, a silyl group which may have one or more hydrophilic substituents, or a phosphorus-atom-containing group which may have one or more hydrophilic substituents, said hydrophilic substituent being a hydroxyl group, a carboxylic acid group, a sulfonic acid group or phosphoric acid group); p is zero or an integer of 1 or 2 indicating the number of Y's bonded to M; A is a fused polycyclic aromatic ring formed from two or more aromatic rings containing no more than 18 carbon atoms and having substituents XQ's in a number of m (X is an oxygen atom or a sulfur atom; and Q is a saturated hydrocarbon group, or unsaturated hydrocarbon group which has 2 to 10 carbon atoms or a heterocyclic ring selected from furyl group, thienyl group and pyrrolyl group; and each m is the same or different and independently an integer of 1 to 4); each n is the same or different and independently zero or an integer of 1 or more, 4n (the sum of four n's) being an integer of 1 or more; each substituent (EZ) in a number of n is the same or different and are independently bonded to the fused polycyclic aromatic ring A and/or Q; and E is a cationic group in the case of Z being an anion, E is an anionic group in the case of Z being a cation; said cationic group (E) being

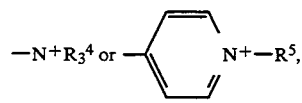

wherein $R^4$ and $R^5$ are independently an alkyl group which may have one or more hydrophilic substituents, an aryl group which has 4 to 18 carbon atoms and which may have one or more hydrophilic substituents, or an aralkyl group which has 7 to 8 carbon atoms and which may have one or more hydrophilic substituents, said hydrophilic substituent being a hydroxyl group, a carboxylic acid group, a sulfonic acid group, or phosphoric acid group and said anionic group (E) being $-COO^-$, $-OSO_3^-$, $-OPO_3^-$, $-SO_3^-$, or

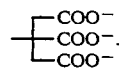

2. A fluorochrome for labeling consisting essentially of water and a water-soluble compound in an aqueous solution, said compound being represented by the formula (II):

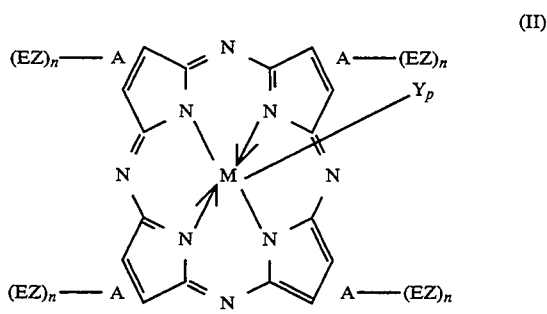

(II)

wherein M is $H_2$, Mg, Al, Si, P, Zn, Ga, Ge or Sc; Y is a halogen atom, $-OR^1$, $-NR^2_2$ or $-SR^3$ (wherein $R^1$, $R^2$ and $R^3$ are independently a hydrogen atom, an alkyl group which may have one or more hydrophilic substituents, an aryl group which has 4 to 18 carbon atoms and which may have one or more hydrophilic substituents, an aralkyl group which has 7 to 8 carbon atoms and which may have one or more hydrophilic substituents, an acyl group which has 1 to 18 carbon atoms and which may have one or more hydrophilic substituents, said acyl group being derived from a carboxylic acid by the removal of the hydroxyl group, a silyl group which may have one or more hydrophilic substituents, or a phosphorus-atom-containing group which may have one or more hydrophilic substituents, said hydrophilic substituent being a hydroxyl group, a carboxylic acid group, a sulfonic acid group or phosphoric acid group); p is zero or an integer of 1 or 2 indicating the number of Y's bonded to M; A is a fused polycyclic aromatic ring formed from two or more aromatic rings containing no more than 18 carbon atoms, said polycyclic aromatic ring being able to have substituents $X^1Q$'s or Q's in a number of m ($X^1$ is an oxygen atom, a sulfur atom, a nitrogen atom, a phosphorus atom, a silicon atom, a selenium atom, $NH.CO$, $NH.PO_2$, $NH.SO_2$, $O.CO$, $O.SO_2$, $O.PO_2$, $S.CO$, $S.SO_2$, $S.PO_2$, $CO$, $SO_2$ or $PO_2$; Q is a saturated hydrocarbon group or unsaturated hydrocarbon group which has 2 to 10 carbon atoms or a heterocyclic ring selected from furyl group, thienyl group and pyrrolyl group; and each m is the same or different and independently an integer of 1 to 4); each n is the same or different and independently zero or an integer of 1 or more, 4n (the sum of four n's) being an integer of 1 or more; each substituent (EZ) in a number of n is the same or different and independently bonded to the fused polycyclic aromatic ring A and/or Q; and E is a cationic group in the case of Z being an anion, E is an anionic group in the case of Z being a cation, and E is a bonded group containing a polyethylene glycol residue, in the case of Z being absent; said cationic group (E) being —N+R4$_3$ or

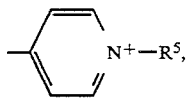

wherein R$^4$ and R$^5$ are independently an alkyl group which may have one or more hydrophilic substituents, an aryl group which has 4 to 18 carbon atoms and which may have one or more hydrophilic substituents, or an aralkyl group which has 7 to 8 carbon atoms and which may have one or more hydrophilic substituents, said hydrophilic substituent being a hydroxyl group, a carboxylic acid group, a sulfonic acid group, or phosphoric acid group and said anionic group (E) being —COO$^-$, —OSO$_3^-$, —OPO$_3^-$, —SO$_3^-$, or

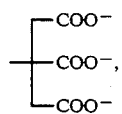

whereby the fluorochrome shows more than 0.1 of fluorescence quantum yield.

3. A reagent for fluorescence analysis method comprising the fluorochrome for labeling of claim 2 and a carrier.

4. A reagent for fluorescence analysis method comprising the fluorochrome for labeling of claim 2 and a surfactant.

5. A water-soluble tetraazaporphin according to claim 1, wherein E is an anionic group selected from the group consisting of —COO$^-$, —OSO$_3^-$, —OPO$_3^-$,

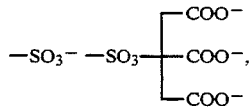

and Z is a cation selected from the group consisting of H+, Li+, Na+, K+, Mg$^{2+}$, Ca$^{2+}$, and an ammonium ion; or E is a bonded group containing a polyethylene glycol residue, a polyether residue, a polyamine residue, a polyalcohol residue or a polycarboxylic acid residue and Z being absent.

6. A water-soluble tetraazaporphin according to claim 1, wherein E is —COO$^-$, —OSO$_3^-$, —OPO$_3^-$,

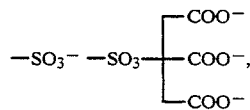

and Z is H+, Li+, Na+, K+, Mg$^{2+}$, Ca$^{2+}$, or an ammonium ion.

7. A water-soluble tetraazaporphin according to claim 1, wherein EZ is —CO$_2$Na, —SO$_3$Na, —OPO$_3$Na or

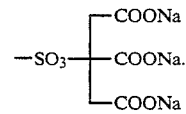

8. A water-soluble tetraazaporphin according to claim 1, wherein XQ is

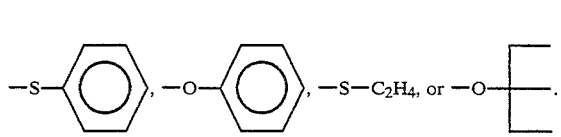

9. A water-soluble tetraazaporphin according to claim 7, wherein XQ is

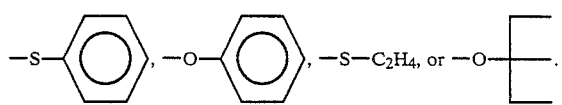

10. A water-soluble tetraazaporphin according to claim 1, wherein four A's in the formula (I) are the same fused polycyclic aromatic ring having 10 to 18 carbon atoms.

11. A water-soluble tetraazaporphin according to claim 1, wherein M is H$_2$, Mg, Al, Si, P or Zn.

12. A water-soluble tetraazaporphin according to claim 1, wherein M is H$_2$, Al, Si, or Zn.

13. A water-soluble tetraazaporphin according to claim 1, wherein Y is —OR$^1$; and R$^1$ is as defined in claim 1.

14. A water-soluble tetraazaporphin according to claim 13, wherein R$^1$ is an alkyl group which may have one or more hydrophilic substituents, an aryl group which may have one or more hydrophilic substituents, an aralkyl group which may have one or more hydrophilic substituents, a silyl group which may have one or more hydrophilic substituents, or a phosphorus-atom-containing group which may have one or more hydrophilic substituents, said hydrophilic substituent being a hydroxyl group, a carboxylic acid group, a sulfonic acid group, or a phosphoric acid group.

15. A water-soluble tetraazaporphin according to claim 13, wherein R$^1$ is an alkyl group which may have one or more hydrophilic substituents, an aryl group which may have one or more hydrophilic substituents, or a silyl group which may have one or more hydrophilic substituents, said hydrophilic substituent being a hydroxyl group, a carboxylic acid group, a sulfonic acid group, or a phosphoric acid group.

16. A water-soluble tetraazaporphin according to claim 15, wherein M is H$_2$, Al, Si or Zn.

17. A water-soluble tetraazaporphin according to claim 10, wherein A is a naphthalene ring.

18. A water-soluble tetraazaporphin according to claim 10, wherein A is an anthracene ring.

19. A water-soluble tetraazaporphin according to claim 10, wherein A is a phenanthrene ring.

20. A water-soluble tetraazaporphin according to claim 10, wherein A is a quinoline ring.

21. A water-soluble tetraazaporphin according to claim 10, wherein A is a quinoxaline ring.

22. A water-soluble tetraazaporphin according to claim 10, wherein A is a chrysene ring.

23. A fluorochrome for labeling according to claim 2, wherein E is an anionic group selected from the group consisting of —COO⁻, —OSO$_3^-$, —OPO$_3^-$, and —SO$_3^-$, and Z is a cation selected from the group consisting of H⁺, Li⁺, Na⁺, K⁺, Mg²⁺, Ca²⁺, and an ammonium ion; or E is a bonded group containing a polyethylene glycol residue, a polyether residue, a polyamine residue, a polyalcohol residue or a polycarboxylic acid residue and Z being absent.

24. A fluorochrome for labeling according to claim 2, wherein E is —COO⁻, —OSO$_3^-$, —OPO$_3^-$, or —SO$_3^-$, and Z is H⁺, Li⁺, Na⁺, K⁺, Mg²⁺, Ca²⁺, or an ammonium ion.

25. A fluorochrome for labeling according to claim 2, wherein EZ is —CO$_2$Na, —SO$_3$Na, —OPO$_3$Na or

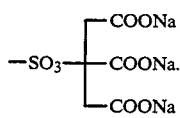

26. A fluorochrome for labeling according to claim 2, wherein four A's in the formula (I) are the same fused polycyclic aromatic ring having 10 to 18 carbon atoms.

27. A fluorochrome for labeling according to claim 2, wherein M is H$_2$, Mg, Al, Si, P or Zn.

28. A fluorochrome for labeling according to claim 2, wherein M is H$_2$, Al, Si, or Zn.

29. A fluorochrome for labeling according to claim 2, wherein Y is —OR¹; and R¹ is as defined in claim 2.

30. A fluorochrome for labeling according to claim 29, wherein R¹ is an alkyl group which may have one or more hydrophilic substituents, an aryl group which may have one or more hydrophilic substituents, an aralkyl group which may have one or more hydrophilic substituents, a silyl group which may have one or more hydrophilic substituents, or a phosphorus-atom-containing group which may have one or more hydrophilic substituents, said hydrophilic substituent being a hydroxyl group, a carboxylic acid group, a sulfonic acid group, or a phosphoric acid group.

31. A fluorochrome for labeling according to claim 29, wherein R¹ is an alkyl group which may have one or more hydrophilic substituents, an aryl group which may have one or more hydrophilic substituents, or a silyl group which may have one or more hydrophilic substituents, said hydrophilic substituent being a hydroxyl group, a carboxylic acid group, a sulfonic acid group, or a phosphoric acid group.

32. A fluorochrome for labeling according to claim 31, wherein M is H$_2$, Al, Si or Zn.

33. A fluorochrome for labeling according to claim 26, wherein A is a naphthalene ring.

34. A fluorochrome for labeling according to claim 26, wherein A is an anthracene ring.

35. A fluorochrome for labeling according to claim 26, wherein A is a phenanthrene ring.

36. A fluorochrome for labeling according to claim 26, wherein A is a quinoline ring.

37. A fluorochrome for labeling according to claim 26, wherein A is a quinoxaline ring.

38. A fluorochrome for labeling according to claim 26, wherein A is a chrysene ring.

39. A fluorochrome for labeling consisting essentially of a water-soluble compound represented by formula (I) of claim 1.

40. A reagent for fluorescence analysis method comprising the fluorochrome for labeling of claim 39 and a carrier.

41. A reagent for fluorescence analysis method comprising the fluorochrome for labeling of claim 39 and a surfactant.

42. A fluorochrome for labeling consisting essentially of water and a water-soluble compound in an aqueous solution, said compound being represented by formula (I) of claim 1, whereby the fluorochrome shows more than 0.1 of fluorescence quantum yield.

* * * * *